(12) United States Patent
Variano

(10) Patent No.: US 12,303,518 B2
(45) Date of Patent: *May 20, 2025

(54) SYSTEM FOR PROVIDING BIRTH CONTROL

(71) Applicant: The Population Council, Inc., New York, NY (US)

(72) Inventor: Bruce Variano, New York, NY (US)

(73) Assignee: The Population Council, Inc., New York, NY (US)

(*) Notice: Subject to any disclaimer, the term of this patent is extended or adjusted under 35 U.S.C. 154(b) by 26 days.

This patent is subject to a terminal disclaimer.

(21) Appl. No.: 17/520,323

(22) Filed: Nov. 5, 2021

(65) Prior Publication Data

US 2022/0054503 A1 Feb. 24, 2022

Related U.S. Application Data

(63) Continuation of application No. 17/188,857, filed on Mar. 1, 2021, which is a continuation of application No. 16/814,724, filed on Mar. 10, 2020, now Pat. No. 10,940,157, which is a continuation of application No. 16/448,399, filed on Jun. 21, 2019, now Pat. No. 10,918,649.

(51) Int. Cl.
*A61K 31/57* (2006.01)
*A61K 9/00* (2006.01)

(52) U.S. Cl.
CPC ............ *A61K 31/57* (2013.01); *A61K 9/0036* (2013.01)

(58) Field of Classification Search
CPC .............................. A61K 9/0036; A61P 15/18
See application file for complete search history.

(56) References Cited

U.S. PATENT DOCUMENTS

| | | | |
|---|---|---|---|
| 5,972,372 A | 10/1999 | Saleh | |
| 5,989,581 A | 11/1999 | Groenewegen | |
| 8,753,667 B2 | 6/2014 | Variano et al. | |
| 9,296,780 B2 | 3/2016 | Fuentes | |
| 10,632,066 B1 | 4/2020 | Creasy | |
| 10,765,628 B2 | 9/2020 | Creasy | |
| 10,780,047 B2 | 9/2020 | Creasy | |
| 10,918,649 B2 | 2/2021 | Variano | |
| 10,925,882 B2 | 2/2021 | Variano | |
| 10,940,157 B2 | 3/2021 | Variano | |
| 11,529,308 B2 | 12/2022 | Variano | |
| 2002/0132801 A1 | 9/2002 | Heil | |
| 2009/0004246 A1* | 1/2009 | Woolfson | C07K 16/1063 424/430 |
| 2013/0171265 A1 | 7/2013 | Saxena | |
| 2014/0161758 A1 | 6/2014 | Tamura | |
| 2015/0004214 A1* | 1/2015 | Fuentes Garcia | A61P 15/08 424/432 |
| 2020/0246258 A1 | 8/2020 | Creasy | |
| 2020/0397692 A1 | 12/2020 | Variano | |
| 2021/0290637 A1 | 9/2021 | Variano | |
| 2023/0090841 A1 | 3/2023 | Creasy et al. | |
| 2023/0240982 A1 | 8/2023 | Variano | |

FOREIGN PATENT DOCUMENTS

| | | |
|---|---|---|
| GB | 1581474 A | 12/1980 |
| HU | 0004967 A2 | 9/2002 |
| WO | WO 98/04220 A1 | 2/1998 |
| WO | WO-2009003125 A1 | 12/2008 |
| WO | WO-2009/099586 A2 | 8/2009 |
| WO | WO-2011/120925 A1 | 10/2011 |
| WO | WO-2013/029194 A1 | 3/2013 |
| WO | WO-2015/086491 A1 | 6/2015 |
| WO | WO 2016/065096 A1 | 4/2016 |
| WO | WO 2022/236045 A1 | 11/2022 |

OTHER PUBLICATIONS

"Annovera™: Highlights of Prescribing Information," TherapeuticsMD, Aug. 2018, 38 pages.
"Elcometrine—Population Council/Orion," Adis International Ltd., *Springer Nature Switerland AG*, Jan. 26, 2015, 11 pages.
"NuvaRing®: Highlights of Prescribing Information," Merck & Co., Oct. 2013, 36 pages.
"Safety and Efficacy of a Contraceptive Vaginal Ring Delivering Nesterone® and Ethinyl Estradiol," Population Council, https://clinicaltrials.gov/ct2/show/NCT00263341, first available online Dec. 8, 2005, 8 pages.
"Study of Efficacy, Cycle Control, and Safety of a NES-E2 Contraceptive Vaginal Ring," Population Council, https://clinicaltrials.gov/ct2/show/NCT03432416, first available online Feb. 14, 2018, 13 pages.
Archer, D. F., et al., "Impact of a One-Year Contraceptive Vaginal Ring Delivering Nestorone and Ethinyl Estradiol on Hepatic Estrogen-Sensitive Proteins," *Reproductive Sciences*, vol. 22(1): 111A-112A, Sage Journals, United States (2015).
Creasy, G., et al., "User controlled long acting reversible contraception: The pharmacokinetic profile of the Nestorone®/Ethinyl Estradiol Contraceptive Vaginal Ring(NES/EE-CVR) a 1-year Cyclical Re-useable Vaginal Ring," *The European Journal of Contraception and Reproductive Health Care*: S85, Taylor & Francis, United Kingdom (2014).
Edelman, A., et al., "A Novel Contraceptive Vaginal Ring Releasing Nestorone and Estradiol Dosed Continuously: Pharmacokinetics From a Dose Finding Study," *Fertility and Sterility*108(3): e121, Elsevier, Netherlands (2017).
Fraser, I. S., et al., "Serum Nestorone® and ethinyl estradiol levels, and ovulation inhibition in women using three different dosage combinations of a Nestorone progestogen-ethinyl estradiol contraceptive vaginal ring on a bleeding-signaled regimen," *Contraception* 72: 40-45, Elsevier, Netherlands (2005).

(Continued)

*Primary Examiner* — Nicole P Babson
*Assistant Examiner* — John P Nguyen
(74) *Attorney, Agent, or Firm* — Sterne, Kessler, Goldstein & Fox P.L.L.C.

(57) ABSTRACT

The present disclosure relates to a vaginal system that prevents pregnancy comprised of segesterone acetate and ethinyl estradiol and is configured for thirteen 28-day product-use cycles.

15 Claims, 26 Drawing Sheets

(56) References Cited

OTHER PUBLICATIONS

Hoskin, E., et al., "Cycle control and bleeding patterns for a new contraceptive vaginal ring delivering 150 µg Nestorone® and 15 µg Ethinyl Estradiol: Results from a multi-centre, multi-national open label Phase 3 clinical trial," *The European Journal of Contraception and Reproductive Health Care*: S82-S83, Taylor & Francis, United States (2014).

Jensen, J. T., et al., "Use of Peak Drug Levels to Assess Compliance with Vaginal Ring Contraception," *ASRM Abstracts* 108(3): e12, Elsevier, Netherlands (2017).

Jensen, J. T., et al., "Continuous dosing of a novel contraceptive vaginal ring releasing Nestorone® and estradiol: pharmacokinetics from a dose-finding study," *Contraception* 97: 422-427, Elsevier, Netherlands, (2018).

Kumar, N., et al., "Nestorone® as a Novel Progestin for Nonoral Contraception: Structure-Activity Relationships and Brain Metabolism Studies," *Endocrinology* 158(1): 170-182, Oxford Academic, United Kingdom (2017).

Malcolm, K., et al., "Influence of silicone elastomer solubility and diffusivity on the in vitro release of drugs from intravaginal rings," *Journal of Controlled Release* 90: 217-225, Elsevier, Netherlands (2003).

Massai, M. R., et al., "Contraceptive efficacy and clinical performance of Nestorone implants in postpartum women," *Contraception* 64: 369-376, Elsevier, Netherlands (2001).

Merkatz, R., et al., "Preliminary results from a phase III study of the nestorone®/ethinyl estradiol contraceptive vaginal ring: a new, long acting (one year) user controlled contraceptive method," *The European Journal of Contraception and Reproductive Health Care: Abstracts of Free Communications*: FC-01, Taylor & Francis, United Kingdom (2010).

Merkatz, R., et al., "Efficacy, Safety and Acceptability of a New Contraceptive Vaginal Ring Delivering Nestorone (150µg) and Ethinyl Estradiol (15µg) Daily: Results From a Multi-Center Open Label Phase 3 Clinical Trial," *ASRM Abstracts* 100(3): S58, Taylor & Francis, United Kingdom (2013).

Merkatz, R., et al., "Efficacy, safety and acceptability of a new contraceptive vaginal ring delivering 150 µg Nestorone® and 15 µg Ethinyl Estradiol daily: Results from a multicenter open label Phase 3 clinical trial," *The European Journal of Contraception and Reproductive Health Care: Abstracts of Free Communications*:S67, Taylor & Francis, United Kingdom (2013).

Merkatz, R., et al., "Acceptability of the Nestorone®/Ethinyl Estradiol Contraceptive Vaginal Ring: Development of a Model; Implications for Introduction," *International Journal of Gynecology and Obstetrics* 131(5): E395-E396, Wiley Blackwell, United Kingdom (2015).

Merkatz, R., et al., "An acceptability model for the Nestorone® /Ethinyl Estradiol contraceptive vaginal ring," *The European Journal of Contraception and Reproductive Health Care* :S203-S204 , Taylor & Francis, United Kingdom(2016).

Merkatz, R., et al., "Efficacy, Safety and Acceptability of a New Contraceptive Vaginal Ring Delivering Nestorone® 150 µg and Ethinyl Estradiol: Results From an Open Label Phase 3 Clinical Trial," *International Journal of Gynecology and Obstetrics* 131(5): E395, Wiley-Blackwell, United Kingdom (2015).

Merkatz, R., et al., "Development of the Nestorone®/Ethinyl Estradiol Contraceptive Vaginal Ring (NES/EE CVR); Challenges, Opportunities and Obligations of the Public Sector," *The European Journal of Contraception and Reproductive Health Care*: S192-S193, Taylor & Francis, United Kingdom (2016).

Mishell, D., et al., "Maximum Concentration and Exposure to Ethinyl Estradiol From the Nestorone®/Ethinyl Estradiol Contraceptive Vaginal Ring (NES/EE CVR)," *Reproductive Sciences* 22(1): 112A-113A, Sage Journals, United States (2015).

Rad, M., et al., "Comparative effects of a contraceptive vaginal ring delivering a nonandrogenic progestin and continuous ethinyl estradiol and a combined oral contraceptive containing levonorgestrel on hemostasis variables," *American Journal of Obstetrics and Gynecology* 195(1): 72-77, Elsevier, Netherlands (2006).

Rad, M., et al., "Effects of a contraceptive vaginal ring delivering nestorone® and ethinyl estradiol, and a combined oral contraceptive containing levonorgestrel, on markers of arterial disease," *Br. J. Clin. Pharmacol* 60(6): 677, Wiley Blackwell,United Kingdom (2005).

Robbins, A., et al., "Nestorone™ Progestin: The Ideal Progestin for Use in Controlled Release Delivery Systems," *Ann. N Y Acad. Sci* 828: 38-46, Wiley-Blackwell, United States (1997).

Sitruk-Ware, R., et al., "Nestorone®: clinical applications for contraception and HRT," *Steroids* 68: 907-913, Elsevier, Netherlands (2003).

Sitruk-Ware, R., et al., "A one-year contraceptive vaginal ring delivering Nestorone® and Ethinyl-Estradiol," *The European Journal of Contraception and Reproductive Health Care* :211, Taylor & Francis, United States (2014).

Sivin, I., et al., "Two-year performance of Nestorone®-releasing contraceptive implant: a three-center study of 300 women," *Contraception* 69: 137-144, Elsevier, Netherlands (2004).

Sivin, I., et al., "Contraceptive vaginal rings releasing Nestorone® and ethinylestradiol: a 1-year dose-finding trial," *Contraception* 71: 122-129, Elsevier, Netherlands (2005).

Stifani, B. M., et al., "Factors associated with nonadherence to instructions for using the Nestorone®/ethinyl estradiol contraceptive vaginal ring," *Contraception* 97: 415-421, Elsevier, Netherlands (2018).

Weisberg, E., et al., "Efficacy, Bleeding Patterns, and Side Effects of a 1-Year Contraceptive Vaginal Ring," *Contraception* 59: 311-318, Elsevier, Netherlands (1999).

Mccoy, C. F., et al., "Solid state $^{13}$C NMR spectroscopy provides direct evidence for reaction between ethinyl estradiol and a silicone elastomer vaginal ring drug delivery system," *International Journal of Pharmaceutics* 548: 689-697, Elsevier, Netherlands (2018).

Merkatz, R. B., et al., "Acceptability of the nestorone®/ethinyl estradiol contraceptive vaginal ring: development of a model; implications for introduction," *Contraception* 90: 514-521, Elsevier, Netherlands (2014).

Sivin, I., et al., "Recent developments in contraceptive implants at the Population Council," *Contraception* 65: 113-119, Elsevier, Netherlands (2002).

Pheasant, R., "Polymorphism of 17-Ethinylestradiol," *J. Am. Chem. Soc.* 72: 4303-4304 (1950).

MED-1134 Safety Data Sheet, Date of Issue: Feb. 26, 2015.
MED-6385 Safety Data Sheet, Date of Issue: Feb. 14, 2014.
MED-6382 Safety Data Sheet, Date of Issue: Jan. 15, 2014.
MED-6381 Safety Data Sheet, Date of Issue: Jun. 26, 2014.
MED-6603 Safety Data Sheet, Date of Issue: Mar. 5, 2015.
MED-4870 Safety Data Sheet, Date of Issue: May 10, 2013.
MED4-4224 Safety Data Sheet, Date of Issuance: Jan. 6, 2015.
DDU-4320 Safety Data Sheet, Date of Issuance: Apr. 14, 2014.

Murphy, D. J. et al., "Controlling Levonorgesterel Binding and Release in a Multi-Purpose Prevention Technology Vaginal Ring Device," *J. Controlled Release* 226: 138-147 (2016).

Office Action mailed Mar. 25, 2021 in U.S. Appl. No. 16/830,608, Inventors, Creasy, G. W. et al., filed Mar. 26, 2020.

Office Action mailed Sep. 5, 2019 in U.S. Appl. No. 16/265,222, Inventors, Creasy, G. W. et al., filed Feb. 1, 2019.

Crucitti, T., et al., "Contraceptive rings promote vaginal lactobacilli in a high bacterial vaginosis prevalence population: A randomized, open-label longitudinal study in Rwandan women," *PLoS One*, 13(7): 1-17, Public Library of Science, UnitedStates (Jul. 23, 2018).

Huang, Y., et al., "Effects of a One Year reusable Contraceptive Vaginal Ring on Vaginal Microflora and the Risk of Vaginal Infection: An Open-label Prospective Evaluation," *PLoS One*,10(8), pp. 1-16. (2015).

NuvaRing®: Center for Drug Evaluation and Research, Oct. 2013, 155 pages.

Sha, B.E. et al., "Utility of Amsel Criteria, Nugent Score, and Quantitative PCR for *Gardnerella vaginalis, Mycoplasma hominis,* and *Lactobacillus* spp. for Diagnosis of Bacterial Vaginosis in Human Immunodeficiency Virus-Infected Women" *Journal of Clinical Microbiology*, 43: 4607-4612 (2005).

Office Action mailed Jun. 16, 2020 in U.S. Appl. No. 16/448,399, Inventor, Variano, filed Jun. 21, 2019.

(56) References Cited

OTHER PUBLICATIONS

Notice of Allowance mailed Dec. 14, 2020, in U.S. Appl. No. 16/448,399, Inventors Variano, filed Jun. 21, 2019.
Office Action mailed Jun. 12, 2020 in U.S. Appl. No. 16/814,724, Inventor, Variano, filed Mar. 10, 2020.
Notice of Allowance mailed Dec. 10, 2020, in U.S. Appl. No. 16/814,724, Inventor, Variano, filed Mar. 10, 2020.
Notice of Allowance mailed Mar. 18, 2020, in U.S. Appl. No. 16/265,222, Inventors, Creasy II, G. W., et al., filed Feb. 1, 2019.
Office Action mailed Dec. 24, 2021 in U.S. Appl. No. 16/995,388, Inventor, Variano, filed Aug. 17, 2020.
Office Action mailed Apr. 30, 2020 in U.S. Appl. No. 16/825,472, Inventor, Creasy II, G. W., filed Mar. 20, 2020.
Notice of Allowance mailed Jun. 4, 2020, in U.S. Appl. No. 16/825,472, Inventors, Creasy II, G. W., et al., filed Mar. 20, 2020.
Notice of Allowance mailed Jul. 27, 2020, in U.S. Appl. No. 16/825,472, Inventors, Creasy II, G. W., et al., filed Mar. 20, 2020.
Office Action mailed May 14, 2020 in U.S. Appl. No. 16/825,522, Inventor, Creasy II, G. W., filed Mar. 20, 2020.
Notice of Allowance mailed May 29, 2020, in U.S. Appl. No. 16/825,522, Inventors, Creasy II, G. W., et al., filed Mar. 20, 2020.
Notice of Allowance mailed Jul. 24, 2020, in U.S. Appl. No. 16/825,522, Inventors, Creasy II, G. W., et al., filed Mar. 20, 2020.
Office Action mailed Oct. 14, 2020 in U.S. Appl. No. 16/830,608, Inventors, Creasy II, G. W., G. W., et al., filed Mar. 26, 2020.
Office Action mailed Jun. 12, 2020, in U.S. Appl. No. 16/827,388, Inventor, Variano, filed Mar. 23, 2020.
Weisberg, Edith, et al. "Clinical performance and menstrual bleeding patterns with three dosage combinations of a Nestorone® progestogen/ethinyl estradiol contraceptive vaginal ring used on a bleeding-signaled regimen." Contraception 72(1): 46-52, Elsevier, Netherlands (2005).
Simmons, Katharine B. et al. "Effects of concurrent vaginal miconazole treatment on the absorption and exposure of Nesterone® (segesterone acetate) and ethinyl estradiol delivered from a contraceptive vaginal ring: a randomized, crossover drug-drug interaction study." Contraception 97: 270-276, Elsevier, Netherlands (2018).
Notice of Allowance mailed Dec. 10, 2020, in U.S. Appl. No. 16/827,388, Inventors, Variano, filed Mar. 23, 2020.
Notice of Allowance mailed Aug. 16, 2022 in U.S. Appl. No. 16/995,388, Inventor, Bruce Variano, filed Aug. 17, 2020, 8 pages.
Office Action mailed Jun. 8, 2023 in U.S. Appl. No. 17/726,305, Inventor, George W. Creasy II, filed Apr. 21, 2022, 17 pages.

\* cited by examiner

Top: Ethinyl estradiol (EE)/Nestorone® Core
Second: Nestorone Progestin (Form I), x axis truncated to 7°-26° (2θ)
Third: Nesterone Progestin (Form II), x axis truncated to 7°-26° (2θ)

The intensity scale (y axis) is normalized to the most intense peak for each pattern and the patterns are offset by arbitrary units.

Top: Ethinyl estradiol (EE)/Nestorone® Core
Second: Ethinyl estradiol hemihydrate
Third: Ethinyl estradiol, anhydrous

| Name | Structure |
|---|---|
| 6α-OH-EE | 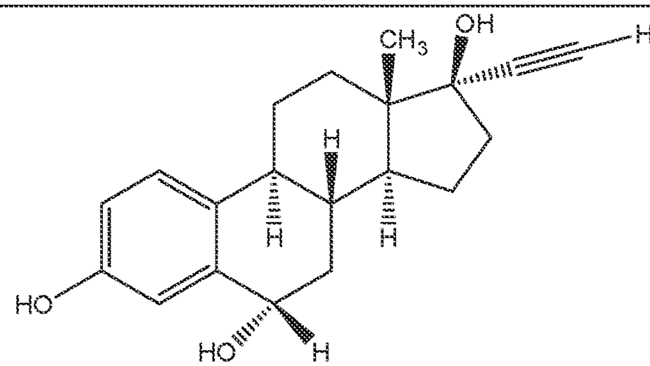 |
| 6β-OH-EE | 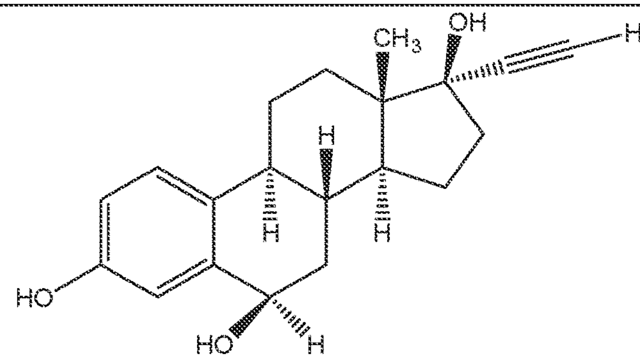 |
| 6α-OH-NES | 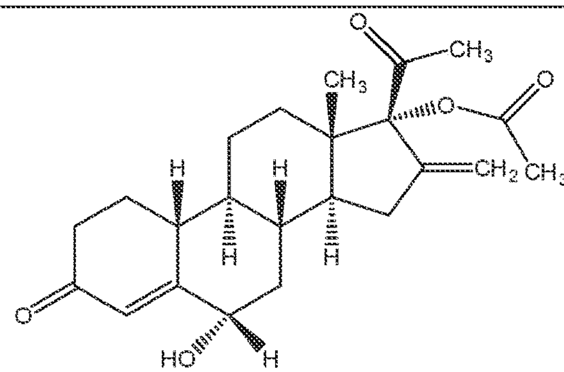 |
| 6β-OH-NES | 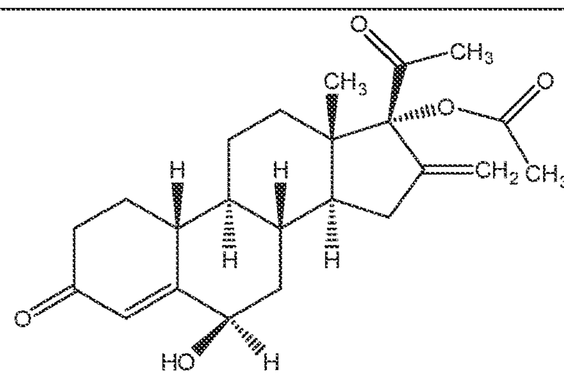 |

FIG. 10A

| Name | Structure |
|---|---|
| 6-keto-EE | 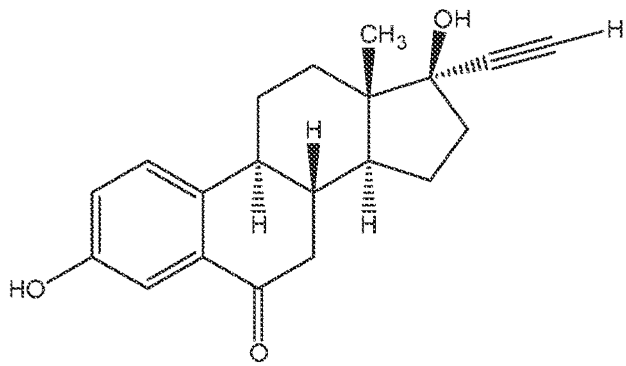 |
| 17β-estradiol | 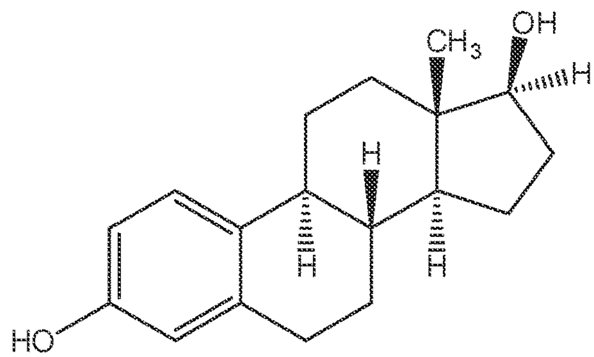 |
| 3-enolacetate-NES | 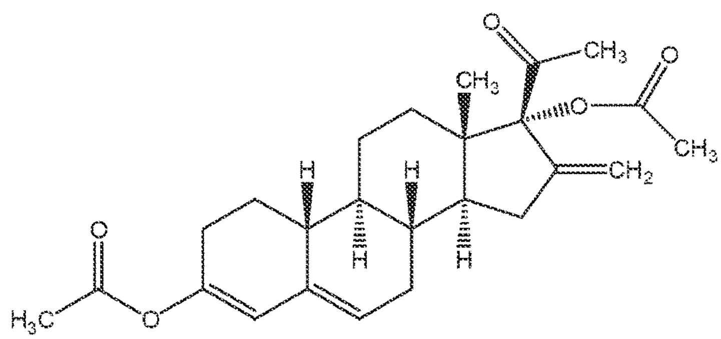 |
| 3-Methoxy-NES | 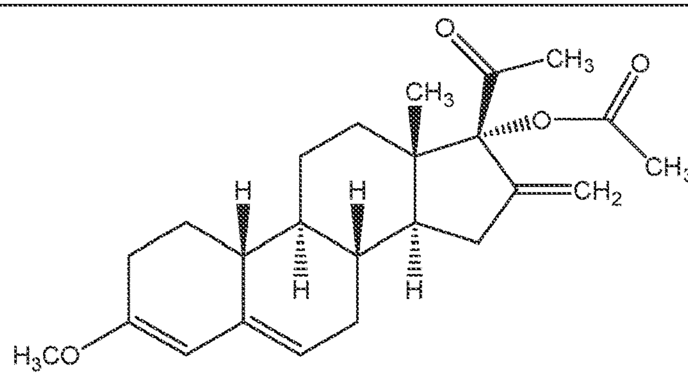 |

FIG. 10B

| Name | Structure |
|---|---|
| NES ST-alcohol | 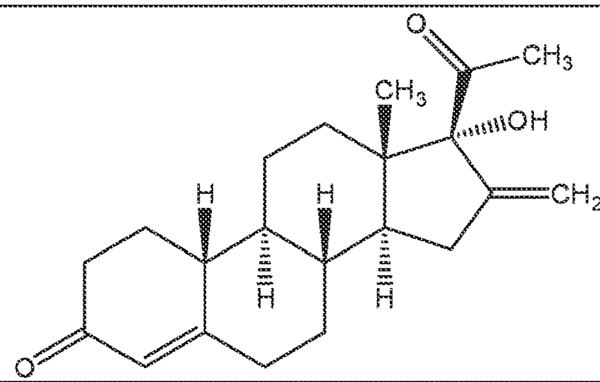 |
| NES-iso-ST-alcohol | 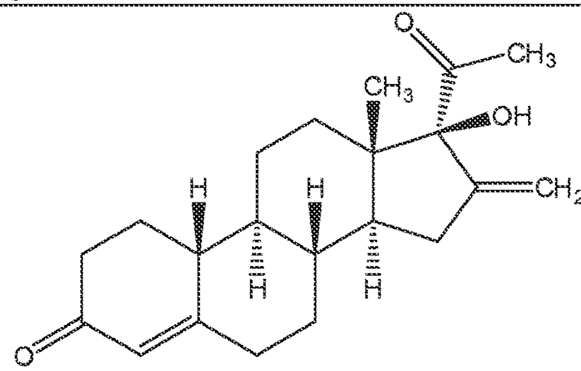 |
| 6,7-didehydro-EE | 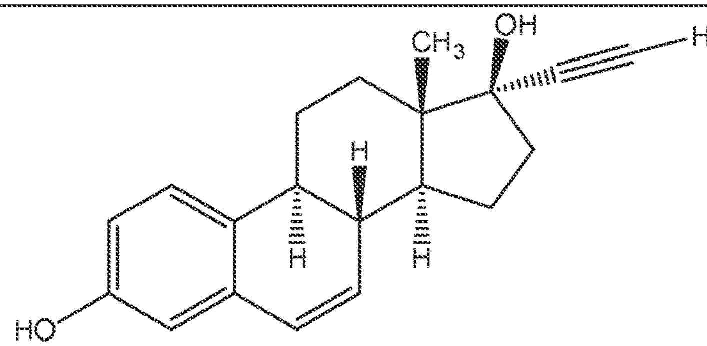 |
| 9,11-didehydro-EE | 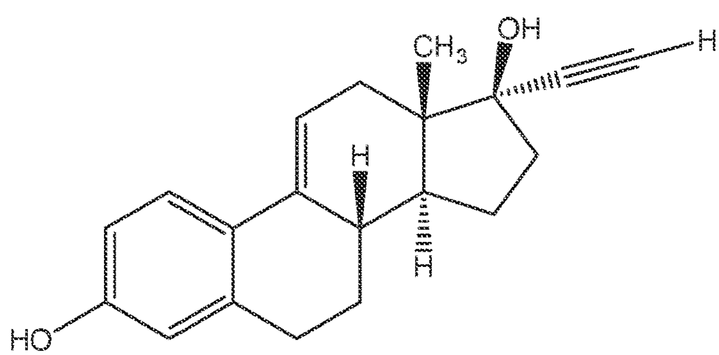 |

FIG. 10C

| Name | Structure |
|---|---|
| Estrone | 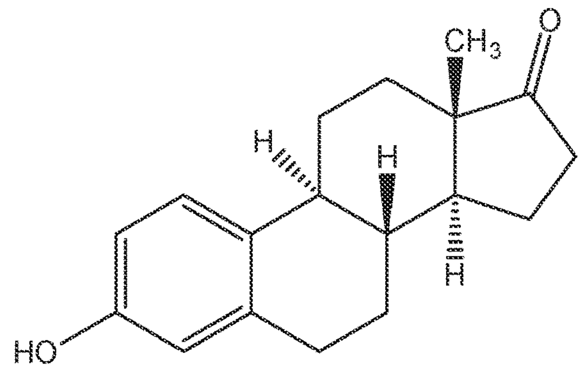 |
| Δ⁶-NES |  |
| Iso-NES | 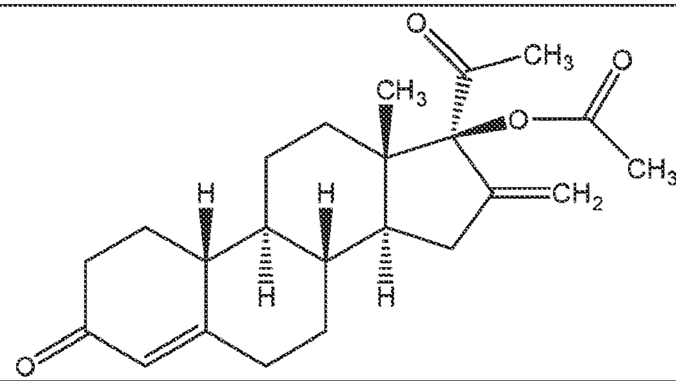 |

Mean Segesterone Acetate and Ethinyl Estradiol Serum Concentrations Delivered by ANNOVERA™ Over 21 Days of Dosing for Cycles 1, 3, and 13

Mean Segesterone Acetate and Ethinyl Estradiol Serum Concentrations Delivered by ANNOVERA™ Over the First 48 Hours of Dosing for Cycles 1, 3, and 13

| Schedule | | |
|---|---|---|
| Product-Use Cycle 1 | Put vaginal system in → (vaginal system change day) | Day 1 | Weeks 1, 2, and 3; Days 1-21 |
| | Take vaginal system out → (vaginal system change day) | Day 22 | Week 4 Days 22-28 |
| Product-Use Cycle 2 (repeat for Product-Use Cycles 3-13) | Put vaginal system in → (vaginal system change day) | Day 1 | Weeks 1, 2, and 3; Days 1-21 |
| | Take vaginal system out → (vaginal system change day) | Day 22 | Week 4 Days 22-28 |

FIG. 13

SYSTEM FOR PROVIDING BIRTH CONTROL

FIELD

The present disclosure relates to a vaginal system for preventing pregnancy comprised of a progestin, such as segesterone acetate, and an estrogen, such as ethinyl estradiol, that is configured for thirteen 28-day product-use cycles.

BACKGROUND

The use of oral contraception is widespread in the female population. But the need to remember a daily pill and the inconvenience of having to obtain frequent refills can reduce compliance, jeopardizing its effectiveness.

The use of subcutaneous upper arm implants and intrauterine devices (IUDs) as a means of administering contraception is seen as a way of overcoming these drawbacks as they remain effective for more than one year. These devices, however, have their own disadvantages as insertion and removal of implants and IUDs require a medical professional, such as a doctor, nurse, or physician's assistant.

Intravaginal rings are annularly shaped articles containing pharmaceutical agents (drugs) that can be introduced into the vagina in a simple manner without medical assistance. For example, NUVARING® (etonogestrel/ethinyl estradiol vaginal ring) was designed to be used during single 28-day cycles. NUVARING® is discarded at 21 days and a new ring inserted at the beginning of the next 28-day cycle. While the product provides a month of contraception without having to remember a daily pill, there is still a need for regular prescription refills during the year.

SUMMARY

In a first aspect, the present disclosure provides a reusable vaginal system for preventing pregnancy comprising: a silicone elastomer ring body, and two cores, the cores containing, in total, approximately 103 mg of segesterone acetate, and approximately 17.4 mg of ethinyl estradiol;
  wherein the system is configured to release an approximate average of 0.15 mg/day of segesterone acetate and an approximate average of 0.013 mg/day of ethinyl estradiol, or bioequivalent amounts thereof, for up to 13 cycles of 21 days each; and
  wherein approximately 80% to approximately 90% of the ethinyl estradiol is recoverable from the system after approximately 18 months of storage at 25° C. and 60% relative humidity.

In a first embodiment of the first aspect, the system is configured to release an approximate average of 0.15 mg/day of segesterone acetate and an approximate average of 0.013 mg/day of ethinyl estradiol, or bioequivalent amounts thereof, for up to 13 cycles of 21 days each in the vagina of a female subject in need thereof.

In a second embodiment of the first aspect, one of the two cores contains segesterone acetate and the other contains segesterone acetate and ethinyl estradiol. In a third embodiment of the first aspect, the core that contains segesterone acetate and ethinyl estradiol is cured at a temperature from approximately 60° C. to approximately 90° C. In a fourth embodiment of the first aspect, the core that contains segesterone acetate and ethinyl estradiol is cured at a relative humidity of approximately 1% to approximately 2%. In a fifth embodiment of the first aspect, the core that contains segesterone acetate and ethinyl estradiol is aged for at least 30 days before being assembled into the ring body.

In a sixth embodiment of the first aspect, the silicone elastomer has a hydride/vinyl ratio from approximately 1:1 to approximately 1.3:1 before curing.

In a seventh embodiment of the first aspect, the silicone elastomer ring body has a platinum concentration of approximately 3 ppm to approximately 10 ppm. In an eighth embodiment of the first aspect, the silicone elastomer ring body has a platinum concentration of approximately 4 ppm to approximately 9 ppm. In a ninth embodiment of the first aspect, the silicone elastomer ring body has a platinum concentration of approximately 5 ppm to approximately 8 ppm.

In a second aspect, the present disclosure provides a multi-component 13-cycle vaginal system for preventing pregnancy, the system comprising:
  a silicone elastomer ring body adapted to receive first and second drug-containing cores, the ring body comprising a silicone elastomer which has a platinum concentration of approximately 3 ppm to approximately 10 ppm;
  first and second cores comprising, in total, approximately 103 mg of segesterone acetate and approximately 17.4 mg of ethinyl estradiol;
  wherein the system is configured to release an approximate average of 0.15 mg/day of segesterone acetate and an approximate average of 0.013 mg/day of ethinyl estradiol, or a bioequivalent amount of either or both, for up to 13 cycles of 21 days each; and
  wherein approximately 80% to approximately 90% of the ethinyl estradiol is recoverable from the system after approximately 18 months of storage at 25° C. and 60% relative humidity.

In a first embodiment of the second aspect, the system is configured to release an approximate average of 0.15 mg/day of segesterone acetate and an approximate average of 0.013 mg/day of ethinyl estradiol, or bioequivalent amounts thereof, for up to 13 cycles of 21 days each in the vagina of a female subject in need thereof.

In a second embodiment of the second aspect, the silicone elastomer ring body has a platinum concentration of approximately 4 ppm to approximately 9 ppm. In a third embodiment of the second aspect, the silicone elastomer ring body has a platinum concentration of approximately 5 ppm to approximately 8 ppm.

In a fourth embodiment of the second aspect, the silicone elastomer has a hydride/vinyl ratio from approximately 1:1 to approximately 1.3:1 before curing.

In a fifth embodiment of the second aspect, one of the two cores contains segesterone acetate and the other contains segesterone acetate and ethinyl estradiol. In a sixth embodiment of the second aspect, the core that contains segesterone acetate and ethinyl estradiol is cured at a temperature from approximately 60° C. to approximately 90° C. In a seventh embodiment of the second aspect, the core that contains segesterone acetate and ethinyl estradiol is cured at a relative humidity of approximately 1% to approximately 2%. In an eighth embodiment of the second aspect, the core that contains segesterone acetate and ethinyl estradiol is aged for at least 30 days before being assembled into the ring body.

In a third aspect, the present disclosure provides a multi-component vaginal system for preventing pregnancy, the system comprising:
  a silicone elastomer ring body adapted to receive first and second drug-containing cores, the ring body comprising a silicone elastomer having a hydride/vinyl ratio from approximately 1:1 to approximately 1.3:1 before curing and a platinum concentration of approximately 3 ppm to approximately 10 ppm;

first and second cores comprising, in total, approximately 103 mg of segesterone acetate and approximately 17.4 mg of ethinyl estradiol;

wherein the system is configured to release an approximate average of 0.15 mg/day of segesterone acetate and an approximate average of 0.013 mg/day of ethinyl estradiol, or a bioequivalent amount of either or both, for up to 13 cycles of 21 days; and wherein no more than approximately 10% to approximately 20% of the ethinyl estradiol undergoes hydrosilylation with unreacted hydrosilane in the ring body after approximately 18 months of storage at 25° C. and 60% relative humidity.

In a first embodiment of the third aspect, the system is configured to release an approximate average of 0.15 mg/day of segesterone acetate and an approximate average of 0.013 mg/day of ethinyl estradiol, or bioequivalent amounts thereof, for up to 13 cycles of 21 days each in the vagina of a female subject in need thereof.

In a second embodiment of the third aspect, the silicone elastomer ring body has a platinum concentration of approximately 4 ppm to approximately 9 ppm. In a third embodiment of the third aspect, the silicone elastomer ring body has a platinum concentration of approximately 5 ppm to approximately 8 ppm.

In a fourth embodiment of the third aspect, one of the two cores contains segesterone acetate and the other contains segesterone acetate and ethinyl estradiol. In a fifth embodiment of the third aspect, the core that contains segesterone acetate and ethinyl estradiol is cured at a temperature from approximately 60° C. to approximately 90° C. In a sixth embodiment of the third aspect, the core that contains segesterone acetate and ethinyl estradiol is cured at a relative humidity of approximately 1% to approximately 2%. In a seventh embodiment of the third aspect, the core that contains segesterone acetate and ethinyl estradiol is aged for at least 30 days before being assembled into the ring body.

In a fourth aspect, the present disclosure provides a reusable 13-cycle vaginal system for preventing pregnancy comprising: a silicone elastomer ring body, and two drug-containing cores, each core comprising segesterone acetate, ethinyl estradiol, or a combination thereof;

the silicone elastomer ring body having a shore A hardness of approximately 25 to approximately 30, a mean fatigue parallel to the cores of approximately 95% and a mean fatigue perpendicular to the cores of approximately 98%;

wherein the system is configured to release an approximate average of 0.15 mg/day of segesterone acetate and an approximate average of 0.013 mg/day of ethinyl estradiol, or a bioequivalent amount of either or both, for up to 13 cycles of 21 days each; and wherein approximately 80% to approximately 90% of the ethinyl estradiol is recoverable from the system after approximately 18 months of storage at 25° C. and 60% relative humidity.

In a first embodiment of the fourth aspect, the system is configured to release an approximate average of 0.15 mg/day of segesterone acetate and an approximate average of 0.013 mg/day of ethinyl estradiol, or bioequivalent amounts thereof, for up to 13 cycles of 21 days each in the vagina of a female subject in need thereof.

In a second embodiment of the fourth aspect, the silicone elastomer ring body has a mean fatigue parallel to the cores of approximately 95%. In a third embodiment of the fourth aspect, the silicone elastomer ring body has a mean fatigue perpendicular to the cores of approximately 98%.

In a fourth embodiment of the fourth aspect, the silicone elastomer ring body has a platinum concentration of approximately 3 ppm to approximately 10 ppm. In a fifth embodiment of the fourth aspect, the silicone elastomer ring body has a platinum concentration of approximately 4 ppm to approximately 9 ppm. In a sixth embodiment of the fourth aspect, the silicone elastomer ring body has a platinum concentration of approximately 5 ppm to approximately 8 ppm.

In a seventh embodiment of the fourth aspect, the silicone elastomer ring body has a hydride/vinyl ratio from approximately 1:1 to approximately 1.3:1 before curing.

In a fifth aspect, the present disclosure provides a multi-component 13-cycle vaginal system for preventing pregnancy, the system comprising:

a silicone elastomer ring body comprising a silicone elastomer which has a hydride/vinyl ratio from approximately 1:1 to approximately 1.3:1 before curing and a platinum concentration of approximately 3 ppm to approximately 10 ppm;

a first core comprising second and third silicone elastomers, the second and third silicone elastomers impregnated with a first amount of segesterone acetate particles having a particle size distribution: D90 of not more than 10 microns and a D50 of not more than 5 microns;

a second core comprising a fourth silicone elastomer, the fourth silicone elastomer impregnated with a second amount of segesterone acetate particles and an amount of ethinyl estradiol particles, wherein the ethinyl estradiol particles have a particle size distribution of 100% max 15 microns, 99% max 12.5 microns, 95% max 10 microns and max 40% less than or equal to 1.3 microns;

wherein the second, third, and fourth silicone elastomers contain in total, approximately 103 mg of segesterone acetate and approximately 17.4 mg of ethinyl estradiol;

wherein the ring system is configured to release an average of 0.15 mg/day of segesterone acetate and an average of 0.013 mg/day of ethinyl estradiol, or a bioequivalent amount of either or both, for up to 13 cycles of 21 days each; and wherein no more than approximately 10% to approximately 20% of the ethinyl estradiol undergoes hydrosilylation with the unreacted hydrosilane in the ring body after approximately 18 months of storage at 25° C. and 60% relative humidity.

In a first embodiment of the fifth aspect, the system is configured to release an approximate average of 0.15 mg/day of segesterone acetate and an approximate average of 0.013 mg/day of ethinyl estradiol, or bioequivalent amounts thereof, for up to 13 cycles of 21 days each in the vagina of a female subject in need thereof.

In a second embodiment of the fifth aspect, the silicone elastomer ring body has a platinum concentration of approximately 4 ppm to approximately 9 ppm. In a third embodiment of the fifth aspect, the silicone elastomer ring body has a platinum concentration of approximately 5 ppm to approximately 8 ppm.

In a fourth embodiment of the fifth aspect, at least 75% of the segesterone acetate comprises segesterone acetate Polymorphic form I.

In a fifth embodiment of the fifth aspect, the segesterone acetate comprises up to 25% segesterone acetate Polymorphic form II.

In a sixth embodiment of the fifth aspect, the second core is cured at a temperature from approximately 60° C. to approximately 90° C. In a seventh embodiment of the fifth aspect, the second core is cured at a relative humidity of approximately 1% to 2%. In an eighth embodiment of the fifth aspect, the second core is aged for at least 30 days before being assembled into the ring body.

In a sixth aspect, the present disclosure provides a 13-cycle vaginal system for preventing pregnancy, the ring system comprising:
 a silicone elastomer ring body;
 segesterone acetate particles having a particle size distribution: D90 of not more than 10 microns; D50 of not more than 5 microns; and a D10 of not less than 0.6 microns;
 ethinyl estradiol particles having a particle size distribution of 100% max 15 microns, 99% max 12.5 microns, 95% max 10 microns and max 40% less than or equal to 1.3 microns;
 wherein the system contains, in total, approximately 103 mg of segesterone acetate and approximately 17.4 mg of ethinyl estradiol.

In a first embodiment of the sixth aspect, at least 75% of the segesterone acetate is segesterone acetate Polymorphic form I. In a second embodiment of the sixth aspect, at least 95% of the segesterone acetate is segesterone acetate Polymorphic form I.

In a third embodiment of the sixth aspect, up to 25% of the segesterone acetate is segesterone acetate Polymorphic form II.

In another aspect, the present disclosure provides a method of birth control that uses a vaginal system compatible with male condoms made from natural rubber latex, polyisoprene, or polyurethane and is configured for thirteen 28-day cycles wherein a secondary contraception product is employed when the vaginal system is removed or expelled from the vagina for specified amounts of time within any of the product-use cycles.

In another aspect, the present disclosure provides a method of preventing pregnancy in a female of reproductive potential, the method comprising: (a) reinserting into the vagina of a subject in need thereof, a natural rubber latex compatible, polyisoprene compatible, and polyurethane compatible vaginal system configured to release an average of approximately 0.15 mg/day of segesterone acetate and an average of approximately 0.013 mg/day of ethinyl estradiol in a 21-day first period in each of thirteen 28-day product-use cycles, following removal or expulsion of the vaginal system from the female's vagina for more than two cumulative hours during any 21-day first period in any of the thirteen 28-day product-use cycles; and (b) employing a secondary contraception product that does not comprise estrogen for seven days after reinserting the vaginal system.

In certain embodiments of this aspect, the removal or expulsion of the vaginal system from the female's vagina during any 21-day first period for more than two cumulative hours occurs in two or more instances on the same day, in two or more instances on consecutive or non-consecutive days, or via a combination of occurrences on the same and different days.

In additional embodiments of this aspect the secondary contraception product is a condom. In other embodiments the secondary contraception product is a male condom. In further embodiments the secondary contraception product is a female condom. In yet further embodiments the secondary contraception product is a hormonal contraception product.

In another aspect the present disclosure provides a method of providing birth control to a female of reproductive potential, the method comprising: (a) determining that a vaginal system comprising segesterone acetate and ethinyl estradiol configured to release an average of approximately 0.15 mg/day of segesterone acetate and an average of approximately 0.013 mg/day of ethinyl estradiol in a 21-day first period in each of thirteen 28-day product-use cycles, has been removed or expelled from the female's vagina for more than two cumulative hours during the 21-day first period; (b) reinserting the vaginal system; and (c) employing a secondary contraception product that does not comprise estrogen for seven days after reinserting the vaginal system; wherein the vaginal system is compatible with male condoms comprising natural rubber latex, polyisoprene, or polyurethane.

In another aspect the present disclosure provides a method of providing birth control to a female of reproductive potential, the method comprising inserting a vaginal system configured for thirteen 28-day product-use cycles into the female's vagina, wherein the vaginal system is compatible with male condoms comprising natural rubber latex, polyisoprene, or polyurethane, and wherein the vaginal system is configured to release an average of approximately 0.15 mg/day of segesterone acetate and an average of approximately 0.013 mg/day of ethinyl estradiol in a 21-day first period in each of thirteen 28-day product-use cycles; and wherein a secondary contraception product that does not comprise estrogen is employed when the vaginal system is removed or expelled from the female's vagina for more than two cumulative hours during a first period of any one of the thirteen 28-day product-use cycles.

In certain embodiments of this aspect the first period begins with an initial insertion of the system on either day 2, 3, 4, or 5 of the female's menstrual cycle.

In other embodiments each 28-day product-use cycle further comprises a second period during which the vaginal system is outside of the female's vagina, and wherein the second period begins with removal of the vaginal system on the day after the end of the first period.

In further embodiments the vaginal system is stored at room temperature during the second period.

In additional embodiments the method further comprises reinserting the vaginal system the day after the end of the second period, wherein the reinsertion occurs at approximately the same time of day as the initial insertion in the previous product-use cycle and wherein a secondary form of contraception that does not comprise estrogen is employed for seven days from the reinsertion when the system is reinserted more than 29 days after the previous product-use cycle's initial insertion.

In another aspect the present disclosure provides a method of birth control comprising: (a) initially inserting into the vagina of a female of reproductive potential a vaginal system configured for thirteen 28-day product-use cycles, wherein the system is compatible with male condoms comprising natural rubber latex, polyisoprene, or polyurethane, and wherein the system is configured to release an average of approximately 0.15 mg/day of segesterone acetate and an average of approximately 0.013 mg/day of ethinyl estradiol in a 21-day first period in each of the thirteen 28-day product-use cycles, wherein the initial insertion occurs on either day 2, 3, 4, or 5 of the female's menstrual cycle; (b) retaining the system in the patient's vagina for the first period of 21 days starting with and including the initial insertion date of step (a), wherein if the system is removed or expelled during the first period for more than two cumulative hours a secondary contraception product that does not comprise estrogen is employed; (c) removing the vaginal system on the day following the end of the first period; (d) storing the removed vaginal system for a second period of between five and seven days including the removal date of step (c), wherein the first and second period together comprise a product-use cycle; (e) repeating steps (a)-(d) for a total of up to thirteen product-use cycles including the first product-use cycle, wherein each initial insertion of step (a) is performed at approximately the same time of day as in the previous product-use cycle and wherein during any subsequent product-use cycle if the vaginal system is initially inserted more than 29 days after the previous initial insertion of step (a) a secondary contraception product that does not comprise estrogen is employed for seven days from the vaginal system reinsertion.

In other embodiments of this aspect the removed vaginal system is stored at room temperature.

BRIEF DESCRIPTION OF THE DRAWINGS/FIGURES

FIG. 10A shows the structures of the identified NES and EE degradation products.

FIG. 10B shows the structures of the identified NES and EE degradation products.

FIG. 10C shows the structures of the identified NES and EE degradation products.

Figure 11:
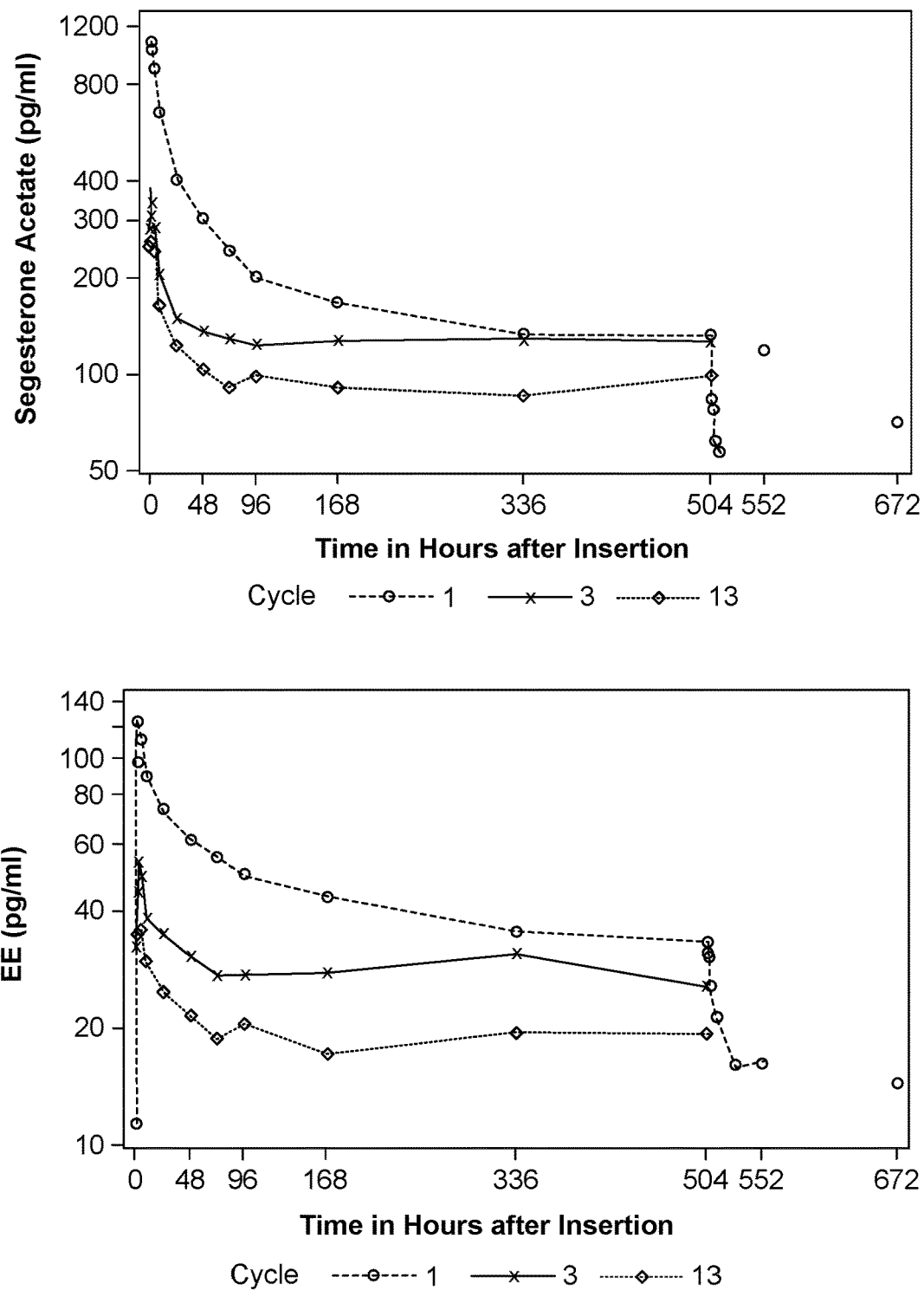

FIG. 11 depicts mean segesterone acetate and ethinyl estradiol serum concentrations delivered by the vaginal system over 21 days of dosing for cycles 1, 3, and 13.

Figure 12:
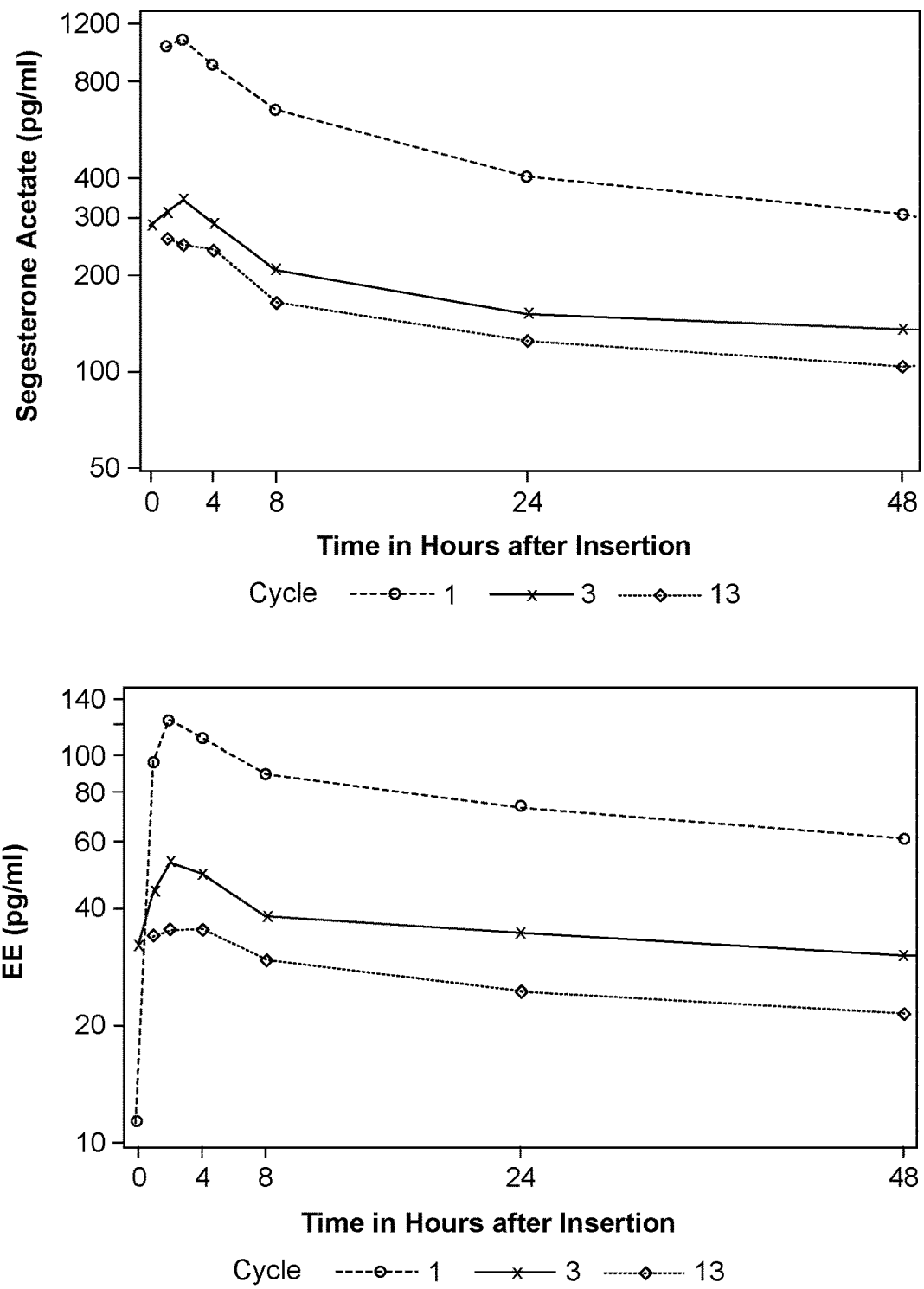

FIG. 12 depicts mean segesterone acetate and ethinyl estradiol serum concentrations delivered by the vaginal system over the first 48 hours of dosing for cycles 1, 3, and 13.

FIG. 13 is a graphical representation of a schedule for using the vaginal system described herein over 13 product-use cycles under normal use conditions.

DETAILED DESCRIPTION

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

As used herein, the term "approximately" refers to +10% of a noted value, unless otherwise specified.

The term "bioequivalent," has the meaning defined in 21 C.F.R. § 320.1(e) and refers to the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC or $C_{max}$ is within 80.00% to 125.00%.

The term "compatible" as used herein, refers to the ability of two or more items of different chemical makeup to come into repeated contact with each other over the course of an extended period, such as approximately 1 year, without a detrimental effect to any of the items coming into contact with each other over the period of time. Exemplary detrimental effects that do not occur when two or more items are compatible include, but are not limited to, a chemical reaction between the two or more items, an increase in brittleness in one or more of the items, tearing of one or more of the items, expansion or contraction of one or more of the items, breakage of one or more of the items, hardening of one or more of the items, softening of one or more of the items, erosion of one or more of the items, and/or reduced functionality of one or more of the items, such as a change in the rate of drug release from one of the items.

The phrase "two cumulative hours" as used herein, refers to multiple periods of time that together total 2 hours.

The term "day" as used herein, refers to a period of 24 hours.

The term "elongation" as used herein, is the amount of increase in length that occurs before a substance breaks under tension. The procedure used to measure elongation of the subject vaginal ring is described in Example 5 herein.

"Ethinyl estradiol" and "EE" as used herein, refer to the compound with the established name 19-nor-17α-pregna-1,3,5(10)-trien-20-yne-3,17-diol, molecular formula $C_{20}H_{24}O_2$, having the structure:

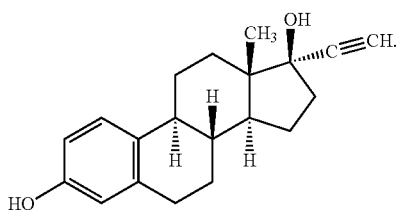

The physical form of the compound is a white to slightly yellowish-white crystalline powder. The compound is practically insoluble in water, freely soluble in alcohol, and dissolves in alkaline solution. In certain embodiments, the EE comprises a crystalline form that melts from approximately 181° C. to approximately 186° C. In some embodiments, the EE comprises a crystalline form that melts from approximately 141 to approximately 146° C.

The term "fatigue" as used herein, refers to the weakening of a material caused by repeatedly applied loads. The procedure used to measure the fatigue of the vaginal ring described in this disclosure is described in Example 6 herein.

The phrase "first period" as used herein, refers to the 21 days that the vaginal system described herein is inside of a subject's vagina during a product-use cycle.

The term "hydrosilation" as used herein, refers to the catalyzed addition of Si—H bonds across unsaturated bonds.

The phrase "initial insertion" as used herein, refers to the first insertion of the vaginal system into the vagina during a product-use cycle. In one embodiment of the present disclosure the initial insertion occurs on either day 2, 3, 4, or 5 of the female's menstrual cycle.

The terms "menstrual cycle" and "menstrual period" as used herein, refer to the process of ovulation and menstruation in women. In one embodiment of the present disclosure, day 1 is the first day of menstruation.

The phrase "natural rubber latex" as used herein, refers to the substance derived from the milky fluid obtained from plants such as the rubber tree.

The term "polyisoprene," as used herein, refers to a polymer of isoprene, the polymer having the structure:

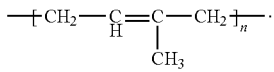

The term "polyurethane" as used herein, refers to a polymer composed of organic units joined by carbamate (urethane) links.

The phrase "product-use cycle" as used herein, refers to the combined number of days of the first period and the second period. In one embodiment of the present disclosure the product-use cycle of the vaginal system described herein is 28 days.

The terms "reinserting" and "reinsertion" as used herein, refer to any second or subsequent insertion of the vaginal system into the vagina within a given product-use cycle, and in particular, within the first period.

The term "relative humidity" as used herein, refers to the amount of water vapor present in the air, expressed as a percentage of the amount needed for saturation at the same temperature.

The term "reproductive potential" as used herein refers to the capacity for a female to produce offspring.

The phrase "room temperature" as used herein, refers to a temperature from 15° C. and 30° C.

The phrase "second period" as used herein, refers to the 5-7 days that the vaginal system is outside of a subject's vagina during a product-use cycle. The second period is a non-overlapping period immediately following the first period and is a "dose-free" interval. That is, the subject does not receive either SA or EE during this period.

The phrase "secondary contraception product" as used herein refers to a product other than the vaginal system described herein that provides birth control. In one embodiment of the present disclosure the secondary contraception product does not comprise estrogen.

"Segesterone acetate," "SA," and "NES" as used herein refer to the compound with the established name 16-methylene-17α-acetoxy-19-nor-pregn-4-ene-3,20-dione, molecular formula $C_{23}H_{30}O_4$, having the structure:

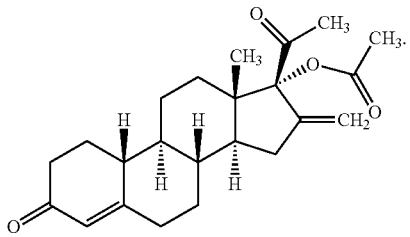

The physical form of the compound is a white, or yellowish white powder. The compound is slightly soluble in n-hexane, soluble in ethyl acetate and methanol, and freely soluble in acetone (USP classification). Segesterone acetate is sold under the trade name NESTORONE®.

The term "subject" as used herein, refers to a human female of reproductive potential.

The term "substantially pure" as used herein, refers to a polymorph of a compound which is greater than approximately 90% pure. This means that the polymorph does not contain more than approximately 10% of any other compound or any other form of the compound.

The term "tensile strength" as used herein, refers to the resistance of a substance to lengthwise stress, measured in force per unit of cross-sectional area, by the greatest load pulling in the direction of length that a given substance can bear without tearing apart. The procedure used to measure tensile strength is described in Example 5 herein.

The term "unacceptable EE burst" as used herein, refers to an EE burst of greater than or equal to approximately 0.13 mg (i.e. greater than or equal to approximately ten times the average amount of EE released per day by the vaginal system).

The term "vaginal system" as used herein, refers to a device that is inserted into the vagina and prevents pregnancy. In one embodiment of the present disclosure the vaginal system comprises a vaginal ring. In another embodiment of the present disclosure the vaginal system comprises a progestin/estrogen combined hormonal contraceptive (CHC). In another embodiment of the present disclosure the vaginal system is a segesterone acetate and ethinyl estradiol system. In another embodiment, the vaginal system is sold under the trade name ANNOVERA®.

In certain embodiments, the vaginal system of the present disclosure is a toroidal-shaped (i.e. ring-shaped), non-biodegradable, flexible, opaque white, silicone elastomer that is 56 mm in overall diameter and 8.4 mm in cross-sectional diameter. In some embodiments, the elastomer can be a methyl siloxane-based polymer. In some embodiments, the vaginal system further comprises inactive ingredients including titanium dioxide, dibutyltin dilaurate, and silicone medical adhesive.

In typical embodiments, each vaginal system is individually packaged in an aluminum pouch. Typically, the pouch consists of a laminate material comprising, from outside to inside, polyester, aluminum foil, and polyethylene. A compact case that is inert to the vaginal system can be provided for patients to store the system.

In some embodiments, the vaginal system described herein contains from approximately 90 mg to approximately 120 mg of segesterone acetate (SA). In some embodiments, the vaginal system described herein contains from approximately 95 mg to approximately 115 mg of SA. In some embodiments, the vaginal system described herein contains from approximately 100 mg to approximately 110 mg of SA. In some embodiments, the vaginal system described herein contains approximately 103 mg of SA. In some embodiments, the vaginal system described herein contains 103 mg of SA.

In some embodiments, the vaginal system described herein contains from approximately 10 mg to approximately 25 mg of ethinyl estradiol (EE). In some embodiments, the vaginal system described herein contains from approximately 15 mg to approximately 20 mg of EE. In some embodiments, the vaginal system described herein contains approximately 17.4 mg of EE. In some embodiments, the vaginal system described herein contains 17.4 mg of EE.

In some embodiments, the vaginal system described herein contains 103 mg of SA and 17.4 mg of EE. In certain embodiments, the system can release an approximate average 0.15 mg/day of SA and 0.013 mg/day of EE in the vagina over a period of 21 days of each product-use cycle for up to 13 product-use cycles (total of 273 days). Each product-use cycle is 28 days and comprises a first period of 21 days and a second period of 7 days. Typically, the vaginal system is self-inserted by the subject into the vagina for the first period and is removed for the second period. The day of the week when the vaginal system is inserted for the first time in the first period, i.e. Day 1, is the vaginal system change day. The day of the week when the vaginal system is removed for the beginning of the second period, i.e. day 22, is likewise referred to as the vaginal system change day. This cycle is shown visually in FIG. 14. Each vaginal system is designed to be used for up to 13 product-use cycles (1 year), before being discarded.

In some embodiments, the vaginal system described herein can release an approximate average of 0.15 mg/day of SA and an approximate average of 0.013 mg/day of EE, or bioequivalent amounts thereof.

Although the vaginal system provides SA and EE in the approximate rates described above, SA and EE can diffuse out of the vaginal system with release rates that vary over time. In certain embodiments, the daily in vitro release rates of SA and EE are higher during each initial 24-48 hours of use in a given product-use cycle, achieving a somewhat lower steady-state with continued use over subsequent days in each product-use cycle. Based on the residual amount of drug in vaginal systems used in clinical trials over 13 product-use cycles, a total of approximately 41.3 mg of SA and approximately 3.4 mg of EE are released over this period. Thus, approximately 60% of the SA and approximately 80% of the EE remains in the vaginal system at the end of the 13 product-use cycles. For the reasons explained later in this disclosure, it was surprising that such a greater proportional amount of EE was required for the vaginal system compared to the SA.

When used by a subject of reproductive potential, one system should be placed in the subject's vagina. In certain embodiments, and for maximum contraceptive effectiveness, the vaginal system can remain in the vagina continuously for 21 days (3 complete weeks), i.e. the first period. Upon completion of the first period, the vaginal system should be removed for the second period which, in typical embodiments, is one week. During the second period, a withdrawal bleed usually occurs. Once removed, the vaginal system should be cleaned with mild soap and warm water, patted dry with a clean cloth towel or paper towel, and placed in its case for the duration of the second period. At the end of the second period, the vaginal system should be cleaned prior to being placed back in the vagina for another first period of 21 continuous days (3 complete weeks). In preferred embodiments, this product-use cycle can be repeated and can provide contraception for 13 product-use cycles.

The vaginal system can be inserted using a variety of techniques. For example, the user can choose an insertion position that is comfortable, such as lying down, squatting, or standing. Typically, the sides of the vaginal system can be pressed together for insertion into a subject's vagina. When properly inserted, the vaginal system should be entirely in the vagina and behind the pelvic bone. The day and time of insertion should be noted so that the vaginal system can be removed 3 weeks later on the same day and at about the same time, i.e. at the end of the first period.

The system can be removed by hooking an index finger into the vaginal system inside the vagina and gently pulling the vaginal system.

After 13 product-use cycles, and because the vaginal system still contains both SA and EE, the system should be placed in the case that comes with it and disposed of at a drug take-back location, if available. If a drug take-back location is not available, it should be disposed of in the trash.
Beginning Use of the Vaginal System If hormonal birth control is not being used (and if any copper IUD has been removed), the vaginal system should be started between days 2 and 5 of the menstrual period. If menstrual periods are not regular or if the system is started more than 5 days from the start of the menstrual period, a barrier method of birth control, such as a male condom or spermicide, should be used during sexual intercourse for the first 7 days that the vaginal system is used.

If changing from a birth control pill or patch or monthly disposable contraceptive vaginal ring to the vaginal system described herein, and the previous method has been used correctly and there is no possibility of pregnancy, a change to the system described herein can occur any day of the birth control cycle without the need for backup contraception. The vaginal system described herein cannot be started any later than the start date of the next birth control pill, the application date of the next patch, or the insertion date of the next monthly disposable contraceptive vaginal ring. No more than 7 hormone-free days should occur before starting the system.

If switching from a minipill, injection, implant, or an intrauterine system (i.e., Progestin-Only Method [Progestin-only pills (POP), Progestin Injection, Progestin Implant, Progestin Intrauterine System (IUS)] to the vaginal system described herein, and there are no contraindications to the use of EE, the switch can be made from a progestin-only method to the present system. If switching from progestin-only pills, the vaginal system should start at the time the next POP pill would have been taken. If switching from an injection, the vaginal system described herein should be started at the time of the next scheduled injection. If switching from an implant or an IUS, the system should be started at the time of implant or IUS removal. In all of these cases an additional barrier method, such as a male condom or spermicide, should be used during coitus for the first 7 days of use of the system.

If there are no contraindications to the use of EE, the vaginal system described herein may be initiated for contraception within the first 5 days following a complete first trimester abortion or miscarriage without additional back-up contraception. If more than 5 days have elapsed from the first trimester abortion or miscarriage, a non-hormonal birth control method, such as male condoms or spermicide, should be used while waiting for the next menstrual period to start. The vaginal system should then be started between days 2 and 5 of the menstrual period. If the system is started more than 5 days from the start of the menstrual period, a barrier method of birth control, such as a male condom or spermicide, should be used during sexual intercourse for the first 7 days that the system is used.

The vaginal system described herein should not be started earlier than 4 weeks (28 days) after a second trimester abortion or miscarriage (after the first 12 weeks of pregnancy) due to the increased risk of thromboembolism.

The vaginal system described herein should not be started sooner than 4 weeks postpartum and should only be started in subjects who choose not to breastfeed. Prior to 4 weeks postpartum there is an increased risk of thromboembolism. If the system is started 4 or more weeks after having a baby and a menstrual period has not started, another method of birth control should be used until the system has been used for 7 days in a row. The possibility of ovulation and conception occurring should be considered prior to initiating use of the vaginal system described herein.

Breastfeeding women should not use the vaginal system described herein. Females who are breastfeeding should use other birth control methods and not use the system until after weaning.

When the vaginal system described herein is being used, regular 28-day cycles should be expected. Bleeding or spotting may occur between scheduled periods, especially during the first product-use cycle. If spotting continues for more than 7 consecutive days a health care provider should be consulted. If a period does not occur, a health care provider should be consulted. If pregnancy is confirmed by a health care provider, the vaginal system use should be discontinued. However, the system should not be removed until pregnancy is confirmed.

Deviation from Intended Use

Contraceptive efficacy of the vaginal system may be reduced if the subject deviates from the recommended use. The system should remain in the vagina for the first period, i.e. 21 days (3 weeks) and then it should be taken out of the vagina for 7 days. In a 28-day product-use cycle, comprising a first period and a second period, a deviation that involves the system being out of the vagina for less than 7 days during the second period will not increase pregnancy risk, but a deviation that involves the system being out of the vagina for more than 7 days during the second period will increase pregnancy risk and back-up contraception is recommended in these instances. Deviations from the recommended regimen may result in a new vaginal system change day.

If the vaginal system is removed too soon or is reinserted too late, the chance of getting pregnant is higher. For example, if the subject is 1 or 2 days off schedule (late) for vaginal system insertion or reinsertion, a new vaginal system-in and vaginal system-out day will need to be recorded for the remaining product-use cycles. Back-up contraception, such as condoms or spermicide, will also have to be used for the first 7 days of the new schedule. If the system is out for only 5 or 6 days, it should stay in for at least 3 weeks (21 days). It may be retained until the scheduled vaginal system-out day. If the system is reinserted after being out for more than 7 days, it should be immediately inserted and a new vaginal system in-day recorded. Condoms or spermicide should be used as back-up contraception for a period of 7 days. If the vaginal system is removed after being in for only 19 or 20 days, it should be left out for a week, then reinserted and retained to the normal vaginal system-out day, 22 or 23 days after the vaginal system was inserted or reinserted. If the system is removed after 22 or 23 days, it should be immediately removed and then reinserted 7 days later.

Although the vaginal system described herein is extremely effective, it has been surprisingly discovered that it is appropriate to use back-up or secondary contraception such as male condoms or spermicide when the vaginal system is out of the vagina for more than 2 continuous hours or more than 2 cumulative hours during the first period. In such situations back-up contraception should be used until the vaginal system has been in the vagina for 7 consecutive days.

Deviation from intended use can be intentional or unintentional. For example, the vaginal system can be removed for repositioning, to increase comfort during coitus, or for any other reason. Likewise, it can be unintentionally expelled, such as while removing a tampon, during coitus, or with straining during a bowel movement. If the vaginal system is intentionally removed or unintentionally expelled once during the 21 days of intravaginal use and is replaced within 2 hours, contraceptive efficacy should not be reduced and no back-up contraception is needed. In instances where the vaginal system is accidently or unintentionally expelled, it should be washed with mild soap and warm water, rinsed and patted dry with a clean cloth towel or paper towel, and replaced as soon as possible.

Alternatively, when the system is out of the vagina for more than 2 continuous hours or more than 2 cumulative hours during the first period, then back-up contraception, such as male condoms or spermicide, should be used until the vaginal system has been in the vagina for 7 consecutive days. The use of combined hormonal contraceptives (those containing an estrogen) for emergency contraception during use of the vaginal system described herein is not recommended.

The period of time exceeding two cumulative hours can be arrived at via a number of combinations of intentional and unintentional removals or expulsions of the vaginal system from a subject's vagina. In certain embodiments, however, the time exceeding two cumulative hours can be achieved via 2, 3, 4, 5, or more instances where the vaginal system is removed or expelled from the subject's vagina. In certain embodiments, each instance where the vaginal system is removed or expelled can take place on a different consecutive or non-consecutive day within the 21-day first period, such that the period of time exceeding two cumulative hours will only be reached after several days. In other embodiments, some instances of removal or expulsion can take place on the same day, while others take place on different consecutive or non-consecutive days within the 21-day first period. In still other embodiments, each instance where the vaginal system is removed or expelled from the subject's vagina can occur on the same day, such that the period of time greater than two cumulative hours will be reached in a single day. In each case, however, the period of time greater than two cumulative hours will be reached via two or more instances where the vaginal system is removed or expelled from the subject's vagina.

More specifically, and by way of example only, where the vaginal system is intentionally removed for 90 minutes on a first day during the first period, and unintentionally removed or expelled for 90 minutes on a second consecutive or non-consecutive day during the first period, (total cumulative time out during the first period=3.0 hours), back-up contraception should be used for seven consecutive days following reinsertion of the system after the second 90 minute removal. The preceding example is meant as an example only and many other possible combinations of intentional and unintentional vaginal system removal during the first period, each for varying durations of time, are possible and considered to be within the scope of this disclosure.

Monitoring deviation and determining whether the vaginal system has been removed or expelled from the vagina for more than two cumulative hours during any first period can be performed in numerous ways. For instance, the subject using the vaginal system can keep a journal (either in paper or electronic format) to monitor the total time that the vaginal system has been out of the body during any of the 21-day first periods. Alternatively, the subject can keep track of the cumulative time out of the body during any of the first periods mentally. Other methods of keeping track of the vaginal system's time out of the vagina and determining whether the vaginal system has been removed or expelled for more than two cumulative hours are known and within the skill of the ordinarily skilled artisan in view of this disclosure.

Despite the need for secondary or back-up contraception when the vaginal system has been removed or expelled for more than two cumulative hours during the first period, it has further been surprisingly discovered that the vaginal system is compatible with condoms (male or female) made from natural rubber latex, polyurethane, and polyisoprene. That is, when the vaginal system is repeatedly exposed to a condom comprising the various polymers noted above over one or more of the thirteen product-use cycles, there is no concern that the system's efficacy will decrease as a result of this exposure, or conversely, that the system will have a negative impact on the condom. More specifically, contacting the vaginal system with one or more condoms over a product-use cycle will not cause or increase oxidative degradation of the vaginal system or the condom, cause or increase thermal degradation of the vaginal system or the condom, increase or decrease drug delivery rates from the vaginal system, cause or increase hydrolysis in the vaginal system or condom, or otherwise cause an unwanted reaction or side effect as a result of the interaction.

This compatibility is advantageous not only when using condoms as a secondary/backup form of birth control when needed, but also when using condoms as a means to prevent the transmission of sexually transmitted infections because the vaginal system described herein does not protect against HIV-infection (AIDS) and other sexually transmitted infections.

Prolonged Vaginal System Free Interval

If the Vaginal System Free Interval is prolonged, the possibility of pregnancy should be considered and the female should use back-up contraception, such as male condoms or spermicide, during coitus until the vaginal system has been in the vagina for 7 consecutive days. The use of combined hormonal contraceptives (those containing an estrogen) for emergency contraception during use of the vaginal system described herein is not recommended.

Prolonged Use of the System

If the vaginal system is left in the vagina for more than 21 days, it should be removed for 7 days and then reinserted for 21 days to resume a 21/7 schedule.

The vaginal system described herein has not been adequately evaluated in females with a body mass index of >29 kg/m2. This subpopulation was excluded from the clinical trials after two venous thromboembolisms (VTEs) occurred in this group. Higher body weight associates with lower systemic exposure of SA and EE. In a PK study conducted in 18 females with BMI<25 (16.89-24.34) kg/m$^2$ and 21 females with BMI>25 (25.15-37.46) kg/m$^2$, up to 16% and 33% decreases in the systemic exposure ($AUC_{0-21day}$) of SA and EE, respectively, were observed between the two BMI groups.

The vaginal system described herein is contraindicated for females with a high risk of arterial or venous thrombotic diseases. Examples include females over the age of 35 who smoke, females who have or have a history of deep vein thrombosis or pulmonary embolism, females who have cerebrovascular disease, females who have coronary artery disease. In addition, the vaginal system is contraindicated in females who have thrombogenic valvular or thrombogenic rhythm disease of the heart (for example, subacute bacterial endocarditis with valvular disease, or atrial fibrillation). The vaginal system described herein is also contraindicated in females who have inherited or acquired hypercoagulopathies. The system should be discontinued immediately if there is unexplained loss of vision, proptosis, diplopia, papilledema, or retinal vascular lesions and evaluate for retinal vein thrombosis.

The vaginal system described herein is contraindicated in females who have or have a history of breast cancer or other estrogen- or progestin-sensitive cancer, for females who have liver tumors, acute hepatitis, or severe (decompensated) cirrhosis, for females who have undiagnosed abnormal uterine bleeding, for females who have a hypersensitivity to any of the components of the system and for females who use Hepatitis C drug combinations containing ombitasvir/paritaprevir/ritonavir, with or without dasabuvir. The system can be restarted 2 weeks following completion of this regimen. Use of the vaginal system described herein should be stopped if a thrombotic or thromboembolic event occurs. The system should be stopped at least 4 weeks before and through 2 weeks after major surgery or other surgeries known to have an elevated risk of VTE Cardiovascular risk factors should be considered before initiating in all females, particularly those over 35 years. The system should not be used by females with uncontrolled hypertension or hypertension with vascular disease. If used in females with well-controlled hypertension, blood pressure should be monitored and use of the system discontinued if blood pressure rises significantly.

The vaginal system described herein is contraindicated in females with acute hepatitis or severe (decompensated)

cirrhosis of the liver. It should be discontinued if jaundice occurs. Acute liver test abnormalities may necessitate the discontinuation use until the liver tests return to normal and system causation has been excluded.

Glucose should be monitored in prediabetic and diabetic females taking the vaginal system described herein. An alternate contraceptive method should be considered for females with uncontrolled dyslipidemias. The system is contraindicated for females with diabetes mellitus who are over age 35, females who have diabetes mellitus with hypertension or vascular disease, who have other end-organ damage, or who have diabetes mellitus of >20 years duration. Females with hypertriglyceridemia, or a family history thereof, may be at an increased risk of pancreatitis when using the system.

Significant change in headaches should be evaluated and use of the system discontinued if indicated. The vaginal system is contraindicated in females who have headaches with focal neurological symptoms, who have migraine headaches with aura, or who are over age 35 with any migraine headaches.

The vaginal system described herein may cause irregular bleeding or amenorrhea. Bleeding/spotting that occurs during the dose-free week when the vaginal system is out is considered "scheduled" bleeding. Bleeding and/or spotting that occurs at any time while the vaginal system is inserted is considered "unscheduled" bleeding/spotting. If these persist, other causes should evaluated.

The most common adverse reactions (>5%) are headache/migraine, nausea/vomiting, vulvovaginal mycotic infection/candidiasis, abdominal pain lower/upper, dysmenorrhea, vaginal discharge, urinary tract infection, breast tenderness/pain/discomfort, bleeding irregularities including metrorrhagia, diarrhea, genital pruritus. Serious adverse reactions occurring in ≥2 subjects were: VTEs (deep venous thrombosis, cerebral vein thrombosis, pulmonary embolism); psychiatric events; drug hypersensitivity reactions; and spontaneous abortions.

Drugs or herbal products that induce certain enzymes, including CYP3A4, may decrease the effectiveness of the system or increase breakthrough bleeding. Examples of incompatible drugs and herbal products include, but are not limited to, aprepitant, barbiturates, bosentan, carbamazepine, efavirenz, felbamate, griseofulvin, oxcarbazepine, phenytoin, rifampin, rifabutin, rufinamide, topiramate, products containing St. John's wart, and certain protease inhibitors. Back-up or alternative method of contraception should be used when enzyme inducers are used with the system. Continue back-up contraception for 28 days after discontinuing the enzyme inducer to maintain contraceptive reliability.

Co-administration of atorvastatin or rosuvastatin and certain CHCs containing EE increase systemic exposure of EE by approximately 20-25%. Ascorbic acid and acetaminophen may increase plasma EE concentrations, possibly by inhibition of conjugation. CYP3A4 inhibitors such as itraconazole, voriconazole, fluconazole, grapefruit juice, or ketoconazole may increase systemic exposure of the estrogen and/or progestin component of the system.

Significant decreases in systemic exposure of estrogen and/or progestin have been noted when CHCs are co-administered with some HIV protease inhibitors (e.g., nelfinavir, ritonavir, darunavir/ritonavir, (fos)amprenavir/ritonavir, lopinavir/ritonavir, and tipranavir/ritonavir), some HCV protease inhibitors (e.g., boceprevir and telaprevir), and some non-nucleoside reverse transcriptase inhibitors (e.g., nevirapine). In contrast, significant increases in systemic exposure of estrogen and/or progestin have been noted when CHCs are co-administered with certain other HIV protease inhibitors (e.g., indinavir and atazanavir/ritonavir) and with other non-nucleoside reverse transcriptase inhibitors (e.g., etravirine).

Concomitant use of CHCs with lamotrigine may significantly decrease systemic exposure of lamotrigine due to induction of lamotrigine glucuronidation. Decreased systemic exposure of lamotrigine may reduce seizure control. Dose adjustment for lamotrigine may be necessary. Product labeling for lamotrigine should be consulted.

Concomitant use of CHCs with thyroid hormone replacement therapy or corticosteroid replacement therapy may increase systemic exposure of thyroid-binding and cortisol-binding globulin. The dose of replacement thyroid hormone or cortisol therapy may need to be increased. Approved product labeling for the therapy in use should be consulted.

Concomitant use of CHCs may decrease systemic exposure of acetaminophen, morphine, salicylic acid, and temazepam. Concomitant use with ethinyl estradiol containing CHCs may increase systemic exposure of other drugs (e.g., cyclosporine, prednisolone, theophylline, tizanidine, and voriconazole). The dosage of drugs that can be affected by this interaction may need to be increased or decreased. The approved product labeling for the concomitantly used drug should be consulted.

In a drug-drug interaction study with the vaginal system described herein and the concurrent use of three different formulations of vaginal miconazole, the use of water-based vaginal miconazole cream resulted in no change in exposure to EE or SA from the vaginal system. However, the use of either the 1 day or the 3-day oil-based miconazole suppository was associated with an overall increase in exposure up to 67% for EE and 32% for SA. Considering the potential long-term effect on vaginal system performance, concurrent use of oil-based vaginal suppositories should not occur with the system's use. If there is a need to treat a vaginal condition, water-based vaginal cream or oral therapy may be used concurrently with the vaginal system.

Water-based vaginal lubricants have no effect on the vaginal system described herein; however, oil-based (including silicone-based) vaginal lubricants will alter the vaginal system and/or exposure to EE and SA and should not be used.

The effect of tampon use on the systemic exposure of SA and EE from the vaginal system described herein has not been studied.

The use of contraceptive steroids may influence the results of certain laboratory tests, such as coagulation factors, lipids, glucose tolerance, and binding proteins.

Females with a history of depression should be monitored and the system should be discontinued if depression recurs to a serious degree.

The estrogen component of the vaginal system described herein may raise the serum concentrations of thyroxine-binding globulin, sex hormone-binding globulin, and cortisol-binding globulin. The dose of replacement thyroid hormone or cortisol therapy may need to be increased.

In females with hereditary angioedema, exogenous estrogens may induce or exacerbate symptoms of angioedema.

Chloasma may occur with use of the vaginal system described herein, especially in females with a history of chloasma gravidarum. Females who tend to develop chloasma should avoid exposure to the sun or ultraviolet radiation while using the system.

Cases of toxic shock syndrome (TSS) have been reported by vaginal ring users. TSS has been associated with tampons and certain barrier contraceptives, and in some TSS cases ring users were also using tampons. Causal relationship between the use of a vaginal ring and TSS has not been established. No cases of TSS occurred in clinical trials with use of the vaginal system described herein. If a female exhibits signs or symptoms of TSS, the possibility of this diagnosis should be considered and the vaginal system should be removed. Appropriate medical evaluation and treatment should be initiated.

Some females are aware of the vaginal system on occasion during the 21 days of use or during coitus, and partners may feel the vaginal system during coitus.

The vaginal system described herein may not be suitable for females with conditions that make the vagina more susceptible to vaginal irritation or ulceration. Vaginal and cervical erosion and/or ulceration has been reported in females using other contraceptive vaginal devices. In some cases, the ring adhered to vaginal tissue, which necessitated removal by a health-care provider.

Epidemiologic studies and meta-analyses have not found an increased risk of genital or nongenital birth defects (including cardiac anomalies and limb-reduction defects) following exposure to CHCs before conception or during early pregnancy. In the U.S. general population, the estimated background risk of major birth defects and miscarriage in clinically recognized pregnancies is 2-4% and 15-20%, respectively. The vaginal system described herein should be discontinued if pregnancy occurs, because there is no reason to use CHCs during pregnancy. No studies have been conducted of the use of the system in pregnant females.

No studies were conducted in subjects with renal impairment; the vaginal system described herein is not recommended in patients with renal impairment.

There have been no reports of serious ill effects from overdose of CHCs. Overdosage may cause withdrawal bleeding in females and nausea. In case of suspected overdose, all vaginal systems should be removed and symptomatic treatment given.

Carcinogenesis

In a 2-year carcinogenicity study in rats with subdermal implants releasing 40, 100, and 200 µg segesterone acetate per day (approximately 17-86 times the daily dose of segesterone acetate in females using the system based on body surface area), no drug-related increase in tumor incidence was observed. In a 2-year intravaginal carcinogenicity study in mice, segesterone acetate gel produced an increased incidence of adenocarcinoma and lobular hyperplasia in the breast at a dose of 30 mg/kg/day, approximately 10 times the systemic exposure of segesterone acetate per day in females using the system described herein based on AUC. A dose of 10 mg/kg/day in the mouse, approximately 3 times the systemic exposure of segesterone acetate per day based on AUC, did not result in carcinogenic findings. Long-term continuous administration of natural and synthetic estrogens in certain animal species increases the frequency of carcinomas of the breast, uterus, cervix, vagina, testis, and liver.

Mutagenesis

Segesterone acetate was neither mutagenic nor clastogenic in the Ames/Salmonella reverse mutation assay, the chromosomal aberration assay in Chinese hamster ovary cells, or in the in vivo mouse micronucleus test.

Impairment of Fertility

A return to fertility study was conducted with segesterone acetate in rats, using subdermal implants releasing a dose approximately 25 times the anticipated daily vaginal human dose (based on body surface area). Three months of treatment with segesterone acetate suppressed fertility, but 7 weeks after cessation of treatment, there were no adverse effects on ovulation or resulting litter parameters.

Resumption of fertility after discontinuation of the vaginal system described herein is expected. All women followed for return of fertility experienced a return of fertility by 6 months after discontinuing use of the system.

Vaginal System Structure

In general, the vaginal system described herein is an appropriately sized and shaped structure suitable for insertion to the vagina. The system typically comprises at least two parts: a ring body and one or more cores. The cores can be shaped in a way that is suitable for containment within the ring. The ring body is typically prepared from one or more polymeric materials, such as one or more silicone elastomers, and is generally adapted to receive, or to be coextruded with, at least one drug-containing core. The at least one drug-containing core can be prepared from the same or different polymeric materials as the ring body. The core can contain active ingredients, such as EE, SA, or a combination thereof, dissolved, dispersed (i.e. as a solid), or dissolved and dispersed throughout the at least one core. When combined, the ring body and at least one core provide the active ingredients to the user via a release rate sufficient to provide efficacious birth control over thirteen product-use cycles.

In some embodiments, the vaginal system of the present disclosure releases an approximate average 0.15 mg/day of SA and 0.013 mg/day of EE in the vagina over a period of 21 days of each product-use cycle for up to 13 product-use cycles (total of 273 days). In some embodiments, the system releases an approximate average 0.15 mg/day of SA and 0.013 mg/day of EE in the vagina over a period of 21 days of each product-use cycle for up to 13 product-use cycles (total of 273 days) and comprises one core. In other embodiments, the system releases an approximate average 0.15 mg/day of SA and 0.013 mg/day of EE in the vagina over a period of 21 days of each product-use cycle for up to 13 product-use cycles (total of 273 days) and comprises multiple cores. In some embodiments, the system releases an overall approximate average of 0.15 mg/day of SA and 0.03 mg/day of EE in the vagina over a period of 21 days of each product-use cycle for up to 13 product-use cycles (total of 273 days) and comprises two, three, or four cores. In certain embodiments, the system releases an approximate average 0.15 mg/day of SA and 0.013 mg/day of EE in the vagina over a period of 21 days of each product-use cycle for up to 13 product-use cycles (total of 273 days) and comprises two cores.

While the ring body can be manufactured without active agents, such as SA or EE, before a first product-use cycle, in certain embodiments, the ring body can be prepared such that it includes SA, EE, or both in addition to or instead of the cores, provided the vaginal system in its entirety releases an approximate average 0.15 mg/day of SA and 0.013 mg/day of EE in the vagina over a period of 21 days of each product-use cycle for up to 13 product-use cycles (total of 273 days). It is understood, however, that when the ring body is manufactured without active agents, either active agent or both active agents can diffuse from the cores into the ring body before the first product-use cycle.

In certain embodiments, the vaginal system of the present disclosure is ring-shaped, having an overall (exterior) diameter, an interior diameter, and a cross-sectional diameter. In some embodiments, the ring has an overall (exterior) diameter of from approximately 40 mm to approximately 70 mm. In other embodiments, the ring has an overall diameter of from approximately 45 mm to approximately 65 mm. In other embodiments, the ring an overall diameter of from approximately 50 mm to approximately 60 mm. In other embodiments, the ring has an overall diameter of from approximately 53 mm to approximately 59 mm. In some embodiments, the ring has an overall diameter of approximately 56 mm.

In certain embodiments, the ring has an interior diameter of from approximately 25 mm to approximately 55 mm. In other embodiments, the ring has an interior diameter of from approximately 30 mm to approximately 50 mm. In other embodiments, the ring has an interior diameter of from approximately 35 mm to approximately 45 mm. In some embodiments, the ring has an interior diameter of approximately 40 mm.

In certain embodiments, the vaginal system of the present disclosure is ring-shaped and has a cross-sectional diameter of from approximately 3 mm to approximately 10 mm. In other embodiments, the ring has a cross-sectional diameter of from approximately 3.5 mm to approximately 9.5 mm. In other embodiments, the ring has a cross-sectional diameter of from approximately 4 mm to approximately 9 mm. In other embodiments, the ring has a cross-sectional diameter of from approximately 5 to approximately 9 mm. In other embodiments, the ring has a cross-sectional diameter of from approximately 6 to approximately 9 mm. In other embodiments, the ring has a cross-sectional diameter of from approximately 7 to approximately 9 mm. In other embodiments, the ring has a cross-sectional diameter of from approximately 8 to approximately 9 mm. In some embodiments, the ring has a cross-sectional diameter of approximately 8.4 mm.

Sizing of the vaginal system is an important component in system design. As the system is inserted into a woman's vagina, the vaginal system can neither be too large nor too small to make insertion and/or retrieval more difficult. Similarly, the cross-sectional diameter of the vaginal system is another design component that can be tailored to provide optimal drug delivery and comfort so that the system is not considered aesthetically "bulky" or sensed within the vagina by the woman.

The vaginal system typically adopts the shape of the ring body such that, and by way of example only, when the ring body is ring-shaped, the vaginal system is ring shaped. Although the vaginal system can be ring-shaped, in some embodiments, the vaginal system can be an elliptic or oblong torus, a bohemian dome, lemon shaped, an "eight surface," an ellipsoid, a heart surface, a sphere, a spheroid, or any other shape suitable for insertion into the subject's vagina. In some embodiments, the vaginal system can be circular or spherical. In some embodiments, the vaginal system can be in the shape of a polygon. In some embodiments, the vaginal system can be rectangular, triangular, hexagonal, petagonal, rhomboid, triangular prism, or spherical. Any shape that is appropriate for insertion into a vagina to provide maximal comfort to the user without deviating from the teaching provided in this disclosure can be selected or used.

Regardless of its shape, and in certain embodiments, the vaginal system comprises one or more channels adapted to receive at least one core. When the ring body comprises more than one core, the channels adapted to receive the cores can be on opposing sides of the ring body. In other embodiments, the channels adapted to receive the cores are in closer to proximity to each other. In some embodiments, the channels adapted to receive the cores are adjacent to each other within the ring body. In some embodiments, the channels adapted to receive the cores abut one another. In some embodiments, the channels adapted to receive the cores are both situated in the same half of the ring body.

The release rate of the agent or agents contained within cores is affected by the length of the path the agent or agents must diffuse through to exit the system into the subject. For example, a shorter diffusion path within the ring body can provide an increased release rate, while a longer diffusion path can provide a decreased release rate. As such, the amount of active agent or agents contained within the cores must be balanced against diffusion path length, among other considerations. In some embodiments, channels adapted to receive the cores have a length of from approximately 10 mm to approximately 40 mm. In other embodiments, channels adapted to receive the cores have a length of from approximately 15 mm to approximately 35 mm. In other embodiments, channels adapted to receive the cores have a length of from approximately 20 mm to approximately 35 mm. In other embodiments, channels adapted to receive the cores have a length of from approximately 25 mm to approximately 30 mm. In other embodiments, the channels adapted to receive the cores have a length of approximately 27 mm.

The channel or channels adapted to receive the at least one core can be any appropriate shape. For example, in some embodiments, the channel or channels adapted to receive the core(s) can be a bore, such as a cylindrical bore adapted to receive an appropriately shaped cylindrical or spherical core. In other embodiments, the channel or channels can be adapted to receive a core or cores shaped like a rectangular prism, including for example a square prism, or a core or cores shaped like a cone, a triangular prism, a triangular pyramid, a rectangular pyramid, a pentagonal prism, a hexagonal prism, a heptagonal prism, or any other three dimensional shape suitable for manufacture. In some embodiments, the channel or channels can be adapted to receive a core or cores that are disc-shaped. In certain embodiments, the channel or channels can be adapted to receive a cylindrical core or core shaped like a rectangular prism.

In some embodiments, the channel or channels adapted to receive the at least one core are adapted to receive a cylindrical core having a diameter of from approximately 1 mm to approximately 7 mm. In other embodiments, the channel or channels adapted to receive the at least one core are adapted to receive a cylindrical core having a diameter of from approximately 2 mm to approximately 6 mm. In other embodiments, the channel or channels adapted to receive the at least one core are adapted to receive a cylindrical core having a diameter of from approximately 2 mm to approximately 5 mm. In other embodiments, the channel or channels adapted to receive the at least one core are adapted to receive a cylindrical core having a diameter of from approximately 2 mm to approximately 4 mm. In other embodiments, the channel or channels adapted to receive the at least one core are adapted to receive a cylindrical core having a diameter of approximately 3 mm.

In some embodiments, the cores are coextruded with the elastomers of the ring body. In other embodiments, the cores can be extruded or formed by injection molding, allowed to cure, and the ring body elastomers extruded in a manner to encase the cores.

Figure 1A:
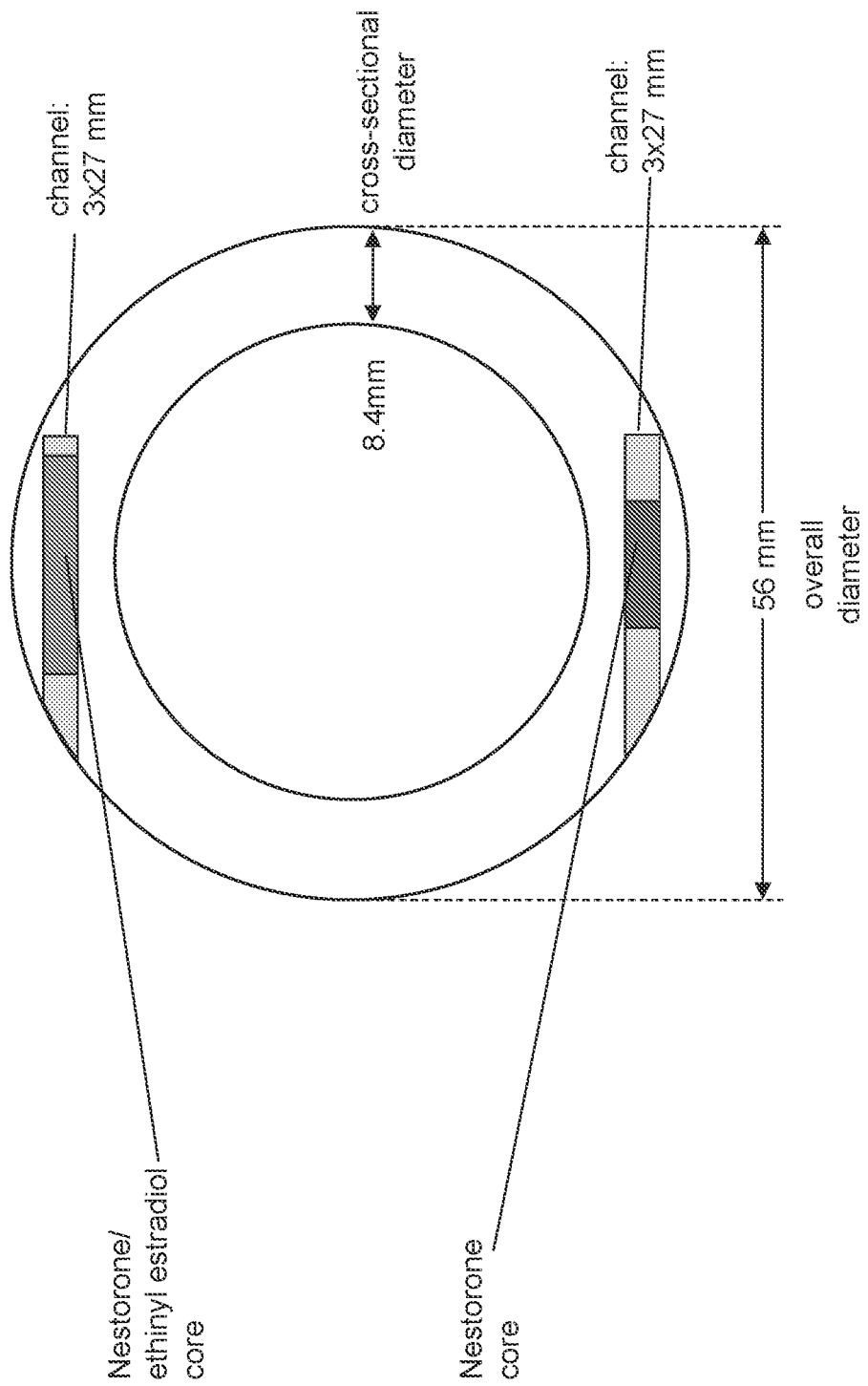
FIG. 1A and FIG. 1B are diagrams of the vaginal system disclosed herein.
Figure 1B:
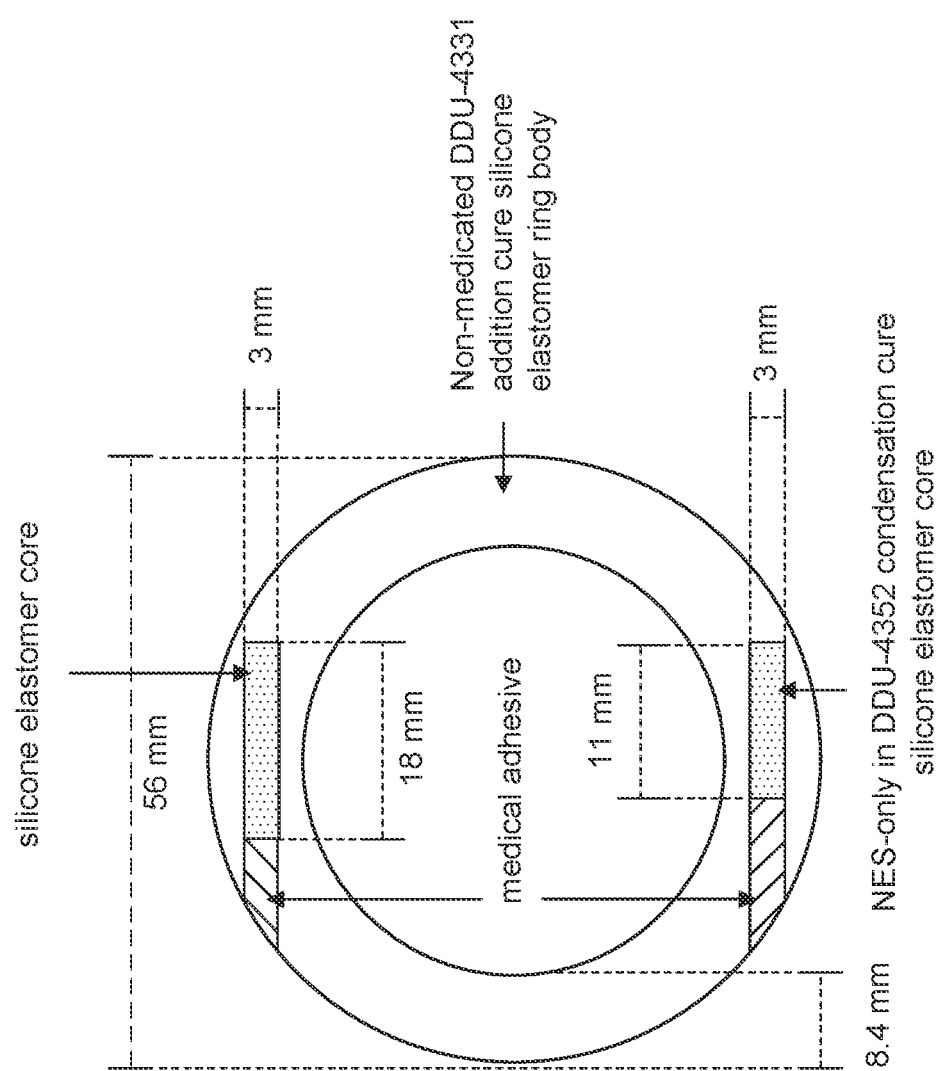

In certain embodiments, the vaginal system of the present disclosure is ring-shaped and is 56 mm in overall diameter and has a cross-sectional diameter of 8.4 mm. In some embodiments, it contains two channels, each of which is approximately 3 mm in diameter and approximately 27 mm in length, each of which is adapted to receive an appropriately sized and shaped steroid-containing core. An example of such an embodiment is shown in FIGS. 1A and 1B.

It is understood that in certain embodiments, the channels are formed in the ring at the time the ring body is prepared, either by injection molding or extrusion. In other embodiments, the channels are formed about the cores during extrusion or injection molding of the ring body.

Cores

In certain embodiments, the vaginal system contains from approximately 50 to approximately 150 mg of SA and from approximately 5 to approximately 35 mg of EE which are distributed throughout one or more cores. In certain embodiments, the vaginal system contains from approximately 75 to approximately 125 mg of SA and from approximately 10 to approximately 25 mg of EE which are distributed throughout one or more cores. In certain embodiments, the vaginal system contains from approximately 90 to approximately 115 mg of SA and from approximately 15 to approximately 20 mg of EE which are distributed throughout one or more cores. In some embodiments, the vaginal system contains approximately 103 mg of SA and approximately 17.4 mg of EE which are distributed throughout one or more cores. In certain embodiments, the vaginal system contains from approximately 50 to approximately 150 mg of SA and from approximately 5 to approximately 35 mg of EE which are distributed throughout a single core. In certain embodiments, the vaginal system contains from approximately 75 to approximately 125 mg of SA and from approximately 10 to approximately 25 mg of EE which are distributed throughout a single core. In certain embodiments, the vaginal system contains from approximately 90 to approximately 115 mg of SA and from approximately 15 to approximately 20 mg of EE which are distributed throughout a single core. In some embodiments, the vaginal system contains approximately 103 mg of SA and approximately 17.4 mg of EE which are distributed throughout a single core. In certain embodiments, the vaginal system contains from approximately 50 to approximately 150 mg of SA and from approximately 5 to approximately 35 mg of EE which are distributed throughout multiple cores. In certain embodiments, the vaginal system contains from approximately 75 to approximately 125 mg of SA and from approximately 10 to approximately 25 mg of EE which are distributed throughout multiple cores. In certain embodiments, the vaginal system contains from approximately 90 to approximately 115 mg of SA and from approximately 15 to approximately 20 mg of EE which are distributed throughout multiple cores. In some embodiments, the vaginal system contains approximately 103 mg of SA and approximately 17.4 mg of EE which are distributed throughout multiple cores. In some embodiments, the SA is distributed throughout one core and the EE is distributed throughout a separate core. In some embodiments, the SA is distributed throughout one core and the EE is distributed throughout multiple cores. In some embodiments, the SA is distributed throughout multiple cores and the EE is distributed throughout a separate core. In certain embodiments, the vaginal system contains from approximately 50 to approximately 150 mg of SA and from approximately 5 to approximately 35 mg of EE which are distributed in two or more cores, i.e. each core in the system contains both SA and EE. In certain embodiments, the vaginal system contains from approximately 75 to approximately 125 mg of SA and from approximately 10 to approximately 25 mg of EE which are distributed in two or more cores, i.e. each core in the system contains both SA and EE. In certain embodiments, the vaginal system contains from approximately 90 to approximately 115 mg of SA and from approximately 15 to approximately 25 mg of EE which are distributed in two or more cores, i.e. each core in the system contains both SA and EE. In yet another embodiment, the vaginal system contains approximately 103 mg of SA and approximately 17.4 mg of EE which are each distributed in two or more cores, i.e. each core in the system contains both SA and EE.

In a particular embodiment, the vaginal system comprises two cores that collectively contain 103 mg of SA and 17.4 mg of EE. In one such embodiment, one core contains 17.4 mg of EE and a portion of the SA drug load. The other core, in this embodiment, contains the remainder of the SA drug load. Of course, both cores can contain both actives. In some embodiments, the EE drug load is contained in a first core and the SA drug load is split amongst two or more cores.

In some embodiments, the vaginal system contains approximately 103 mg of SA distributed throughout two cores and approximately 17.4 mg of EE distributed throughout only one of the two cores, such that one core contains only SA, while the other core contains both SA and EE. In certain embodiments, the SA is distributed between the two cores in a ratio from approximately 90:10 to approximately 10:90. In other embodiments, the SA is distributed between the two cores in a ratio from approximately 80:20 to approximately 20:80. In other embodiments, the SA is distributed between the two cores in a ratio from approximately 70:30 to approximately 30:70. In other embodiments, the SA is distributed between the two cores in a ratio from approximately 60:40 to approximately 40:60. In other embodiments, the SA is distributed between the two cores in approximately a 50:50 ratio. In certain embodiments, the SA is distributed between the two cores in a ratio of from approximately 55:45 to approximately 45:55. In some embodiments, the SA is distributed between the two cores in approximately a 55:45 ratio.

In typical embodiments, the EE is present in one core and is substantially or completely absent from the second core. In other embodiments, however, the EE is distributed between the two cores in a ratio from approximately 99:1 to approximately 1:99. In other embodiments, the EE is distributed between the two cores in a ratio from approximately 95:5 to approximately 5:95. In certain embodiments, the EE is distributed between the two cores in a ratio from approximately 90:10 to approximately 10:90. In other embodiments, the EE is distributed between the two cores in a ratio from approximately 80:20 to approximately 20:80. In other embodiments, the EE is distributed between the two cores in a ratio from approximately 70:30 to approximately 30:70. In other embodiments, the EE is distributed between the two cores in a ratio from approximately 60:40 to approximately 40:60. In other embodiments, the EE is distributed between the two cores in approximately a 50:50 ratio.

In some embodiments, the vaginal system comprises a first core which contains from approximately 40% to approximately 60% SA by mass. In some embodiments, the first core contains from approximately 45% to approximately 55% SA by mass. In certain embodiments, the first core contains approximately 50% SA by mass.

In some embodiments, the first core is from approximately 1 mm to approximately 5 mm in diameter. In some embodiments, the first core is from approximately 2 mm to approximately 4 mm in diameter. In some embodiments, the first core is approximately 3 mm in diameter. In certain embodiments, the first core is from approximately 9 mm to approximately 13 mm in length. In certain embodiments, the first core is from approximately 10 mm to approximately 12 mm in length. In some embodiments, the first core is approximately 11 mm in length.

In some embodiments, the vaginal system comprises a second core which contains from approximately 30% to approximately 50% SA by mass. In some embodiments, the second core contains from approximately 35% to approximately 45% SA by mass. In some embodiments, the second core contains approximately 40% SA by mass. In some embodiments, the second core also contains from approximately 5% to approximately 20% EE by mass. In some embodiments, the second core contains from approximately 10% to approximately 14% EE by mass. In some embodiments, the second core contains approximately 12% EE by mass. In some embodiments, the second core is from approximately 1 mm to approximately 5 mm in diameter. In some embodiments, the second core is from approximately 2 mm to approximately 4 mm in diameter. In some embodiments, the second core is approximately 3 mm in diameter. In some embodiments, the second core is from approximately 16 mm to approximately 20 mm in length. In some embodiments, the second core is from approximately 17 mm to approximately 19 mm in length. In some embodiments, the second core is approximately 18 mm in length.

In certain embodiments, the vaginal system cores comprise one or more polymers. In certain embodiments, the vaginal system cores comprise one or more polymers selected from a polystyrene, a thermoplastic polymer (including, but not limited to, poly(methyl methacrylate), acrylonitrile butadiene styrene, nylon, polylactic acid, polybenimidazole, polycarbonate, polyether sulfone, polyoxymethylene, polyetherketone, polyetherimide, polyethylene, polyphenylene oxide, polyphenylene sulfide, polypropylene, polystyrene, polyvinyl chloride, polyvinylidene fluoride, and teflon), and elastomers (including, but not limited to natural and synthetic polyisoprene, polybutadiene, chloroprene, butyl rubber (including halogenated derivatives thereof), styrene-butadiene, nitrile rubber (including halogenated derivatives thereof), ethylene/propylene rubbers (including both melt blends and reactor blends (block copolymers) of ethylene and propylene), epichlorohydrin rubber, polyacrylic rubber, a silicone elastomer, fluorosilicone rubber, a fluoroelastomer (e.g. VITON, TECNOFLON, FLUOREL, AFAS, and DAI-EL), a perfluoroelastomer, a polyether block amide, chlorosulfonated polyethylene, ethylene vinylacetate ("EVA")). In some embodiments, the cores comprise EVA. In some embodiments, the cores comprise one or more elastomers, wherein the elastomers are silicone elastomers. In some embodiments, the cores comprise a mixture of silicone and other elastomers. In some embodiments, the vaginal system cores comprise a single silicone elastomer. In other embodiments, the vaginal system cores are comprised of multiple silicone elastomers. In some embodiments, one or more of the cores comprises a single silicone elastomer and one or more of the cores comprises multiple silicone elastomers.

In some embodiments, the silicone elastomers comprise one or more agents to increase viscosity. In some embodiments, the one or more agents to increase viscosity can be diatomaceous earth, cellulose, talc, and/or silica (e.g. fumed silica or colloidal silica). In some embodiments, the agent to increase viscosity is diatomaceous earth.

In some embodiments, the vaginal system described herein comprises condensation cure silicone elastomeric cores. In some embodiments, the vaginal system comprises addition-cure silicone elastomeric cores. In some embodiments, the vaginal system comprises one or more condensation cure silicone elastomeric cores and one or more condensation cure silicone elastomeric cores.

In some embodiments, the vaginal system comprises a first core which comprises one or more condensation cure silicone elastomers. In some embodiments, the first core comprises two condensation cure silicone elastomers. In some embodiments, one or both of these condensation cure silicone elastomers can contain one or more agents to increase its viscosity. In some embodiments, the one or more agents to increase viscosity can be diatomaceous earth, cellulose, talc, and/or silica (e.g. fumed silica or colloidal silica). In some embodiments, the agent to increase viscosity is diatomaceous earth.

In some embodiments, the condensation cure silicone elastomer can be NuSil™ MED-6381. In certain embodiments, this condensation-cure silicone elastomer can be prepared from three components, "Part A," "Part B," and a tin catalyst. In some embodiments, Part A comprises >90% hydroxyl-terminated dimethylsiloxanes and dimethylsilicones (CAS No. 70131-67-8). In some embodiments, Part B comprises >90% tetrapropyl orthosilicate (CAS No. 682-01-9). In certain embodiments, the tin catalyst can be di-n-butylbutoxychlorotin, dibutyldiacetoxytin, dibutyltin dilaurate, dimethyldineodecanoatetin, dioctyldilauryltin, tetramethyltin, dioctylbis(2-ethylhexylmaleate)tin, or stannous octanoate. In some embodiments, the tin catalyst is stannous octanoate or dibutyltin dilaurate.

In certain embodiments, the condensation cure silicone elastomer can be NuSil™ MED-6382. In certain embodiments, this condensation-cure silicone elastomer can be prepared from two components, "Part A" and a tin catalyst. In some embodiments, Part A comprises siloxanes, silicones, and <1% amorphous, fumed, crystalline free silica (CAS No. 112945-52-5). In certain embodiments, the tin catalyst can be di-n-butylbutoxychlorotin, dibutyldiacetoxytin, dibutyltin dilaurate, dimethyldineodecanoatetin, dioctyldilauryltin, tetramethyltin, dioctylbis(2-ethylhexylmaleate)tin, or stannous octanoate. In some embodiments, the tin catalyst is stannous octanoate or dibutyltin dilaurate.

In further embodiments, the condensation cure silicone elastomer can be NuSil™ MED-6603 (formerly known as DDU-4352). In certain embodiments, this condensation-cure silicone elastomer can be prepared from two components, "Part A" and a tin catalyst. In some embodiments, Part A comprises siloxanes and silicones. In certain embodiments, the tin catalyst can be di-n-butylbutoxychlorotin, dibutyldiacetoxytin, dibutyltin dilaurate, dimethyldineodecanoatetin, dioctyldilauryltin, tetramethyltin, dioctylbis(2-ethylhexylmaleate)tin, or stannous octanoate. In some embodiments, the tin catalyst is stannous octanoate or dibutyltin dilaurate.

In further embodiments, the condensation cure silicone elastomer can be NuSil™ MED3-6603. In certain embodiments, this condensation-cure silicone elastomer can be prepared from three components, "Part A," "Part B," and a tin catalyst. In some embodiments, Part A comprises polydimethylsiloxane backbone. In some embodiments, Part B comprises the cross-linking agent. In certain embodiments, the tin catalyst can be di-n-butylbutoxychlorotin, dibutyldiacetoxytin, dibutyltin dilaurate, dimethyldineodecanoatetin, dioctyldilauryltin, tetramethyltin, dioctylbis(2-ethylhexylmaleate)tin, or stannous octanoate. In some embodiments, the tin catalyst is stannous octanoate or dibutyltin dilaurate.

In some embodiments, the condensation cure silicone elastomer can be NuSil™ MED-6385. In certain embodiments, this condensation-cure silicone elastomer can be prepared from two components, "Part A" and a tin catalyst. In some embodiments, Part A comprises dimethylsiloxanes, dimethylsilicones (CAS No. 70131-67-8), 20-25% diatomaceous earth (CAS No. 68855-54-9), <5% silicic acid, tetrapropyl ester (CAS No. 682-01-9), and <1% amorphous, fumed, crystalline free silica (CAS No. 112945-52-5). In certain embodiments, the tin catalyst can be di-n-butylbutoxychlorotin, dibutyldiacetoxytin, dibutyltin dilaurate, dimethyldineodecanoatetin, di-octyldilauryltin, tetramethyltin, dioctylbis(2-ethylhexylmaleate)tin, or stannous octanoate. In some embodiments, the tin catalyst is stannous octanoate or dibutyltin dilaurate.

In still further embodiments, the condensation cure silicone elastomer can be NuSil™ MED3-6385. In certain embodiments, this condensation-cure silicone elastomer can be prepared from three components, "Part A," "Part B," and a tin catalyst. In some embodiments, Part A comprises polydimethylsiloxane polymer backbone and diatomaceous earth. In some embodiments, Part B comprises the cross-linking agent. In certain embodiments, the tin catalyst can be di-n-butylbutoxychlorotin, dibutyldiacetoxytin, dibutyltin dilaurate, dimethyldineodecanoatetin, di-octyldilauryltin, tetramethyltin, dioctylbis(2-ethylhexylmaleate)tin, or stannous octanoate. In some embodiments, the tin catalyst is stannous octanoate or dibutyltin dilaurate.

Each of these polymers is commercially available and is referenced in one or more drug master files.

In certain embodiments, the first silicone elastomer of the first core is NuSil™ MED-6385. In some embodiments, the second silicone elastomer of the first core is NuSil™ MED-6603 (formerly known as DDU-4352). In some embodiments, the tin catalyst is dibutyltin dilaurate.

In certain embodiments, the first core comprises SA homogeneously dispersed or distributed in a silicone elastomer comprising at least two condensation cure silicone elastomers. In certain embodiments, the core can be prepared by combining the first silicone elastomer and the second silicone elastomer, adding the SA, and blending the resulting mixture. In certain embodiments, the SA can be added in batches. After sufficient mixing, a curing agent can be added, and the resulting mixture can be blended further. In some embodiments, the curing agent can be a tin catalyst. In certain embodiments, the tin catalyst can be di-n-butylbutoxychlorotin, dibutyldiacetoxytin, dibutyltin dilaurate, dimethyldineodecanoatetin, di-octyldilauryltin, tetramethyltin, dioctylbis(2-ethylhexylmaleate)tin, or stannous octanoate. In some embodiments, the tin catalyst is stannous octanoate or dibutyltin dilaurate. In some embodiments, the curing agent can be dibutyltin dilaurate. In some embodiments, the curing agent is NuSil™ MED-6603 Part B. In some embodiments, the blended mixture, also referred to as a pre-core mixture, can be shaped into a string and be subjected to curing conditions.

In certain embodiments, the pre-core mixture can be shaped into strings by injection molding. In some embodiments, the pre-core mixture can be shaped into strings by extrusion. In certain embodiments, the strings can be cured at a temperature of from approximately room temperature to approximately 140° C. In some embodiments, the strings can be cured at a temperature of from approximately 40° C. to approximately 135° C. In certain embodiments, the strings can be cured at a temperature of from approximately 50° C. to approximately 130° C. In some embodiments, the strings can be cured at a temperature of from approximately 55° C. to approximately 125° C. In some embodiments, the strings can be cured at a temperature of from approximately 60° C. to approximately 120° C.

In some embodiments, the amount of time that the strings are cured increases with decreasing curing temperature. In certain embodiments, the strings can be cured for from approximately 10 minutes to approximately 70 minutes. In certain embodiments, the strings can be cured for from approximately 20 minutes to approximately 60 minutes. In some embodiments, the strings can be cured for from approximately 25 minutes to approximately 50 minutes. In some embodiments, the strings can be cured for from approximately 30 minutes to approximately 45 minutes. In some embodiments, the strings can be cured for approximately 30 minutes. In some embodiments, the strings can be cured for approximately 45 minutes. In some embodiments, the strings can be cured at approximately 120° C. for approximately 30 minutes. In some embodiments, the strings can be cured at approximately 60° C. for approximately 45 minutes.

In some embodiments, the cured product can be post-cured at room temperature for at least 2 days. In some embodiments, the cured product can be post-cured at room temperature for at least 3 days. In some embodiments, the cured product can be post-cured at room temperature for at least 4 days. In some embodiments, the cured product can be post-cured at room temperature for at least 5 days. In some embodiments, the cured product can be post-cured at room temperature for at least 6 days. In some embodiments, the cured product can be post-cured at room temperature for at least 7 days. In some embodiments, the cured product is post-cured at room temperature for at least 8 days. In some embodiments, the cured product can be post-cured at room temperature for at least 9 days. In some embodiments, the cured product can be post-cured at room temperature for at least 10 days.

In certain embodiments, the strings can be cut after post-curing to provide cores suitable for providing the desired SA and EE release rates as disclosed herein. As core length and diameter can affect the release rate of the agents, the amount of a particular agent added to a particular core needs to be balanced against the length and diameter of that core to ensure that the release rates disclosed herein are attained. In some embodiments, the strings can be cut to a length from approximately 8 mm to approximately 14 mm. In some embodiments, the strings can be cut to a length from approximately 9 mm to approximately 13 mm. In some embodiments, the strings can be cut to a length from approximately 10 mm to approximately 12 mm. In some embodiments, the strings can be cut to a length of approximately 11 mm. In some embodiments, the weight of the first core can be from approximately 70 to approximately 120 mg. In some embodiments, the weight of the first core can be from approximately 80 to approximately 100 mg. In some embodiments, the weight of the first core can be from approximately 85 mg to approximately 95 mg. In some embodiments, the weight of the first core is approximately 90 mg.

In certain embodiments, the first core can contain from approximately 25 mg to approximately 75 mg of SA. In some embodiments, the first core can contain from approximately 35 mg to approximately 65 mg of SA In some embodiments, the first core can contain from approximately 40 mg to approximately 50 mg of SA. In some embodiments, the first core contains approximately 45 mg of SA or from 43 mg to 47 mg of SA.

Figure 2:
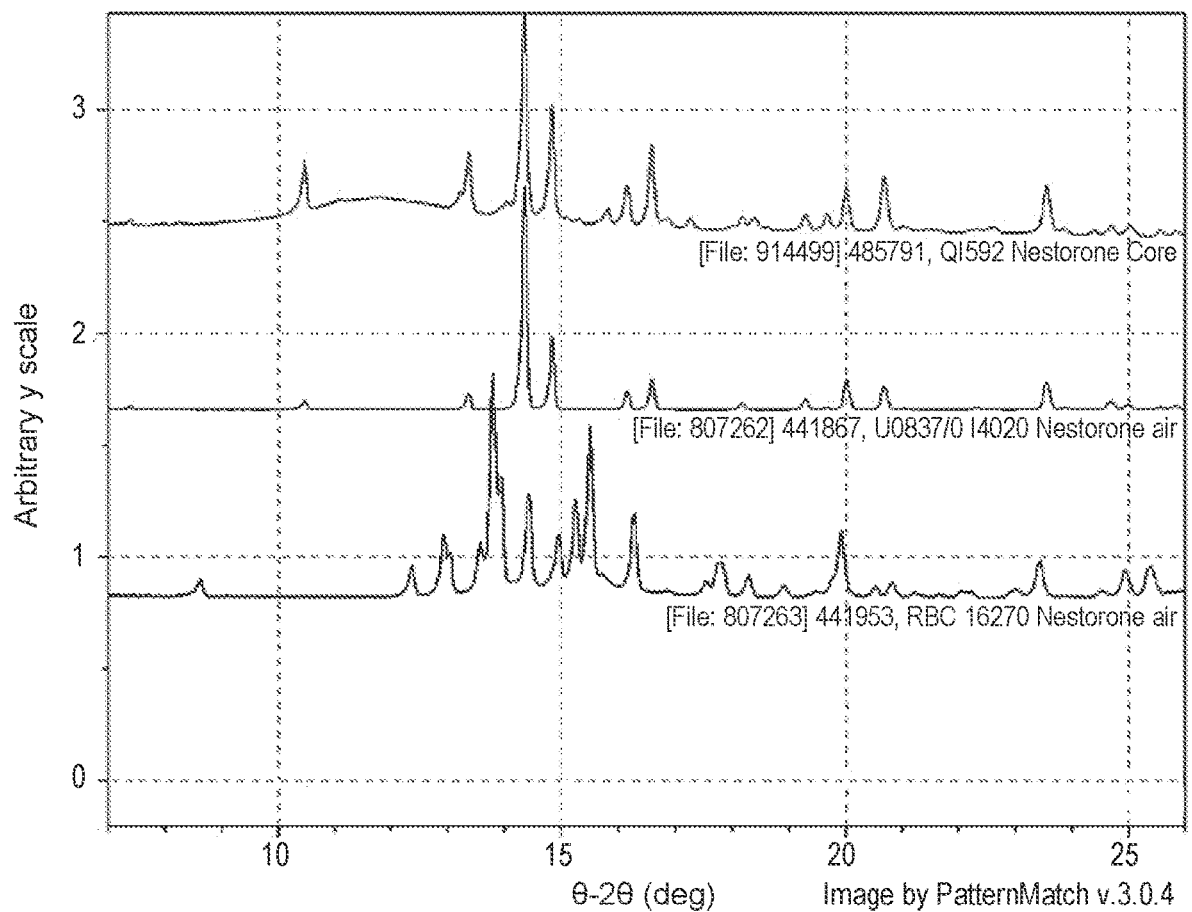
FIG. 2 is an XRPD comparison of the ethinyl estradiol/segesterone acetate core to the historical patterns of segesterone acetate Polymorphic forms I and II.

Segesterone acetate has been found to exist in at least two polymorphic non-solvated forms (Polymorphic form I and Polymorphic form II). Polymorphic forms I and II can be obtained by crystallization under conditions known in the art (see modifications A and B, respectively in Hungarian Patent HU0004967). XRPD patterns for each polymorphic form are shown in FIG. 2, which compares a representative core containing both EE and SA to the historical patterns of each of forms I and II.

In some embodiments, the SA used in the vaginal system described herein can be a pure, or substantially pure, single polymorphic form, such as Polymorphic form I or Polymorphic form II. In some embodiments, however, the SA used in the vaginal system described herein can comprises a mixture of polymorphic forms. For example, and in some embodiments, the SA can comprise from approximately 60% to approximately 99% of Polymorphic form I, by weight, with the remainder being the other known polymorphic form, amorphous SA, or a combination thereof. In some embodiments, the SA can comprise from approximately 70% to approximately 99% of Polymorphic form I. In some embodiments, the SA can comprise from approximately 80% to approximately 99% of Polymorphic form I. Each of the percentages specified is percent by weight.

In some embodiments, the SA contained within each core of the vaginal system can comprise from approximately 1% to approximately 40%, by weight, of Polymorphic form II, with the remainder being the other known polymorphic form, amorphous SA, or a combination thereof. In some embodiments, the SA can comprise from approximately 1% to approximately 30% Polymorphic form II. In some embodiments, the SA can comprise from approximately 1% to approximately 20% Polymorphic form II. In some embodiments, the SA can comprise a detectable amount of Polymorphic form II, but less than 10% Polymorphic form II. All percentages noted above are percent by weight.

Applicants have surprisingly discovered that SA particle size is important for obtaining elastomer core mixes, i.e. pre-core mixtures, that are suitable for extrusion and injection molding. If the SA particles are too large, the resulting pre-core mixture is too soft and thus not suitable for extrusion and/or injection molding. Alternatively, if the SA particle size is too small, the resulting pre-core mixture is too stiff for extrusion and/or injection molding. Particle size also influences the rate at which the compound solubilizes into the core and ultimately affects the release profile of the SA from the system into the patient.

In some embodiments, the SA contained within each core of the vaginal system described herein can be micronized. In some embodiments, the SA contained within each core can have a particle size distribution such that at least 95% of the particles have a particle size of from approximately 0.1 microns to approximately 25 microns, from approximately 0.1 microns to approximately 24 microns, from approximately 0.1 microns to approximately 23 microns, from approximately 0.1 microns to approximately 22 microns, from approximately 0.1 microns to approximately 21 microns, or from approximately 0.1 microns to approximately 20 microns.

In some embodiments, the SA contained within each core can have a particle size distribution wherein approximately 90% of the particles have a particle size from approximately 0.5 microns to approximately 15 microns, from approximately 0.5 microns to approximately 14 microns, from approximately 0.5 microns to approximately 13 microns, from approximately 0.5 microns to approximately 12 microns, from approximately 0.5 microns to approximately 11 microns, or from approximately 0.5 microns to approximately 10 microns.

In some embodiments, the SA contained within each core can have a particle size distribution wherein approximately 50% of the particles have a particle size from approximately 0.5 microns to approximately 10 microns, from approximately 0.5 microns to approximately 9 microns, from approximately 0.5 microns to approximately 8 microns, from approximately 0.5 microns to approximately 7 microns, from approximately 0.5 microns to approximately 6 microns, or from approximately 0.5 microns to approximately 5 microns.

In certain embodiments, the SA contained within each core can have a particle size distribution such that not less than 99% of the particles are less than 100 microns. In some embodiments, the SA contained within each core can have a particle size distribution such that not less than 99% of the particles are less than 90 microns. In some embodiments, the SA contained within each core can have a particle size distribution such that not less than 99% of the particles are less than 80 microns. In some embodiments, the SA contained within each core can have a particle size distribution such that not less than 99% of the particles are less than 70 microns. In some embodiments, the SA contained within each core can have a particle size distribution such that not less than 99% of the particles are less than 60 microns. In some embodiments, the SA contained within each core can have a particle size distribution such that not less than 99% of the particles are less than 50 microns. In some embodiments, the SA contained within each core can have a particle size distribution such that not less than 99% of the particles are less than 40 microns. In some embodiments, the SA contained within each core can have a particle size distribution such that not less than 99% of the particles are less than 30 microns. In some embodiments, the SA contained within each core can have a particle size distribution such that not less than 99% of the particles are less than 20 microns. In some embodiments, the SA contained within each core can have a particle size distribution such that not less than 99% of the particles are less than 10 microns.

In certain embodiments, the SA contained within each core can have a D90 less than or equal to approximately 100 microns. In some embodiments, the SA contained within each core can have a D90 less than or equal to approximately 90 microns. In some embodiments, the SA contained within each core can have a D90 less than or equal to approximately 80 microns. In some embodiments, the SA contained within each core can have a D90 less than or equal to approximately 70 microns. In some embodiments, the SA contained within each core can have a D90 less than or equal to approximately 60 microns. In some embodiments, the SA contained within each core can have a D90 less than or equal to approximately 50 microns. In some embodiments, the SA contained within each core can have a D90 less than or equal to approximately 40 microns. In some embodiments, the SA contained within each core can have a D90 less than or equal to approximately 30 microns. In some embodiments, the SA contained within each core can have a D90 less than or equal to approximately 20 microns. In certain embodiments, the SA contained within each core can have a D90 less than or equal to approximately 15 microns. In certain embodiments, the SA contained within each core can have a D90 less than or equal to approximately 12 microns. In some embodiments, the SA contained within each core can have a D90 less than or equal to approximately 10 microns. In certain embodiments, the SA contained within each core can have a D90 less than or equal to approximately 8 microns. In certain embodiments, the SA contained within each core can have a D90 less than or equal to approximately 6 microns.

In certain embodiments, the SA can have a D50 less than or equal to approximately 75 microns. In certain embodiments, the SA can have a D50 less than or equal to approximately 65 microns. In certain embodiments, the SA can have a D50 less than or equal to approximately 55 microns. In certain embodiments, the SA can have a D50 less than or equal to approximately 45 microns. In certain embodiments, the SA can have a D50 less than or equal to approximately 35 microns. In certain embodiments, the SA can have a D50 less than or equal to approximately 25 microns. In certain embodiments, the SA can have a D50 less than or equal to approximately 15 microns. In some embodiments, the SA can have a D50 less than or equal to approximately 10 microns. In some embodiments, the SA can have a D50 less than or equal to approximately 8 microns. In some embodiments, the SA can have a D50 less than or equal to approximately 5 microns. In some embodiments, the SA can have a D50 less than or equal to approximately 3 microns. In some embodiments, the SA can have a D50 less than or equal to approximately 2 microns.

In certain embodiments, the SA can have a D10 greater than or equal to approximately 50 microns. In some embodiments, the SA can have a D10 greater than or equal to approximately 40 microns. In some embodiments, the SA can have a D10 greater than or equal to approximately 30 microns. In some embodiments, the SA can have a D10 greater than or equal to approximately 20 microns. In some embodiments, the SA can have a D10 greater than or equal to approximately 10 microns. In some embodiments, the SA can have a D10 greater than or equal to approximately 5 microns. In some embodiments, the SA can have a D10 greater than or equal to approximately 3 microns. In some embodiments, the SA can have a D10 greater than or equal to approximately 1 micron. In some embodiments, the SA can have a D10 greater than or equal to approximately 0.6 microns. In some embodiments, the SA can have a D10 greater than or equal to approximately 0.5 microns. In some embodiments, the SA can have a D10 greater than or equal to approximately 0.4 microns.

In certain embodiments, the SA contained within each core can have a D90 less than or equal to approximately 80 microns, a D50 less than or equal to approximately 45 microns, and a D10 greater than or equal to approximately 10 microns. In some embodiments, the SA contained within each core can have a D90 less than or equal to approximately 40 microns, a D50 less than or equal to approximately 25 microns, and a D10 greater than or equal to approximately 5 microns. In some embodiments, the SA contained within each core can have a D90 less than or equal to approximately 20 microns, a D50 less than or equal to approximately 15 microns, and a D10 greater than or equal to approximately 1 micron. In some embodiments, the SA contained within each core can have a D90 less than or equal to approximately 10 microns, a D50 less than or equal to approximately 5 microns, and a D10 greater than or equal to approximately 0.6 microns. In some embodiments, the SA contained within each core can have a D90 less than or equal to approximately 8 microns, a D50 less than or equal to approximately 3 microns, and a D10 greater than or equal to approximately 0.4 microns. In some embodiments, the SA contained within each core can have a D90 less than or equal to approximately 6 microns, a D50 less than or equal to approximately 2 microns, and a D10 greater than or equal to approximately 0.2 microns.

In certain embodiments, the vaginal system comprises a second core which comprises SA and EE. In some embodiments, the second core comprises a one or more condensation cure silicone elastomers. In some embodiments, the second core comprises a single condensation cure silicone elastomer. In some embodiments, the condensation cure silicone elastomer is selected from the group consisting of NuSil™ MED-6603 (formerly known as DDU-4352), NuSil™ MED3-6603, NuSil™ MED-6381, NuSil™ MED-6382, and NuSil™ MED-6385, as described elsewhere herein. In certain embodiments, the second core comprises NuSil™ MED-6603 (formerly known as DDU-4352). This material is commercially available.

In certain embodiments, the second core comprises a single elastomer, SA, and EE. In some embodiments, the second core can be prepared by blending the elastomer and the EE. In some embodiments, SA is added to the blend in batches. In some embodiments, the resulting mixture containing the elastomer, EE, and SA can be divided into smaller batches before treatment with a curing agent. In some embodiments, the curing agent can be a tin catalyst. In some embodiments, the curing agent can be dibutyltin dilaurate. In some embodiments, the curing agent is NuSil™ MED-6603 Part B. In some embodiments, the resulting mixture can be extruded into strings after addition of the curing agent.

Applicants have surprisingly discovered that the temperature and relative humidity at which the second core is cured can be important to the rate at which the EE is released on Day 1 of the first product use cycle. Higher curing temperatures and higher relative humidity during the curing process cause an unacceptable EE burst on Day 1. This effect was not seen in the core containing only SA. In certain embodiments, the strings containing EE and SA can be cured at a temperature below approximately 120° C. In some embodiments, the strings can be cured at a temperature of approximately room temperature to approximately 115° C. In some embodiments, the strings can be cured at a temperature of from approximately 40° C. to approximately 110° C. In some embodiments, the strings can be cured at a temperature of from approximately 50° C. to approximately 100° C. In some embodiments, the strings can be cured at a temperature of from approximately 60° C. to approximately 90° C. In some embodiments, the strings can be cured at a temperature of from approximately 90° C. In some embodiments, the strings can be cured at a temperature of approximately 60° C.

In some embodiments, the amount of time that the strings are cured increases with a decrease in curing temperature. In certain embodiments, the strings can be cured for from approximately 5 minutes to approximately 60 minutes. In some embodiments, the strings can be cured for from approximately 25 minutes to approximately 50 minutes. In some embodiments, the strings can be cured for from approximately 30 minutes to approximately 45 minutes. In some embodiments, the strings can be cured for from approximately 30 minutes. In some embodiments, the strings can be cured at approximately 90° C. for approximately 10 minutes. In some embodiments, the strings can be cured at approximately 60° C. for approximately 15 to approximately 20 minutes.

In certain embodiments, the strings can be cured at a relative humidity of less than approximately 5%. In certain embodiments, the strings can be cured at a relative humidity of less than approximately 4%. In some embodiments, the strings can be cured at a relative humidity of less than approximately 3%. In some embodiments, the strings can be cured at a relative humidity of less than approximately 2%. In some embodiments, the strings can be cured at a relative humidity from approximately 1% to approximately 2%. In some embodiments, the strings can be cured at a relative humidity of approximately 1.8%.

In some embodiments, the cured product can be post-cured at room temperature for at least 2 days. In some embodiments, the cured product can be post-cured at room temperature for at least 3 days. In some embodiments, the cured product can be post-cured at room temperature for at least 4 days. In some embodiments, the cured product can be post-cured at room temperature for at least 5 days. In some embodiments, the cured product can be post-cured at room temperature for at least 6 days. In some embodiments, the cured product can post-cured at room temperature for at least 7 days. In some embodiments, the cured product can be post-cured at room temperature for at least 8 days. In some embodiments, the cured product can be post-cured at room temperature for at least 9 days. In some embodiments, the cured product can be post-cured at room temperature for at least 10 days.

In some embodiments, the strings can be cut after the post-cure period to provide the cores. In some embodiments, the strings can be cut to a length from approximately 15 mm to approximately 21 mm. In some embodiments, the strings can be cut to a length from approximately 16 mm to approximately 20 mm. In some embodiments, the strings can be cut to a length from approximately 17 mm to approximately 19 mm. In some embodiments, strings are cut to a length of approximately 18 mm. In certain embodiments, the weight of the second core can be from approximately 115 mg to approximately 175 mg. In certain embodiments, the weight of the second core can be from approximately 125 mg to approximately 165 mg. In some embodiments, the weight of the second core can be from approximately 135 mg to approximately 155 mg. In some embodiments, the weight of the second core can be approximately 145 mg.

In certain embodiments, the second core can contain from approximately 40 mg to approximately 80 mg of SA. In certain embodiments, the second core can contain from approximately 50 mg to approximately 70 mg of SA. In some embodiments, the second core can contain from approximately 50 mg to approximately 60 mg of SA. In some embodiments, the second core can contain from approximately 55 mg to approximately 60 mg of SA. In some embodiments, the second core can contain approximately 58 mg of SA, or from 56 to 60 mg SA.

In some embodiments, the second core can contain from approximately 14 mg to approximately 25 mg of EE. In some embodiments, the second core can contain from approximately 15 mg to approximately 20 mg of EE. In some embodiments, the second core can contain from approximately 16 mg to approximately 19 mg of EE. In some embodiments, the second core can contain from approximately 15 mg to approximately 18 mg of EE. In some embodiments, the second core can contain from approximately 16 mg to approximately 18 mg of EE. In some embodiments, the second core can contain approximately 17.4 mg of EE, or from 17.2 to 17.6 mg of EE.

Figure 3:
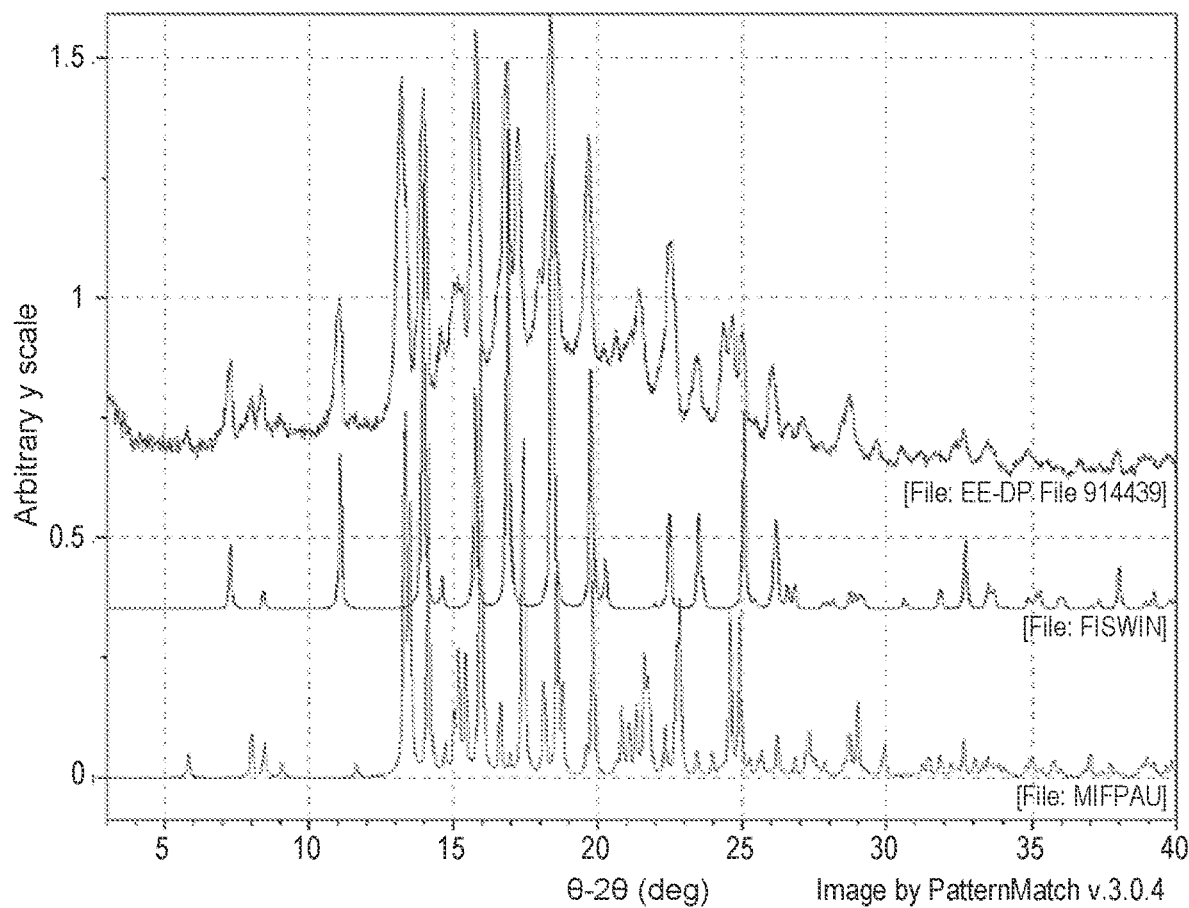
FIG. 3 is an XRPD comparison of ethinyl estradiol to the calculated patterns of ethinyl estradiol hemihydrate and anhydrous ethinyl estradiol.

Crystalline forms of EE and multiple crystalline EE hydrates are known in the literature (see, for example, Pheasant, R., "Polymorphism of 17-Ethinylestradiol", *J. Am. Chem. Soc.* 1950, 72 (9), pp 4303-4304 and Guguta, C. et al., *Cryst. Growth Des.* 2008, 8 (3), pp 823-831 which are both incorporated by reference in their entireties). A comparison of the XRPD pattern of the EE API to the calculated XRPD patterns of EE hemihydrate and anhydrous EE are shown in FIG. 3. In some embodiments, the EE contained within the second core comprises one or more anhydrous forms. In some embodiments, the EE contained within the second core comprises one or more hemihydrate forms. In some embodiments, the EE contained within the second core comprises a mixture of one or more anhydrous forms and one or more hemihydrate forms. In certain embodiments, the EE contained within the second core comprises a crystalline form that melts from approximately 181° C. to approximately 186° C. In some embodiments, the EE comprises a crystalline form that melts from approximately 141 to approximately 146° C. In yet another embodiment, the EE contained within the second core comprises a mixture of a crystalline form that melts from approximately 181° C. to approximately 186° C. and a crystalline form that melts from approximately 141 to approximately 146° C., wherein the ratio of these crystalline forms ranges from approximately 99:1 to approximately 1:99, by weight.

As discussed herein, particle size influences the rate at which the compound solubilizes into the core and ultimately affects the release profile of the EE from the system into the patient. In some embodiments, the EE contained within the second core of the vaginal system can be micronized. In some embodiments, the EE contained within the second core can have maximum particle size from approximately 10 microns to approximately 20 microns. In some embodiments, the EE contained within the second core can have maximum particle size from approximately 11 microns to approximately 19 microns. In some embodiments, the EE contained within the second core can have maximum particle size from approximately 12 microns to approximately 18 microns. In some embodiments, the EE contained within the second core can have maximum particle size from approximately 13 microns to approximately 17 microns. In some embodiments, the EE contained within the second core can have maximum particle size from approximately 14 microns to approximately 16 microns. In some embodiments, the EE can have a maximum particle size of approximately 15 microns.

In some embodiments, the EE can have a particle size distribution wherein approximately 99% of the particles have a maximum particle size from approximately 11 microns to approximately 15 microns. In some embodiments, the EE can have a particle size distribution wherein approximately 99% of the particles have a maximum particle size from approximately 12 microns to approximately 14 microns. In some embodiments, the EE can have a particle size distribution wherein approximately 99% of the particles have a maximum particle size from approximately 12 microns to approximately 13 microns. In some embodiments, the EE can have a particle size distribution wherein approximately 99% of the particles have a maximum particle size of approximately 12.5 microns. In some embodiments, the EE can have a particle size distribution wherein approximately 95% of the particles have a maximum particle size from approximately 8 microns to approximately 13 microns. In some embodiments, the EE can have a particle size distribution wherein approximately 95% of the particles have a maximum particle size from approximately 9 microns to approximately 12 microns. In some embodiments, the EE can have a particle size distribution wherein approximately 95% of the particles have a maximum particle size from approximately 9 microns to approximately 11 microns. In some embodiments, the EE can have a particle size distribution wherein approximately 95% of the particles have a maximum particle size of approximately 10.0 microns. In some embodiments, the EE can have a particle size distribution wherein approximately 50% of the particles have a maximum particle size from approximately 1 micron to approximately 4 microns. In some embodiments, the EE can have a particle size distribution wherein approximately 50% of the particles have a maximum particle size from approximately 2 microns to approximately 4 microns. In some embodiments, the EE can have a particle size distribution wherein approximately 50% of the particles have a maximum particle size of approximately 3 microns. In some embodiments, the EE can have a particle size distribution wherein approximately 40% or less of the particles have a particle size less than or equal to approximately 2 microns. In some embodiments, the EE can have a particle size distribution wherein approximately 40% or less of the particles have a particle size less than or equal to approximately 1.5 microns. In some embodiments, the EE can have a particle size distribution wherein approximately 40% or less of the particles have a particle size less than or equal to approximately 1.3 microns.

It has been surprisingly discovered that the age of the second core upon assembly into the ring body impacts the initial burst of EE on Day 1. For example, newer cores were shown to provide an unacceptable EE burst on Day 1. In certain embodiments, post curing, one or more of the cores can be stored for at least 8 days before assembling into the ring body. In certain embodiments, post-curing, one or more of the cores can be stored for at least 10 days before assembling into the ring body. In certain embodiments, post-curing, one or more of the cores can be stored for at least 12 days before assembling into the ring body. In certain embodiments, post-curing, one or more of the cores can be stored for at least 14 days before assembling into the ring body. In certain embodiments, post-curing, one or more of the cores can be stored for at least 16 days before assembling into the ring body. In certain embodiments, post-curing, one or more of the cores can be stored for at least 18 days before assembling into the ring body. In certain embodiments, post-curing, one or more of the cores can be stored for at least 20 days before assembling into the ring body. In certain embodiments, post-curing, one or more of the cores can be stored for at least 21 days before assembling into the ring body. In certain embodiments, post-curing, one or more of the cores can be stored for at least 22 days before assembling into the ring body. In certain embodiments, post-curing, one or more of the cores can be stored for at least 23 days before assembling into the ring body. In certain embodiments, post-curing, one or more of the cores can be stored for at least 24 days before assembling into the ring body. In certain embodiments, post-curing, one or more of the cores can be stored for at least 25 days before assembling into the ring body. In certain embodiments, post-curing, one or more of the cores can be stored for at least 26 days before assembling into the ring body. In certain embodiments, post-curing, one or more of the cores can be stored for at least 27 days before assembling into the ring body. In certain embodiments, post-curing, one or more of the cores can be stored for at least 28 days before assembling into the ring body. In certain embodiments, post-curing, one or more of the cores can be stored for at least 29 days before assembling into the ring body. In certain embodiments, post-curing, one or more of the cores can be stored for at least 30 days before assembling into the ring body. In certain embodiments, post-curing, one or more of the cores can be stored for at least 31 days before assembling into the ring body. In certain embodiments, post-curing, one or more of the cores can be stored for at least 32 days before assembling into the ring body. In certain embodiments, post-curing, one or more of the cores can be stored for at least 33 days before assembling into the ring body. In certain embodiments, post-curing, one or more of the cores can be stored for at least 34 days before assembling into the ring body. In certain embodiments, post-curing, one or more of the cores can be stored for at least 35 days before assembling into the ring body.

In certain embodiments, the shaping of the pre-core mixture, the cutting of the resulting cores, and/or storage of the resulting cores can be performed at a temperature of from approximately 10° C. to approximately 40° C. In certain embodiments, the shaping of the pre-core mixture, the cutting of the resulting cores, and/or storage of the resulting cores can be performed at a temperature of from approximately 15° C. to approximately 35° C. In certain embodiments, the shaping of the pre-core mixture, the cutting of the resulting cores, and/or storage of the resulting cores can be performed at a temperature of from approximately 15° C. to approximately 30° C. In some embodiments, the shaping of the pre-core mixture, the cutting of the resulting cores, and/or storage of the resulting cores can be performed at a temperature of from approximately 20° C. to approximately 25° C.

In some embodiments, the shaping of the pre-core mixture, the cutting of the resulting cores, and/or storage of the resulting cores can be performed at a relative humidity of greater than or equal to approximately 10%. In some embodiments, the shaping of the pre-core mixture, the cutting of the resulting cores, and/or storage of the resulting cores can be performed at a relative humidity of greater than or equal to approximately 20%. In some embodiments, the shaping of the pre-core mixture, the cutting of the resulting cores, and/or storage of the resulting cores can be performed at a relative humidity of greater than or equal to approximately 30%. In some embodiments, the shaping of the pre-core mixture, the cutting of the resulting cores, and/or storage of the resulting cores can be performed at a relative humidity of greater than or equal to approximately 40%.

In some embodiments, the cores of the vaginal system described herein conform to the guidelines outlined in the US Pharmacopeial Convention, incorporated herein by reference, and in particular USP <905>.

Ring Body

The vaginal system ring body typically comprises one or more polymers. In certain embodiments, the ring body comprises one or more polymers selected from a polystyrene, a thermoplastic polymer (including, but not limited to, poly(methyl methacrylate), acrylonitrile butadiene styrene, nylon, polylactic acid, polybenimidazole, polycarbonate, polyether sulfone, polyoxymethylene, polyetherketone, polyetherimide, polyethylene, polyphenylene oxide, polyphenylene sulfide, polypropylene, polystyrene, polyvinyl chloride, polyvinylidene fluoride, and teflon), and elastomers (including, but not limited to natural and synthetic polyisoprene, polybutadiene, chloroprene, butyl rubber (including halogenated derivatives thereof), styrene-butadiene, nitrile rubber (including halogenated derivatives thereof), ethylene/propylene rubbers (including both melt blends and reactor blends (block copolymers) of ethylene and propyelene), epichlorohydrin rubber, polyacrylic rubber, a silicone elastomer, fluorosilicone rubber, a fluoroelastomer (e.g. VITON, TECNOFLON, FLUOREL, AFAS, and DAI-EL), a perfluoroelastomer, a polyether block amide, chlorosulfonated polyethylene, ethylene vinylacetate ("EVA")). In some embodiments, the ring body comprises EVA. In some embodiments, the ring body comprises one or more elastomers wherein the elastomers are silicone elastomers. In some embodiments, the ring body comprises a mixture of silicone and other elastomers. In some embodiments, the ring body comprises a single silicone elastomer. In other embodiments, the ring body comprises multiple silicone elastomers. In some embodiments the ring body comprises a condensation-cure silicone elastomer. In other embodiments, the ring body comprises an addition-cure silicone elastomer.

In some embodiments, the ring body comprises a silicone addition-cure elastomer. Addition-cure systems silicone elastomers typically include vinyl-terminated silicone polymers, a platinum catalyst, and a silyl-hydride cross-linker. In general, silicone addition-cure elastomers are supplied as two-part systems that need to be intimately mixed to initiate curing. That said, and in other embodiments, the addition cure silicone elastomers can be supplied pre-mixed as non-polymerized starting materials, with a separate catalyst, or in three distinct component parts which are subsequently mixed in an appropriate ratio.

In certain embodiments, the ring body comprises a medical grade addition-cure silicone elastomer having a platinum concentration from approximately 1 ppm to approximately 15 ppm. In certain embodiments, the ring body comprises a medical grade addition-cure silicone elastomer having a platinum concentration from approximately 2 ppm to approximately 12 ppm. In certain embodiments, the ring body comprises a medical grade addition-cure silicone elastomer having a platinum concentration from approximately 2 ppm to approximately 10 ppm. In some embodiments, the addition-cure silicone elastomer can be a polysiloxane elastomer comprising approximately 2 ppm to approximately 10 ppm platinum. In some embodiments, the polysiloxane elastomer can be a diorganopolysiloxane elastomer comprising approximately 2 ppm to approximately 10 ppm platinum. In some embodiments, the diorganopolysiloxane elastomer can be a dimethylpolysiloxane elastomer comprising approximately 2 ppm to approximately 10 ppm platinum. As will be discussed in more detail below, it has been surprisingly discovered that the concentration of platinum in the ring body is believed to play a role in controlling the release rate of EE in the vaginal system. Concentrations of platinum above or below the specified ranges can lead to increased rates of EE sequestration, while insufficient platinum can lead to release of too much EE, and the concomitant side effects associated with too much estradiol.

In addition to having the specified platinum concentration, the addition-cure silicone elastomer can also comprise one or more opacity agents, one or more pigments, one or more antidegradants, one or more fillers, or combinations thereof.

In certain embodiments, the addition-cure silicone elastomer having the specified platinum concentration can be prepared from two components, "Part A" and "Part B." In some embodiments, the first part (Part A), contains uncured vinyl-terminated silicone polymers and a platinum catalyst which acts as a curing agent. In some embodiments, the second part (Part B) contains uncured vinyl-terminated silicone polymers and a hydride cross-linker. In certain embodiments, the ratio of hydride cross-linker ("hydride") to vinyl-terminated polymer ("vinyl") within both Part A and Part B is from approximately 1:2 to approximately 5:1. In some embodiments, the hydride/vinyl ratio is from approximately 1:1.5 to approximately 4:1. In some embodiments, the hydride/vinyl ratio is from approximately 1:1.5 to approximately 3:1. In some embodiments, the hydride/vinyl ratio is from approximately 1:1.5 to approximately 2:1. In some embodiments, the hydride/vinyl ratio is from approximately 1:1.5 to approximately 1.5:1. In some embodiments, the hydride/vinyl ratio is from approximately 1:1 to approximately 1.3:1. In some embodiments, the hydride/vinyl ratio is from approximately 1:1 to approximately 1.2:1.

Increasing the ratio of Part A to Part B has been found to increase both tensile strength and elongation of the cured elastomer without affecting the Shore A hardness. Accordingly, the appropriate ratios of Part A and Part B can be selected to provide an elastomer that had enough flexibility as to be easy to insert and remove, yet be durable enough to withstand the physical stress of use. In certain embodiments, the ring body elastomer can be prepared by mixing an approximately 8:1 to approximately 12:1 ratio of Part A to Part B. In certain embodiments, the addition-cure silicone elastomer can be prepared by mixing an approximately 9:1 to approximately 11:1 ratio of Part A to Part B. In certain embodiments, the addition-cure silicone elastomer can be prepared by mixing an approximately 9.5:1 to approximately 10.5:1 ratio of Part A to Part B. In certain embodiments, the addition-cure silicone elastomer can be prepared by mixing an approximately 10:1 ratio of Part A to Part B.

In some embodiments, the addition-cure silicone elastomer having the noted platinum concentration can be NuSil™ MED-4870. NuSil™ MED-4870 can be prepared by mixing two components, "Part A" and "Part B." In addition to siloxanes and silicones, Part A in this embodiment can comprise 30-40% trimethylsilylsilanamine (CAS No. 68909-20-6). Part B in this embodiment can comprise dimethylsiloxanes and dimethylsilicones, as well as 30-40% trimethylsilylsilanamine (CAS No. 689-20-6) and a platinum catalyst.

In some embodiments, the addition-cure silicone elastomer having a platinum concentration within the specified ranges can be NuSil™ DDU-4320. Like other addition-cure silicone elastomers, NuSil™ DDU-4320 can be prepared by mixing appropriate ratios of two components, "Part A" and "Part B." In this embodiment, Part A can comprise 40-50% vinyl-terminated dimethylsiloxanes and dimethylsilicones (CAS No. 68952-0001), 10-20% amorphous, fumed, crystalline-free silica (CAS No. 112945-52-5), and <1% hydroxyl-1% hydroxyl-terminated dimethyl and methyl-vinylsiloxanes and silicones (CAS No. 67923-19-7). In some embodiments, Part B comprises 40-50% vinyl-terminated dimethylsiloxanes and dimethylsilicones (CAS No. 68952-0001), 30-40% ethenyldimethylsilyloxy- and trimethylsilyloxy-modified silica (CAS No. 68988-89-6), 10-20% amorphous, fumed, crystalline-free silica (CAS No. 112945-52-5), <1% silicic acid tetraethyl ester (CAS No. 68988-57-8), <1% 1-ethynylcyclohexanol (CAS No. 78-27-3), and <1% hydroxyl-terminated dimethyl and methyl-vinylsiloxanes and silicones (CAS No. 67923-19-7).

In some embodiments, the addition-cure silicone elastomer having a platinum concentration within the specified ranges can be MED4-4224 (previously known as DDU-4331). As above, this addition-cure silicone elastomer can be prepared by mixing appropriate ratios of two components, "Part A" and "Part B." In this embodiment, Part A comprises 65-75% mono(vinyl group) terminated dimethylsiloxanes and dimethylsilicones (CAS No. 68952-00-1), 15-20% amorphous, fumed, crystalline-free silica (CAS No. 112945-52-5), and <5% titanium dioxide (CAS No. 137463-67-7). Part B, in this embodiment, comprises 65-75% mono(vinyl group) terminated dimethylsiloxanes and dimethylsilicones (CAS No. 68952-00-1), 10-15% siloxanes and silicones (dimethyl and methyl) (CAS No. 68037-59-2), and a platinum catalyst.

In some embodiments, the silicone elastomer is NuSil™ MED4-4224 (previously known as DDU-4331). In some embodiments, in addition to the components noted above, the NuSil™ MED4-4224 comprises one or more opacity agents. In some embodiments, the opacity agent is titanium dioxide. In some embodiments, the NuSil™ MED4-4224 comprises approximately 4% $TiO_2$ by weight.

In some embodiments, the ring body can be formed when the component parts of the addition-cure silicone elastomer are mixed and then molded into ring bodies and subjected to curing conditions. In some embodiments, the ring bodies can be cured at a temperature of from approximately 120° C. to approximately 180° C. In some embodiments, the ring bodies can be cured at a temperature of from approximately 130° C. to approximately 170° C. In some embodiments, the ring bodies can be cured at a temperature of from approximately 140° C. to approximately 160° C. In some embodiments, the ring bodies are cured at a temperature of from approximately 145° C. to approximately 155° C. In some embodiments, the ring bodies can be cured from approximately 20 to approximately 210 seconds. In some embodiments, the ring bodies can be cured from approximately 30 to approximately 200 seconds. In some embodiments, the ring bodies can be cured from approximately 40 to approximately 190 seconds. In some embodiments, the ring bodies can be cured from approximately 50 to approximately 190 seconds. In some embodiments, the ring bodies can be cured from approximately 60 to approximately 180 seconds. In some embodiments, the ring bodies can be cured for approximately 180 seconds.

In certain embodiments, the cured elastomer ring body has a specific gravity of from approximately 1 to approximately 1.5. In some embodiments, the cured elastomer ring body has a specific gravity of from approximately 1.05 to approximately 1.4. In some embodiments, the cured elastomer ring body has a specific gravity of from approximately 1.05 to approximately 1.3. In some embodiments, the cured elastomer ring body has a specific gravity of from approximately 1.05 to approximately 1.25. In some embodiments, the cured elastomer ring body has a specific gravity of from approximately 1.05 to approximately 1.20. In some embodiments, the cured elastomer ring body has a specific gravity of from approximately 1.07 to approximately 1.17. In some embodiments, the cured elastomer ring body has a specific gravity of from approximately 1.08 to approximately 1.11.

In certain embodiments, the ring bodies can be removed from the mold and allowed to rest before inserting the cores. In some embodiments, the ring bodies can be rested at a temperature of from approximately 10° C. to approximately 40° C. In some embodiments, the ring bodies can be rested at a temperature of from approximately 15° C. to approximately 35° C. In some embodiments, the ring bodies can be rested at a temperature of from approximately 15° C. to approximately 30° C. In some embodiments, the ring bodies can be rested at a temperature from approximately 19° C. to approximately 25° C. In some embodiments, the ring bodies can be rested for a period of from approximately 10 to approximately 45 days. In some embodiments, the ring bodies can be rested for a period of from approximately 20 to approximately 40 days. In some embodiments, the ring bodies are rested for approximately 30 days.

As noted elsewhere herein, the ring body contains one or more channels adapted to receive the active-impregnated cores. In certain embodiments, the channels adapted to receive the cores can be created within the ring bodies during the molding process. Alternatively, any suitable means for creating the channel after the molding process is complete can also be used. For example, and in some embodiments, the channels can be prepared by laser or by using an appropriate cutting mechanism, such as a metal blade or high-pressure water. In some embodiments, the channels can be created by puncturing. In some embodiments, the channels can be created by drilling. An appropriate mechanism for introducing the one or more channels into the ring body can be selected depending upon channel placement and size and other factors. As noted elsewhere herein, the channel or channels adapted to receive the core(s) can be a bore, such as a cylindrical bore adapted to receive an appropriately shaped cylindrical or spherical core. In other embodiments, the channel or channels can be adapted to receive a core or cores shaped like a rectangular prism, including for example a square prism, or a core or cores shaped like a cone, a triangular prism, a triangular pyramid, a rectangular pyramid, a pentagonal prism, a hexagonal prism, a heptagonal prism, or any other three dimensional shape suitable for manufacture. In some embodiments, the channel or channels can be adapted to receive a core or cores that are disc-shaped. In certain embodiments, the channel or channels can be adapted to receive a cylindrical core or core shaped like a rectangular prism.

Curing results in hardening of the resulting ring body. In certain embodiments, the cured ring body has a mean elongation parallel to the cores of between approximately 350 and approximately 550%. In some embodiments, the cured ring body has a mean elongation parallel to the cores of between approximately 375 and approximately 525%. In some embodiments, the cured ring body has a mean elongation parallel to the cores of between approximately 400 and approximately 500%. In some embodiments, the cured ring body has a mean elongation parallel to the cores of approximately 418%. In certain embodiments, the cured ring body has a mean elongation perpendicular to the cores of between approximately 350 and approximately 550%. In some embodiments, the cured ring body has a mean elongation perpendicular to the cores of between approximately 375 and approximately 525%. In some embodiments, the cured ring body has a mean elongation perpendicular to the cores of between approximately 400 and approximately 500%. In some embodiments, the cured ring body has a mean elongation perpendicular to the cores of approximately 474%.

In certain embodiments, the cured ring body has a mean tensile strength parallel to the cores of from approximately 9,000 $N/mm^2$ to approximately 10,000 $N/mm^2$. In some embodiments, the cured ring body has a mean tensile strength parallel to the cores of from approximately 9,100 $N/mm^2$ to approximately 9,750 $N/mm^2$. In some embodiments, the cured ring body has a mean tensile strength parallel to the cores of from approximately 9,200 $N/mm^2$ to approximately 9,500 $N/mm^2$. In some embodiments, the cured ring body has a mean tensile strength parallel to the cores of from approximately 9,300 $N/mm^2$ to approximately 9,400 $N/mm^2$. In some embodiments, the cured ring body has a mean tensile strength parallel to the cores of approximately 9312 $N/mm^2$. In certain embodiments, the cured ring body has a mean tensile strength perpendicular to the cores of from approximately 10,000 $N/mm^2$ to approximately 11,000 $N/mm^2$. In some embodiments, the cured ring body has a mean tensile strength perpendicular to the cores of from approximately 10,100 $N/mm^2$ to approximately 10,750 $N/mm^2$. In some embodiments, the cured ring body has a mean tensile strength perpendicular to the cores of from approximately 10,200 $N/mm^2$ to approximately 10,500 $N/mm^2$. In some embodiments, the cured ring body has a mean tensile strength perpendicular to the cores of from approximately 10,300 $N/mm^2$ to approximately 10,400

N/mm². In some embodiments, the cured ring body has a mean tensile strength perpendicular to the cores of approximately 10,369 N/mm².

In certain embodiments, the cured ring body has a mean fatigue parallel to the cores between approximately 80 and approximately 110%. In some embodiments, the cured ring body has a mean fatigue parallel to the cores between approximately 85 and approximately 105%. In some embodiments, the cured ring body has a mean fatigue parallel to the cores between approximately 90 and approximately 100%. In some embodiments, the cured ring body has a mean fatigue parallel to the cores of approximately 95%. In certain embodiments, the cured ring body has a mean fatigue perpendicular to the cores between approximately 80 and approximately 100%. In some embodiments, the cured ring body has a mean fatigue perpendicular to the cores between approximately 85 and approximately 100%. In some embodiments, the cured ring body has a mean fatigue perpendicular to the cores between approximately 90 and approximately 100%. In some embodiments, the cured ring body has a mean fatigue perpendicular to the cores of approximately 98%.

In some embodiments, the cured elastomer has a shore A hardness of from approximately 10 to approximately 50. In some embodiments, the cured elastomer has a shore A hardness of from approximately 15 to approximately 45. In some embodiments, the cured elastomer has a shore A hardness of from approximately 20 to approximately 40. In some embodiments, the cured elastomer has a shore A hardness of from approximately 25 to approximately 35. In some embodiments, the cured elastomer has a shore A hardness of from approximately 25 to approximately 30.

Assembly of the Vaginal System

Depending on the configuration, the vaginal system can be completed by inserting an appropriate number of appropriately aged cores into channels or other structures within the ring body adapted to receive the core(s). In some embodiments, one or more suitable medical adhesives can be added to secure the cores in the ring body. In some embodiments, the medical adhesive can be added before the cores are added. In some embodiments, the medical adhesive can be added after the cores are added and in certain embodiments, the medical adhesive can be added before and after the cores are added. In certain embodiments, the medical adhesive can be a one-part acetoxy (alkyltriacetoxysilane) or alcohol (alkoxy) cross-linked cure system. These one-part adhesives cure in the presence of ambient humidity. In some embodiments, the acetoxy cure system utilizes a tin catalyst, while in other embodiments, the acetoxy cure system does not utilize a tin catalyst. In other embodiments, the medical adhesive can be a UV-cure (solvent-free) adhesive. Such adhesives are known in the art and comprise a photoinitiatior that initiates cross linking upon exposure to UV radiation between 200 to 500 nm.

Medical adhesives can be purchased from vendors such as NuSil and Elkem. In some embodiments, the medical adhesive used can be NuSil™ MED-1134, which comprises 15-25% trimethylsilanamine (CAS No. 68909-20-6) and <5% methylsilanetriol triacetate (CAS No. 4253-34-3). In some embodiments, the channels can be sealed with additional medical adhesive. In certain embodiments, and in a ring body containing two channels, the ring can be assembled by adding medical adhesive to each channel, inserting one core, generally an aged core, into each channel, and adding additional medical adhesive to the channels once the cores are added.

In some embodiments, the ring can be assembled at a temperature of from approximately 10° C. to approximately 35° C. In some embodiments, the ring assembly can be conducted at a temperature of from approximately 15° C. to approximately 30° C. In certain embodiments, the ring assembly can be conducted at a relative humidity of from approximately 40% to approximately 95%. In certain embodiments, the ring assembly can be conducted at a relative humidity of from approximately 45% to approximately 90%. In some embodiments, the ring assembly can be conducted at a relative humidity of from approximately 50% to approximately 80%. In some embodiments, the ring assembly can be conducted at a relative humidity of from approximately 50% to approximately 75%. In some embodiments, the ring assembly can be conducted at a relative humidity of from approximately 50% to approximately 65%. In some embodiments, the ring assembly can be conducted at a relative humidity of approximately 55%.

In some embodiments, the vaginal system can be assembled by extruding the ring body about one or more cores.

In some embodiments, the assembled vaginal system can be cured at room temperature for a period of approximately 1 to approximately 14 days. In some embodiments, the assembled vaginal system can be cured at room temperature for a period of approximately 2 to approximately 10 days. In some embodiments, the assembled vaginal system can be cured for a period of approximately 3 to approximately 7 days.

In certain embodiments, the assembled vaginal system has a total weight of approximately 6 grams to approximately 15 grams. In some embodiments, the assembled vaginal system has a total weight of approximately 6 grams to approximately 10 grams. In some embodiments, the assembled vaginal system has a total weight of approximately 8 grams to approximately 10 grams. In some embodiments, the assembled vaginal system has a total weight of approximately 9 grams.

In certain embodiments, the assembled vaginal system can be packaged into a pouch. In some embodiments, the pouch comprises aluminum. In some embodiments, the ring can be packaged at a temperature of from approximately 10° C. to approximately 35° C. In some embodiments, the packaging can be conducted at a temperature of from approximately 15° C. to approximately 30° C. In some embodiments, the packaging can be conducted at a relative humidity greater than or equal to 40%. In some embodiments, the packaging can be conducted at a relative humidity of from approximately 40% to approximately 90%. In some embodiments, the packaging can be conducted at a relative humidity of from approximately 50% to approximately 80%. In some embodiments, the packaging can be conducted at a relative humidity of from approximately 50% to approximately 70%. In some embodiments, the packaging can be conducted at a relative humidity of approximately 55%.

In other embodiments, the packaged vaginal system can be matured at a temperature of from approximately 10° C. to approximately 35° C. In certain embodiments, the packaged vaginal system can be matured at a temperature of from approximately 15° C. to approximately 30° C. In certain embodiments, the maturation time can be from approximately 15 to approximately 60 days. In certain embodiments, the maturation time can be from approximately 25 to approximately 40 days. In some embodiments, the maturation time can be from approximately 28 to approximately 35 days.

In some embodiments, the vaginal system described herein operates when the EE and SA partially solubilize into the cores into which they are contained, then diffuse from the cores into the ring body and eventually out of the ring body and into the patient. The system is complex, as the rate of solubilization must be controlled to deliver the proper amount of each agent for each of the thirteen 28-day product use cycles. If the agents are too soluble in either the cores or the ring body, too much agent is released, and if too little EE or SA are solubilized into the core or the ring body, an insufficient amount will be released. Stability of the rings over extended periods of time is also essential. That is, the polymeric systems chosen must be compatible with both SA and EE such that sufficient amounts of both SA and EE remain available in sufficient quantities to provide the desired release rate of both active agents over thirteen product use cycles, especially as the vaginal system is repeatedly exposed to twenty one-day periods of heat and humidity once placed in the vagina.

Surprisingly, it was discovered that while the amount of SA recoverable from the vaginal system over 24 months of storage at 25° C. and 60% relative humidity remained essentially constant, the amount of EE recoverable from the system decreased in a time-dependent manner. This was quite surprising as a similar trend was not observed during long-term stability studies on the cores before assembly. In fact, the full amount of EE was found to be recoverable from the core by extraction even after extended storage.

Figure 4:
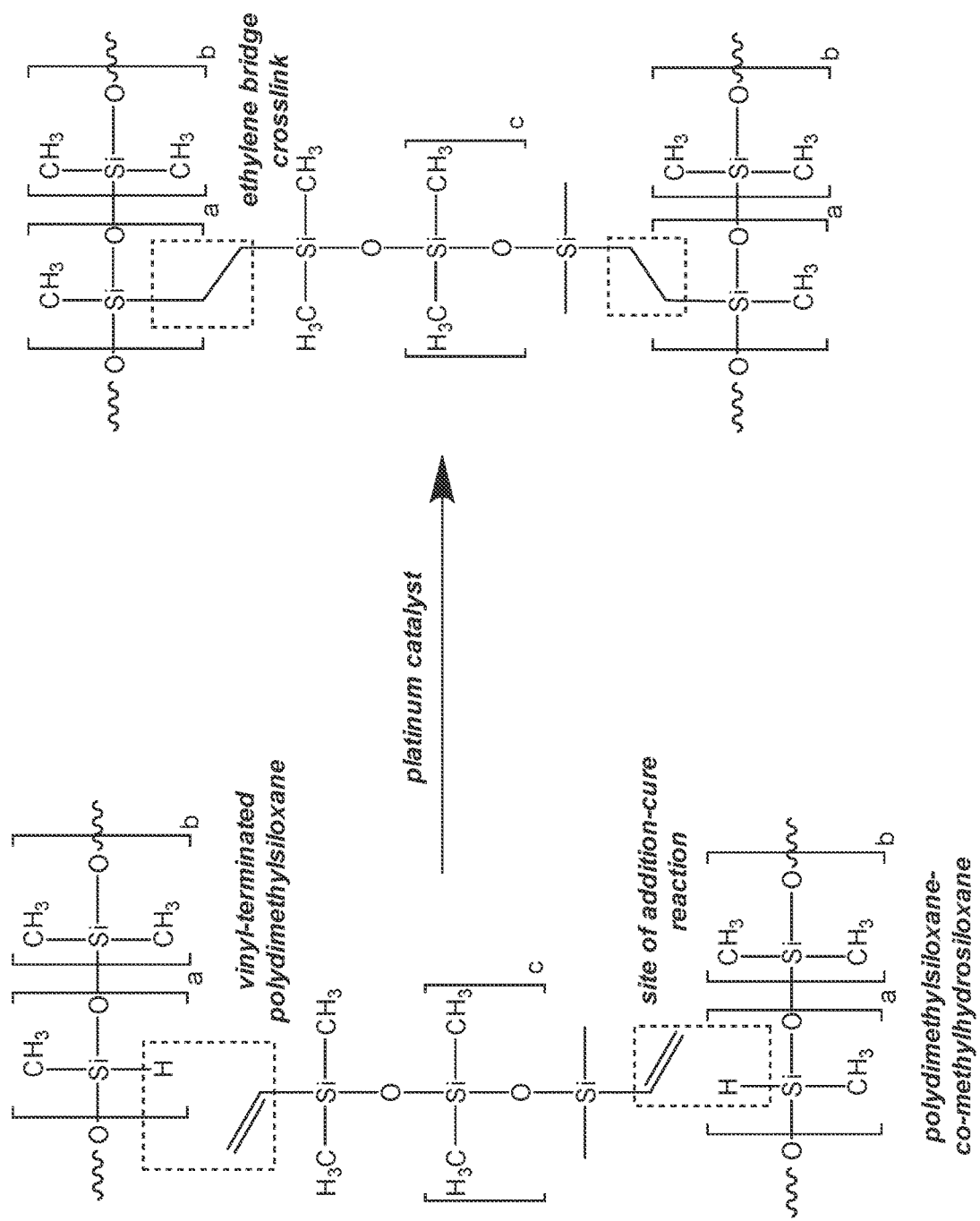
FIG. 4 is a schematic of the platinum-catalyzed reaction that forms the ring body elastomer.
Figure 5:
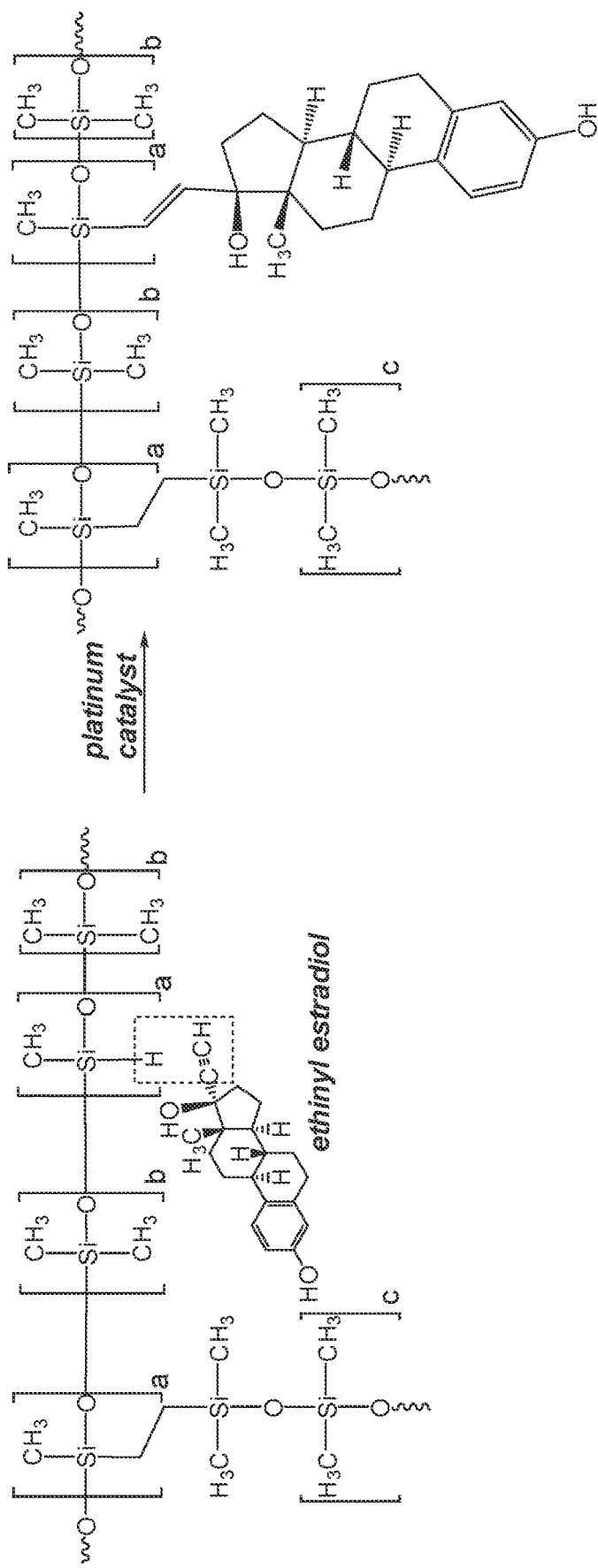
FIG. 5 is a schematic of the reaction between ethinyl estradiol and components of ring body elastomer.

Without being bound to a particular theory, it is believed that platinum dispersed throughout the ring body catalyzes a reaction between excess/unreacted hydrosilane present in the cured ring body elastomer and the terminal acetylene group in the EE as it diffuses into the ring body during maturation of the system. As this process binds the EE to the ring body elastomer, it is not available for release from the ring, causing a decrease in the recoverable amount of EE over time. This process is shown schematically in FIGS. 4 and 5. FIG. 4, for example, shows the process by which an exemplary addition-cure silicone elastomer used to prepare the ring body forms under catalytic conditions. Although this process is generally complete under the conditions described herein, the silicone elastomer resulting from the platinum catalyzed reaction results in an elastomer having platinum catalyst dispersed throughout, along with an amount of unreacted hydrosilanes present on the polymeric backbone. Without wishing to be bound by theory, it is believed that these hydrosilanes are dispersed randomly throughout the ring body, along with the platinum catalyst, which is more evenly dispersed as it is not believed to be linked to the polymer itself. EE, some of which is dissolved in the core, and some of which dissolves into the core over the life of the vaginal system, migrates from the core through the ring body. The majority of the EE migrates successfully out of the ring body into a subject's vagina and provides EE over the course of multiple product-use cycles. However, a certain number of EE molecules interact with both the platinum catalyst dispersed throughout the ring body and a hydrosilane, resulting in the structure shown in FIG. 5.

To determine if the amount of residual hydride in ring body elastomer contributed to this phenomenon, the effect of the hydride/vinyl ratio of the uncured elastomer on the in vitro release of EE on Day 1 at 6 months and at 12 months was studied. The results showed that higher hydride/vinyl ratios (>1:1) provided lower Day 1 EE releases than lower (<1:1) hydride/vinyl ratios. Surprisingly, Applicants discovered that hydride/vinyl ratios <1 led to EE "bursts" which provided unacceptably high Day 1 releases at 6 months and 12 months. Alternatively, hydride/vinyl ratios from approximately 1:1 to approximately 1.3:1 provided acceptable EE release profiles over the same period of time.

In some embodiments, a hydride/vinyl ratio of <1:1 provides a Day 1 release after six months of storage at 25° C. and 60% relative humidity from approximately 25% to approximately 85% higher than the Day 1 release prior to storage. In some embodiments, a hydride/vinyl ratio of <1:1 provides a Day 1 release after six months of storage at 25° C. and 60% relative humidity from approximately 25% to approximately 80% higher than the Day 1 release prior to storage. In some embodiments, a hydride/vinyl ratio of <1:1 provides a Day 1 release after six months of storage at 25° C. and 60% relative humidity from approximately 30% to approximately 75% higher than the Day 1 release prior to storage. In some embodiments, a hydride/vinyl ratio of <1:1 provides a Day 1 release after six months of storage at 25° C. and 60% relative humidity from approximately 35% to approximately 65% higher than the Day 1 release prior to storage. In some embodiments, a hydride/vinyl ratio of <1:1 provides a Day 1 release after six months of storage at 25° C. and 60% relative humidity from approximately 35% to approximately 60% higher than the Day 1 release prior to storage. In some embodiments, a hydride/vinyl ratio of <1:1 provides a Day 1 release after six months of storage at 25° C. and 60% relative humidity from approximately 35% to approximately 55% higher than the Day 1 release prior to storage. In some embodiments, a hydride/vinyl ratio of <1:1 provides a Day 1 release after six months of storage at 25° C. and 60% relative humidity from approximately 35% to approximately 50% higher than the Day 1 release prior to storage. In some embodiments, a hydride/vinyl ratio of <1:1 provides a Day 1 release after six months of storage at 25° C. and 60% relative humidity from approximately 40% to approximately 45% higher than the Day 1 release prior to storage.

In some embodiments, a hydride/vinyl ratio of >1:1 provides a Day 1 release after six months of storage at 25° C. and 60% relative humidity from approximately 15% lower to approximately 25% higher than the Day 1 release prior to storage. In some embodiments, a hydride/vinyl ratio of >1:1 provides a Day 1 release after six months of storage at 25° C. and 60% relative humidity from approximately 10% lower to approximately 20% higher than the Day 1 release prior to storage. In some embodiments, a hydride/vinyl ratio of >1:1 provides a Day 1 release after six months of storage at 25° C. and 60% relative humidity from approximately 5% lower to approximately 15% higher than the Day 1 release prior to storage. In some embodiments, a hydride/vinyl ratio of >1:1 provides a Day 1 release after six months of storage at 25° C. and 60% relative humidity from approximately 2% lower to approximately 19% higher than the Day 1 release prior to storage. In some embodiments, a hydride/vinyl ratio of >1:1 provides a Day 1 release after six months of storage at 25° C. and 60% relative humidity from approximately 1% to approximately 15% higher than the Day 1 release prior to storage. In some embodiments, a hydride/vinyl ratio of >1:1 provides a Day 1 release after six months of storage at 25° C. and 60% relative humidity from approximately 1% to approximately 10% higher than the Day 1 release prior to storage. Thus, and unexpectedly, some hydrosilation of EE appears to be necessary in order to achieve an acceptable EE release profile over the course of the thirteen product-use cycles.

What is more, it has been surprisingly discovered that when using NuSil™ MED4-4224, a 10:1 ratio of component parts A and B must have a narrow range of hydride/vinyl ratio to obtain consistent release of EE throughout the thirteen product-use cycles. In certain embodiments, this hydride/vinyl ratio can be from approximately 1:2 to approximately 5:1. In some embodiments, the hydride/vinyl ratio is from approximately 1:1.5 to approximately 4:1. In some embodiments, the hydride/vinyl ratio is from approximately 1:1.5 to approximately 3:1. In some embodiments, the hydride/vinyl ratio is from approximately 1:1.5 to approximately 2:1. In some embodiments, the hydride/vinyl ratio is from approximately 1:1.5 to approximately 1.5:1. In some embodiments, the hydride/vinyl ratio is from 1:1 to 1.3:1. In some embodiments, the hydride/vinyl ratio is from 1:1 to 1.2:1. Hydride to vinyl ratio can be adjusted by specifying the amount of vinyl-terminated dimethylsiloxanes and dimethylsilicones in the pre-cured elastomer when ordering.

As previously discussed, there are additional factors that contribute to the amount of EE that is released from the system on Day 1 of each product-use cycle. Particle size of the EE influences the rate at which the compound solubilizes into the core and ultimately affects the release profile of the drug from the system. In addition, it was surprisingly discovered that the temperature and relative humidity at which the EE-containing core is cured affects the amount of EE released on Day 1. Cure temperatures of 120° C. provided unacceptably excessive release amounts. Humidity levels also caused unpredictable effects as certain cure temperatures required lower relative humidity to ensure an acceptable amount of EE release on Day 1.

The combination of particle size, conditions at which the core is cured, and hydride/vinyl ratio in the ring body elastomer all contribute to the rate of EE release from the vaginal system over the thirteen product-use cycles and also contribute to the system's stability over extended periods of time. Thus, each of these factors must be harmonized to ensure a proper release profile over the thirteen product-use cycles and to ensure proper long-term stability. Too much hydride within the ring body elastomer reduces the amount of EE that is available in the system, particularly after long-term storage. Conversely, too little hydride, high cure temperatures, and high humidity during core curing provides excessively high bursts of EE on Day 1.

The vaginal system disclosed herein is reusable for thirteen product-use cycles and is sufficiently stable for at least 18 months of storage at 25° C. and at 60% relative humidity. In certain embodiments, approximately 80 to approximately 95% of EE incorporated into the system during manufacture can be recovered from the system after approximately 6 to approximately 18 months of storage at a temperature of 25° C. and at 60% relative humidity. In some embodiments, approximately 81 to approximately 94% of EE incorporated into the system during manufacture can be recovered from the system after approximately 6 to approximately 18 months of storage at a temperature of 25° C. and at 60% relative humidity. In some embodiments, approximately 82 to approximately 93% of EE incorporated into the system during manufacture can be recovered from the system after approximately 6 to approximately 18 months of storage at a temperature of 25° C. and at 60% relative humidity. In some embodiments, approximately 83 to approximately 92% of EE incorporated into the system during manufacture can be recovered from the system after approximately 6 to approximately 18 months of storage at a temperature of 25° C. and at 60% relative humidity. In some embodiments, approximately 84 to approximately 91% of EE incorporated into the system during manufacture can be recovered from the system after approximately 6 to approximately 18 months of storage at a temperature of 25° C. and at 60% relative humidity. In some embodiments, approximately 85 to approximately 90% of EE incorporated into the system during manufacture can be recovered from the system after approximately 6 to approximately 18 months of storage at a temperature of 25° C. and at 60% relative humidity.

In certain embodiments, approximately 80 to approximately 90% of EE incorporated into the system during manufacture can be recovered from the system after approximately 6, approximately 7, approximately 8, approximately 9, approximately 10, approximately 11, approximately 12, approximately 13, approximately 14, approximately 15, approximately 16, approximately 17, or approximately 18 months of storage at a temperature of 25° C. and at 60% relative humidity. In particular embodiments, approximately 80 to approximately 90% of the EE incorporated into the system during manufacture can be recovered from the system after approximately 6, approximately 12, and/or approximately 18 months of storage at a temperature of 25° C. and at 60% relative humidity. In some embodiments, approximately 80 to approximately 90% of EE incorporated into the system during manufacture can be recovered from the system after approximately 6 to approximately 9 months of storage at a temperature of 25° C. and at 60% relative humidity. In some embodiments, approximately 80 to approximately 90% of EE incorporated into the system during manufacture can be recovered from the system after approximately 6 to approximately 12 months of storage at a temperature of 25° C. and at 60% relative humidity. In some embodiments, approximately 80 to approximately 90% of EE incorporated into the system during manufacture can be recovered from the system after approximately 6 to approximately 15 months of storage at a temperature of 25° C. and at 60% relative humidity. In some embodiments, approximately 80 to approximately 90% of EE incorporated into the system during manufacture can be recovered from the system after approximately 6 to approximately 18 months of storage at a temperature of 25° C. and at 60% relative humidity. In some embodiments, approximately 80 to approximately 90% of EE incorporated into the system during manufacture can be recovered from the system after approximately 12 to approximately 15 months of storage at a temperature of 25° C. and at 60% relative humidity. In some embodiments, approximately 80 to approximately 90% of EE incorporated into the system during manufacture can be recovered from the system after approximately 12 to approximately 18 months of storage at a temperature of 25° C. and at 60% relative humidity. In some embodiments, approximately 80 to approximately 90% of EE incorporated into the system during manufacture can be recovered from the system after approximately 15 to approximately 18 months of storage at a temperature of 25° C. and at 60% relative humidity. In still further embodiments, approximately 80 to approximately 90% of EE incorporated into the system during manufacture can be recovered from the system after approximately 18 to approximately 24 months of storage at a temperature of 25° C. and at 60% relative humidity. In yet another embodiment, approximately 80 to approximately 90% of EE incorporated into the system during manufacture can be recovered from the system after approximately 24 to approximately 30 months of storage at a temperature of 25° C. and at 60% relative humidity. And in yet another embodiment, approximately 80 to approximately 90% of EE incorporated into the system during manufacture can be recovered from the system after approximately 24 to approximately 36 months of storage at a temperature of 25° C. and at 60% relative humidity. In particular, or preferred embodiments, after 18 months of storage, a sufficient amount of EE can be recovered to ensure the release of an approximate average of 0.013 mg/day over all thirteen product-use cycles.

Although EE reaction with unreacted hydrosilane is believed to be responsible for the majority of unrecovered EE over any of the periods of time specified above, both EE and SA are susceptible to degradation over any of the periods of time noted above. As a result, the ring body and cores can contain a certain quantity of degradation products including, but not limited to, 6α-OH-EE, 6β-OH-EE, 6α-OH-NES, 6β-OH-NES, 17β-estradiol, NES ST-alcohol, NES iso-ST-alcohol, 6,7-didehydro-EE & 9,11-didehydro-EE, estrone, $\Delta^6$-NES, Iso-NES, 3-enolacetate-NES, and 3-methoxy-NES. Structures of these compounds are shown in FIGS. 10A-10D. That said, and in certain embodiments, the total percentage of EE and SA degradation products after 18 months of storage is detectable but not more than 5% as measured by HPLC (i.e. Liquid Chromatography Area Percent or "LCAP"). In certain embodiments, the total percentage of EE and SA degradation products after 18 months of storage is detectable but not more than 4 LCAP. In some embodiments, the total percentage of EE and SA degradation products after 18 months of storage is detectable but not more than 3 LCAP. In some embodiments, the total percentage of EE and SA degradation products after 18 months of storage is detectable but not more than 2 LCAP. In some embodiments, the total percentage of EE and SA degradation products after 18 months of storage is detectable but not more than 1 LCAP. Example 8 describes the procedure for determining the percentage of degradation products.

In certain embodiments, the total percentage of EE and SA degradation products after 24 months of storage is detectable but not more than 5 LCAP. In certain embodiments, the total percentage of EE and SA degradation products after 24 months of storage is detectable but not more than 4 LCAP. In some embodiments, the total percentage of EE and SA degradation products after 24 months of storage is not more than 3 LCAP. In some embodiments, the total percentage of EE and SA degradation products after 24 months of storage is detectable but not more than 2 LCAP. In some embodiments, the total percentage of EE and SA degradation products after 24 months of storage is detectable but not more than 1 LCAP.

In certain embodiments, the total percentage of EE and SA degradation products after 36 months of storage is detectable but not more than 5 LCAP. In certain embodiments, the total percentage of EE and SA degradation products after 36 months of storage is detectable but not more than 4 LCAP. In some embodiments, the total percentage of EE and SA degradation products after 36 months of storage is detectable but not more than 3 LCAP. In some embodiments, the total percentage of EE and SA degradation products after 36 months of storage is detectable but not more than 2 LCAP. In some embodiments, the total percentage of EE and SA degradation products after 36 months of storage is detectable but not more than 1 LCAP. The embodiments described herein minimize the amount of impurities contained within the vaginal system after approximately 18 to approximately 36 months of storage.

In addition to the various aspects of the vaginal ring system described herein, additional aspects of the vaginal ring system are described in U.S. patent application Ser. No. 16/265,222, the entirety of which is incorporated herein by reference, including, in particular paragraphs [0006], [0007], [0009]-[0016], [0020]-[0025], [0027]-[0038], [0040], [0062]-[0069], and claims 1-14 thereof.

The vaginal system described herein is further detailed with reference to the examples shown below. These examples are provided for the purpose of illustration only and the embodiments described herein should in no way be construed as being limited to these examples. Rather, the embodiments should be construed to encompass any and all variations which become evident as a result of the teachings provided herein.

EXAMPLES

Example 1: XRPD Studies

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. Core samples were prepared for analysis by slicing into thin disks using a razor blade. A specimen of the sample was sandwiched between 3-μm-thick films and analyzed in transmission geometry. A beam-stop, short antiscatter extension, antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror. XRPD patterns were obtained in the 2θ range ~7°-26°.

Figures labeled "Image by PatternMatch v3.0.4" were generated using unvalidated software.

Example 2: Manufacture of EE-$^{13}C_2$ Silicone Elastomer Samples for NMR Studies MED4-4224 (previously known as DDU-4331) was supplied by NuSil™ Technology LLC (Carpinteria, Calif., USA). Non-micronised 17α-ethinyl-$^{13}C_2$-estradiol (20,21-$^{13}C_2$ labelled; 99.1% isotopic enrichment) (EE-$^{13}C_2$) was purchased from Cambridge Isotope Laboratories, Inc. (Andover, Mass., USA). Particle size reduction of EE-$^{13}C_2$ was achieved by manual grinding in a mortar and pestle.

Silicone elastomer mixes without EE were prepared by intimately mixing Part A and Part B (9:1) in a DAC150 FVK-Z Speedmixer™ (3000 rpm, 30 s). EE-$^{13}C_2$-loaded (2% w/w) silicone elastomer mixes were similarly prepared except with extended speedmixing at 3000 rpm for 60 seconds to achieve a dispersion of the drug powder in the silicone elastomer. The elastomer mix was poured onto glass plates fitted with a cellulose acetate release liner and 1 mm spacers. After pouring, a second acetate release liner and glass plate were set on top and the mixture compressed to form thin viscous films. Non-medicated silicone elastomer samples were cured in an oven at 150° C. for 10 min. Despite adjustments to the cure conditions (final temperature 130° C. for >20 h), the EE-$^{13}C_2$ loaded silicone samples only partly cured to form gum-like consistency materials due to EE inhibition of the curing reaction.

Example 3: Solvent Extraction of EE from Cured EE-$^{13}C_2$ Silicone Elastomer Samples To increase detection sensitivity for any bound EE using $^{13}C$ solid state NMR, the non-bound EE fraction was extracted from the silicone elastomer sample. The elastomer samples were placed in individually labeled glass vials. $CDCl_3$ or acetone (10-40 mL, depending on EE loading) was added to each extraction flask. Flasks were sealed and stored at ambient temperature for 24 hours with periodic manual shaking. This extraction protocol was repeated three times using fresh volumes of solvent to ensure complete extraction of the non-bound EE. The elastomer samples were removed from the solvent and dried overnight by solvent evaporation in preparation for $^{13}C$ solid state NMR analysis.

Figure 6A:
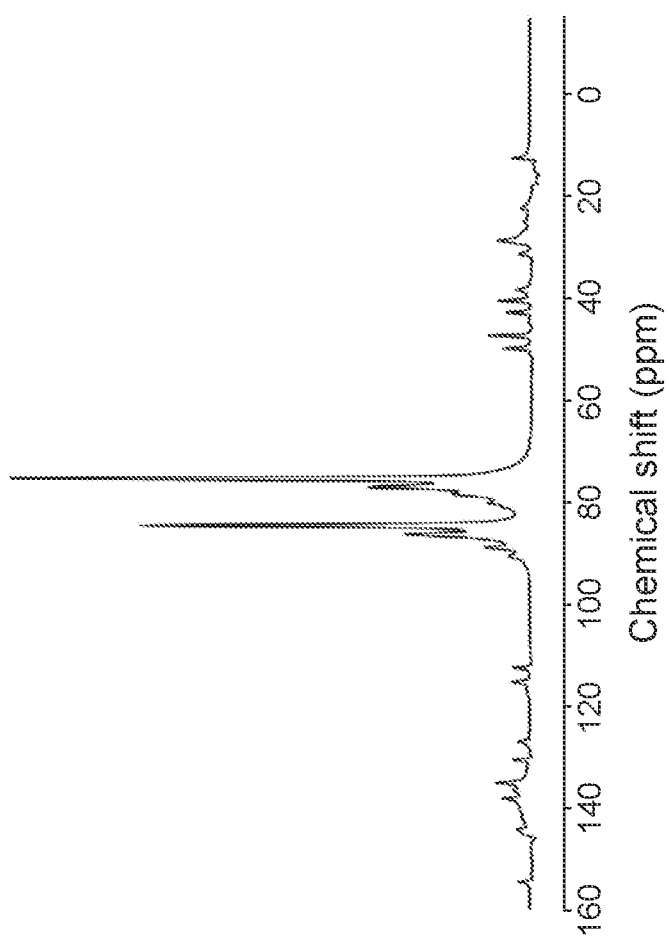
FIG. 6A is a $^{13}C$-solid state NMR spectra of 17α-ethinyl-$^{13}C_2$-estradiol (20,21-$^{13}C_2$ labelled; 99.1% isotopic enrichment)
Figure 6B:
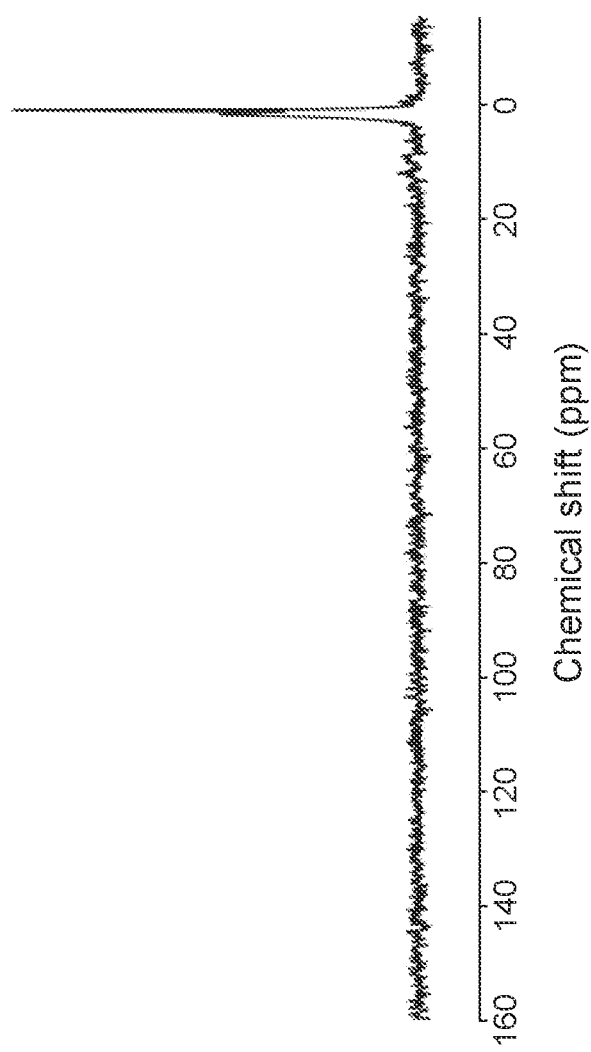
FIG. 6B is a $^{13}C$-solid state NMR spectra of NuSil™ MED4-4224 (9:1 mixture of Part A:Part B)
Figure 7A:
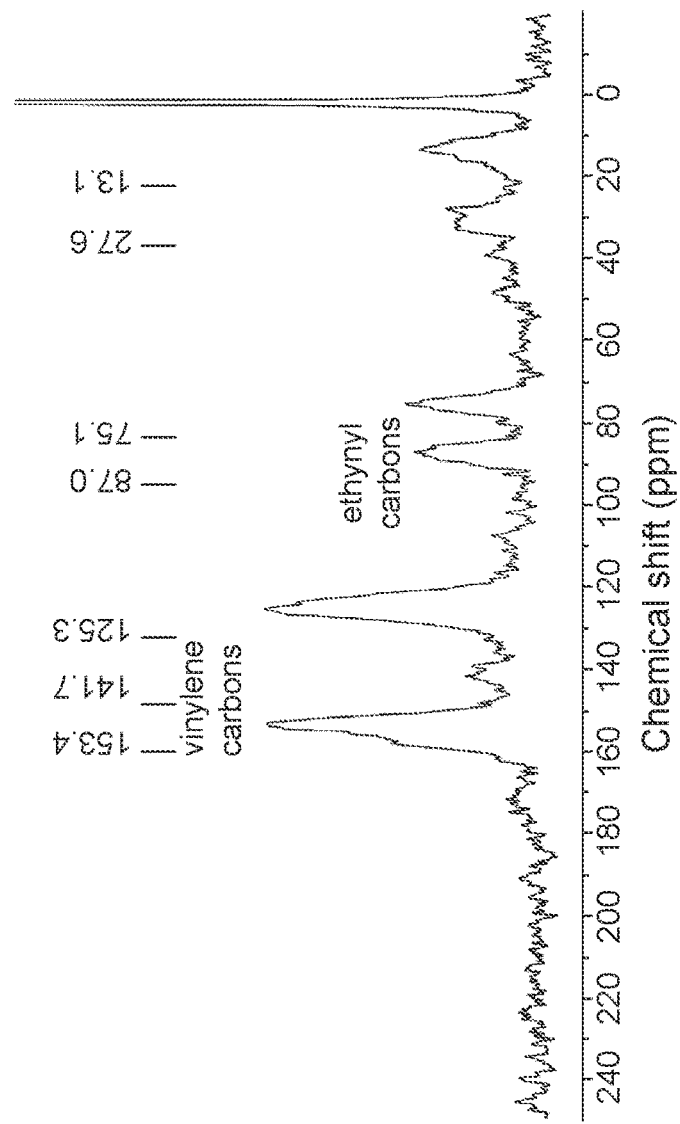
FIG. 7A is a $^{13}C$-solid state NMR spectra of an EE-$^{13}C_2$ silicone sample before solvent extraction.
Figure 7B:
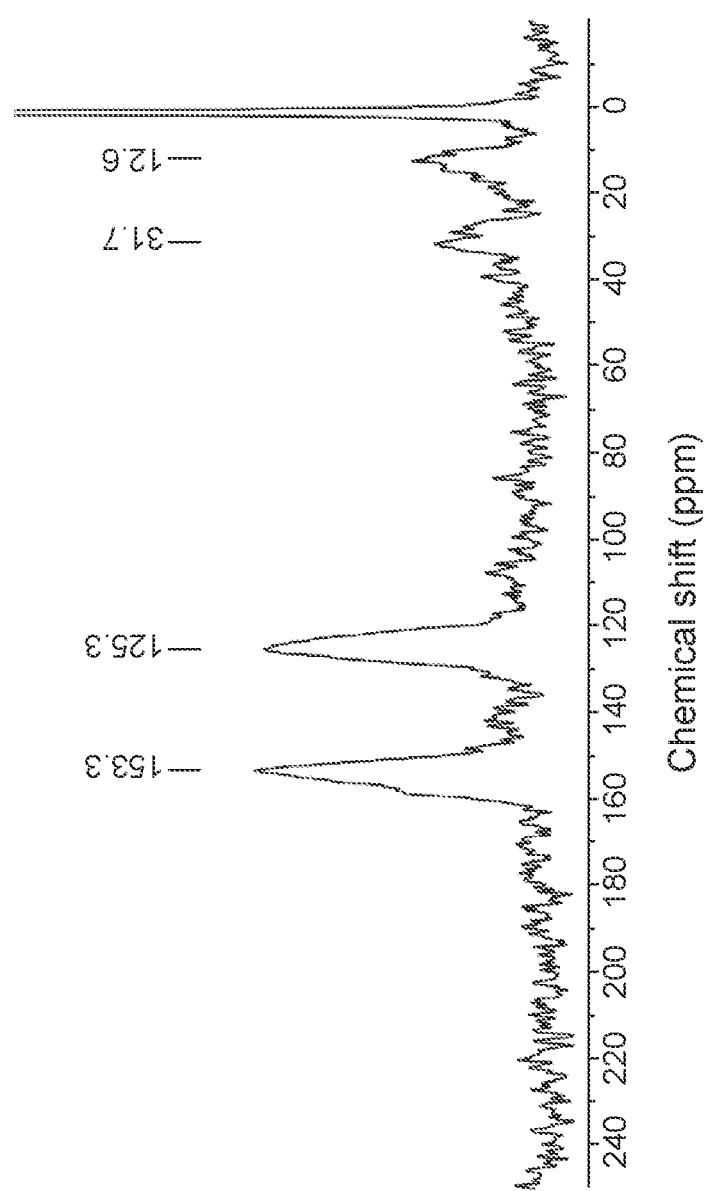
FIG. 7B is a $^{13}C$-solid state NMR spectra of an EE-$^{13}C_2$ silicone sample after solvent extraction.

Example 4: NMR Spectra of Silicone Elastomer Samples Containing EE-$^{13}C_2$ FIG. 7A shows the $^{13}C$-solid state NMR spectra for an EE-$^{13}C_2$ silicone sample before solvent extraction. The chemical shifts associated with the $^{13}C$-labelled ethynyl groups are visible at 75 and 87 ppm. A second set of intense signals are observed at 125 and 153 ppm. These signals at 125 and 153 ppm are not observed in the EE-$^{13}C_2$ or elastomer reference spectra (FIGS. 6A and 6B, respectively) and are attributed to newly-formed vinylene carbons produced from the hydrosilylation reaction between the ethynyl groups of the EE-$^{13}C_2$ and the hydrosilane groups within the silicone elastomer (FIG. 4). Analysis of the EE-$^{13}C_2$ plus elastomer material following acetone extraction showed that the ethynyl signals (75 and 87 ppm) associated with the non-bound EE-$^{13}C_2$ were no longer visible in the post-extraction sample (FIG. 7B), confirming that the non-bound EE-$^{13}C_2$ fraction had been successfully removed via solvent extraction. More interestingly, the new vinylene signals at 125 and 153 ppm were still observed and showed no reduction in intensity when compared to the non-extracted sample (FIG. 7A), clearly indicating that they could not be removed from the silicone elastomer by solvent extraction and therefore must be attributed to bound EE. Therefore, FIGS. 7A and 7B provide direct evidence for the formation of the irreversible covalent bond between the ethynyl groups of the EE-$^{13}C_2$ and the hydrosilane groups of the addition-cure silicone elastomer.

Example 5: Tensile Strength and Elongation Testing

Tensile strength and elongation testing were performed on a calibrated Stable Micro Systems TA.XTPlus texture analyzer equipped with a TEXTURE1-1 tensile rig (FIG. 8A) using a Texture Exponent 32 software program and a 50 kg (PL/CEL5) load cell. The instrument parameters used for tensile strength testing are shown in Table 1.

TABLE 1

| Instrument Settings for Tensile Strength and Elongation Analysis | |
|---|---|
| Parameters | Settings |
| T.A. settings | Cycle Until Count (Distance) |
| Test Mode | Tension |
| Load Cell | 50 kg |
| Test Speed | 8.5 mm/sec |
| Target Mode | Distance |
| Distance | 400 mm |
| Trigger Type | Auto (Force) |
| Trigger Force | 10 g |
| Number of Measurements Per Ring | 1 |
| Number of Samples (Rings) | 10 |
| Temperature | Ambient |

Ring bodies that did not contain cores were equilibrated to room temperature prior to testing. The cross-sectional diameter and internal diameter of 10 rings were measured for calculation purposes.

Figure 8B:
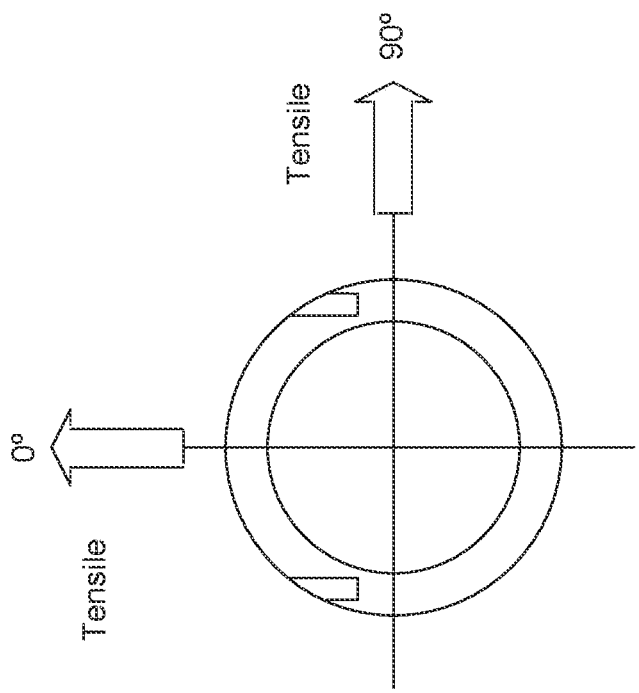
FIG. 8B is a diagram showing tensile measurement orientations parallel and perpendicular to the ring core.
Figure 8A:
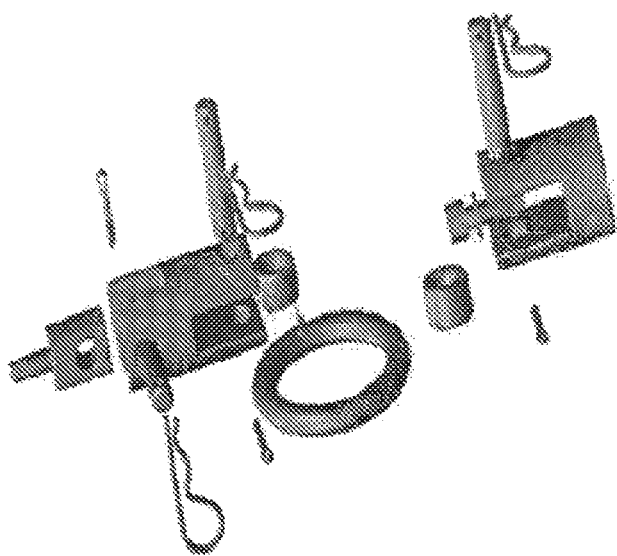
FIG. 8A is a diagram of the upper and lower rig used to measure tensile strength and elongation.
Figure 8C:
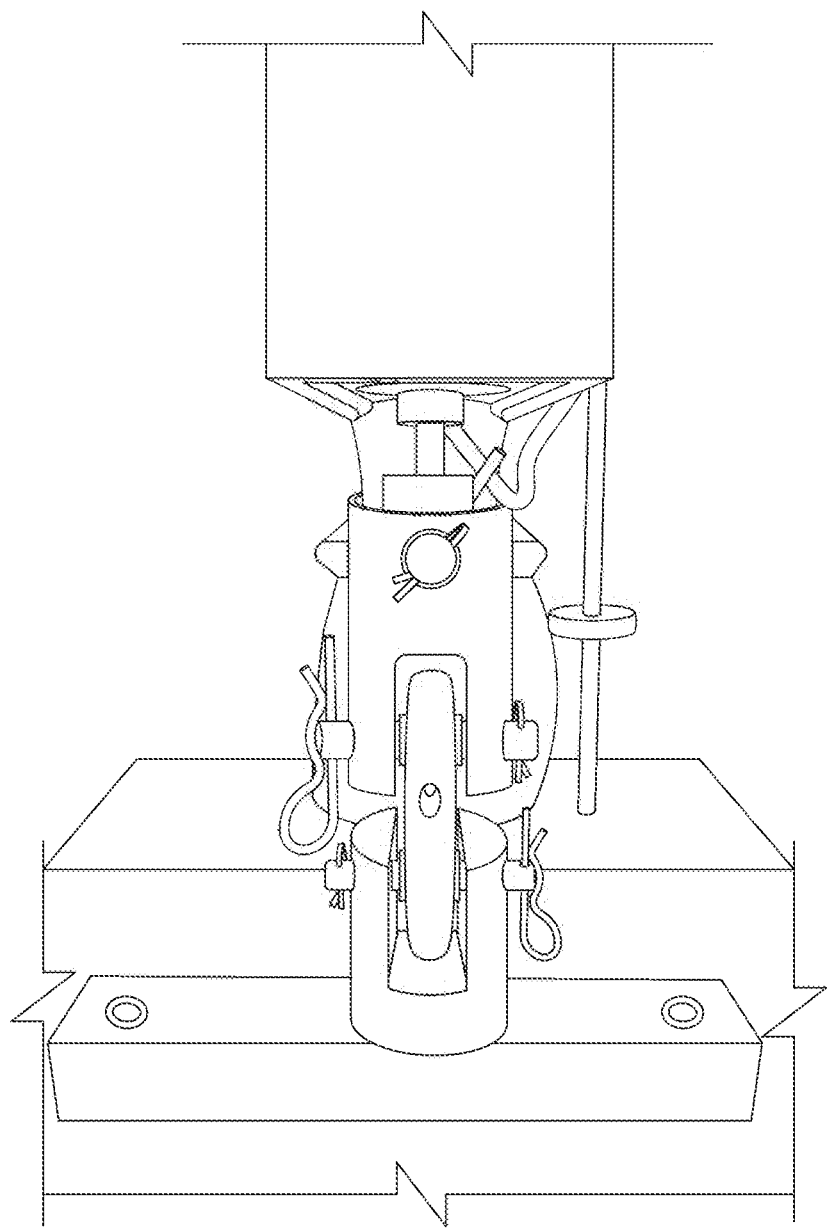
FIG. 8C shows a ring loaded for tensile strength and elongation measurement parallel to the ring cores.

Ten rings were measured parallel to the core channels, along the 0° line and ten additional rings were measured perpendicular to the core channels, along the 90° line (FIG. 8B). The instrument was started, and a 50 kg load cell was mounted on the instrument according to the procedure described in the instrument instruction manual, ensuring that the correct screws were used to attach the black rig holder to the instrument. The screws were at least 30 mm long and went completely into the countersunk holes in the rig holder (FIG. 8C). A force calibration and/or daily check were conducted according to the procedures described in the instruction manual. The upper rig was lowered to a position just above the lower rig, ensuring that the upper and lower rig were aligned. Height calibration was performed according to the procedure described in the instrument instruction manual.

For measurements parallel to the cores, a single ring was placed in the upper and lower rig according to machine instructions, with the channel opening pointing upwards. One channel opening was visible on each side of the upper rig (FIG. 8C). The measurement was performed according to instrument instructions and the process was repeated on the remaining nine rings.

Figure 8D:
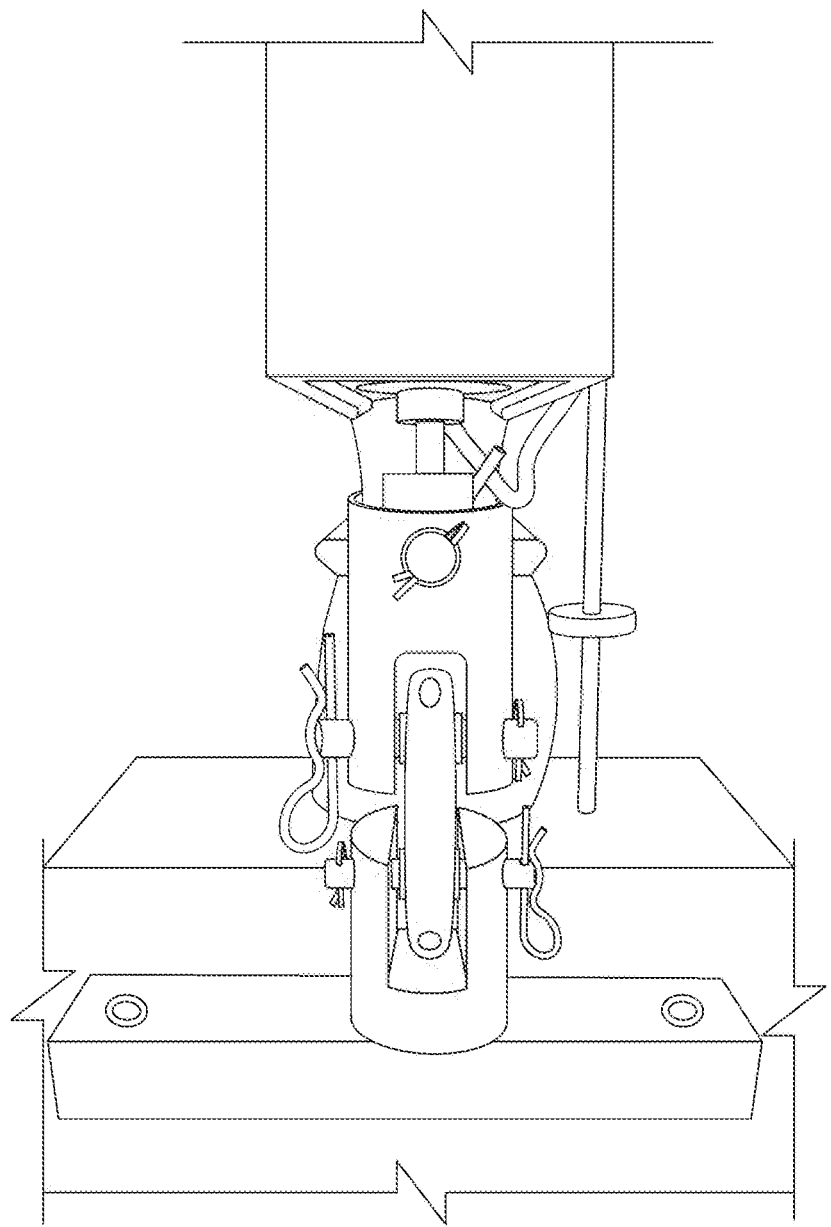
FIG. 8D shows a ring loaded for tensile strength and elongation measurement perpendicular to the ring cores.

For measurements perpendicular to the cores, a single ring was place in the upper and lower rig according to machine instructions, with the channel opening pointing outwards, towards the operator. Both channel openings were visible in the set-up (FIG. 8D). The measurement was performed according to instrument instructions and the process was repeated on the remaining nine rings.

Tensile strength, $\sigma$, was calculated for each ring according to the formula:

$$\sigma = (F \times 4) \div (2 \times \pi \times d^2)$$

wherein F is the breaking force (N) and d is the average cross-sectional diameter of the ring body (mm) measured for 10 rings.

Internal circumference of the ring, $C_{int}$ (nm) was calculated according to the formula:

$$C_{int} = d_i \times \pi$$

wherein $d_i$ is the average internal diameter of the ring (mm) measured from 10 rings as described herein.

Elongation at break, E, is calculated for each ring according to:

$$E = (2l + 2r + C_{roll} - C_{int}) \div C_{int} \times 100$$

wherein:
l is the final distance between upper and lower rig (mm);
r is the distance between the center of the rollers at height calibration (15 mm);

$C_{roll}$ is the circumference of the rollers (47 mm); and
$C_{int}$ is the internal circumference of the ring (mm).

Results of tensile strength testing are shown in Table 2. Results from elongation studies are shown in Table 3.

TABLE 2

Tensile Strength Testing Results

| Ring No. | F (N) Perpen- dicular to Cores | F (N) Parallel to Cores | Cross- Sectional Area (mm²) | Tensile Strength (σ) Perpendicular to Cores (N/mm²) | Tensile Strength (σ) Parallel to Cores (N/mm²) |
|---|---|---|---|---|---|
| 1 | 353.327 | 340.608 | 54.60 | 9645.6 | 9298.3 |
| 2 | 398.655 | 319.397 | 54.60 | 10883.0 | 8719.3 |
| 3 | 399.192 | 368.062 | 54.60 | 10897.6 | 10047.8 |
| 4 | 395.33 | 343.358 | 54.60 | 10792.2 | 9373.4 |
| 5 | 397.763 | 322.092 | 54.60 | 10858.6 | 8792.9 |
| 6 | 388.947 | 298.22 | 54.60 | 10618.0 | 8141.2 |
| 7 | 395.988 | 287.767 | 54.60 | 10810.2 | 7855.8 |
| 8 | 374.297 | 378.507 | 54.60 | 10218.0 | 10333.0 |
| 9 | 348.705 | 311.893 | 54.60 | 9519.4 | 8514.4 |
| 10 | 346.007 | 441.245 | 54.60 | 9445.7 | 12045.7 |
| Mean | 379.821 | 341.115 | 54.60 | 10368.8 | 9312.2 |
| Min | 346.007 | 287.767 | 54.60 | 9445.7 | 7855.8 |
| Max | 399.192 | 441.245 | 54.60 | 10897.6 | 12045.7 |
| SD | 22.31 | 45.37 | 0.00 | 609.15 | 1238.67 |

TABLE 3

Elongation Testing Results

| Ring No. | l (mm) Parallel to Cores | E (%) Parallel to Cores | l (mm) Perpendicular to Cores | E (%) Perpendicular to Cores |
|---|---|---|---|---|
| 1 | 289.052 | 420.2 | 301.614 | 440.2 |
| 2 | 279.900 | 405.7 | 324.448 | 476.4 |
| 3 | 301.707 | 440.3 | 320.150 | 469.6 |
| 4 | 288.697 | 419.7 | 319.627 | 468.8 |
| 5 | 277.890 | 402.5 | 328.794 | 634.6 |
| 6 | 271.784 | 392.8 | 319.377 | 468.4 |
| 7 | 259.451 | 373.2 | 322.550 | 473.4 |
| 8 | 304.030 | 444.0 | 306.151 | 447.4 |
| 9 | 273.986 | 396.3 | 292.725 | 426.1 |
| 10 | 331.482 | 487.6 | 296.655 | 432.3 |
| Mean | 287.798 | 418.2 | 313.209 | 473.7 |
| Min | 259.451 | 373.2 | 292.725 | 426.1 |
| Max | 331.482 | 487.6 | 328.794 | 634.6 |
| SD | 20.49 | 32.54 | 12.74 | 59.41 |

Example 6: Fatigue Testing

Figure 9A:
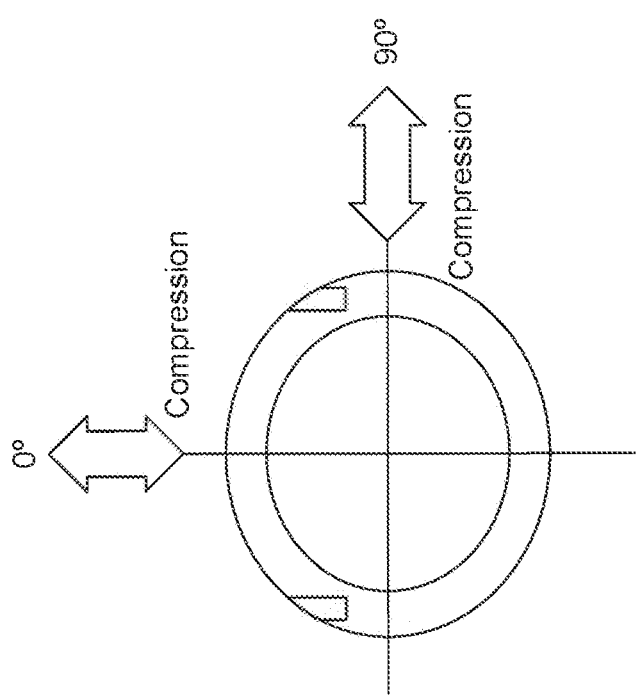
FIG. 9A is a diagram showing compression measurement orientations parallel and perpendicular to the ring core.
Figure 9B:
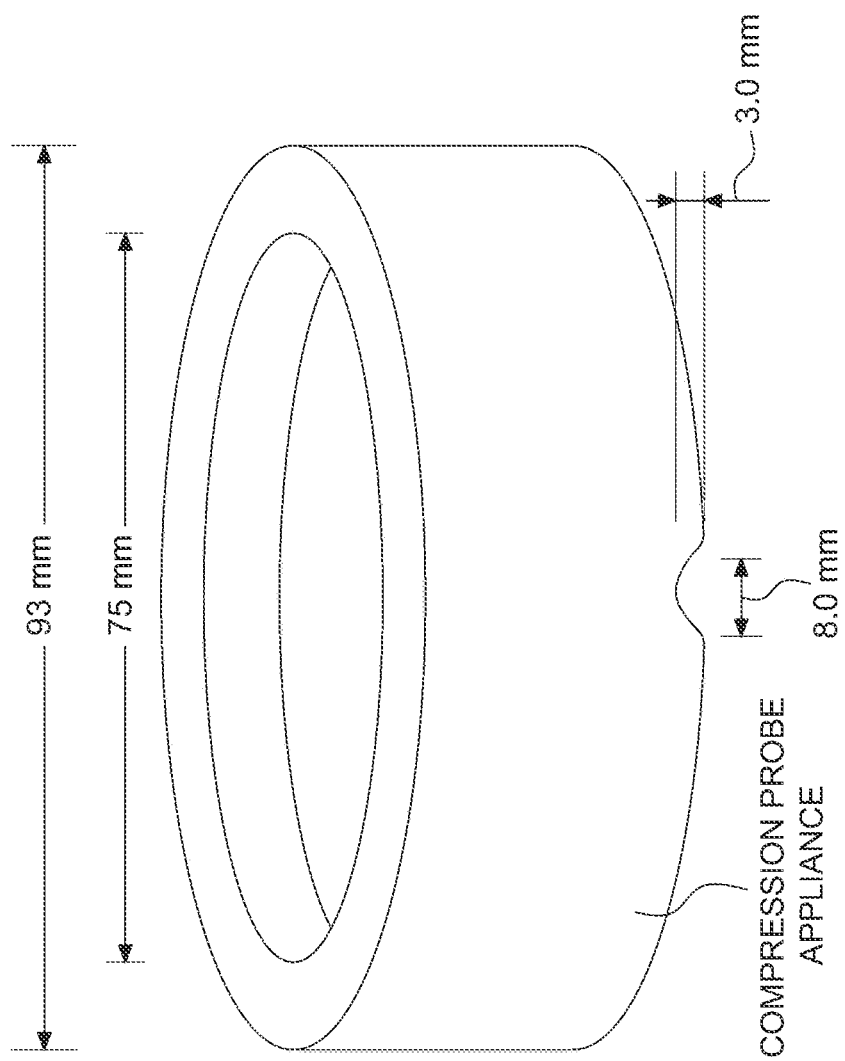
FIG. 9B is a diagram showing the compression probe appliance of the compression rig.
Figure 9C:
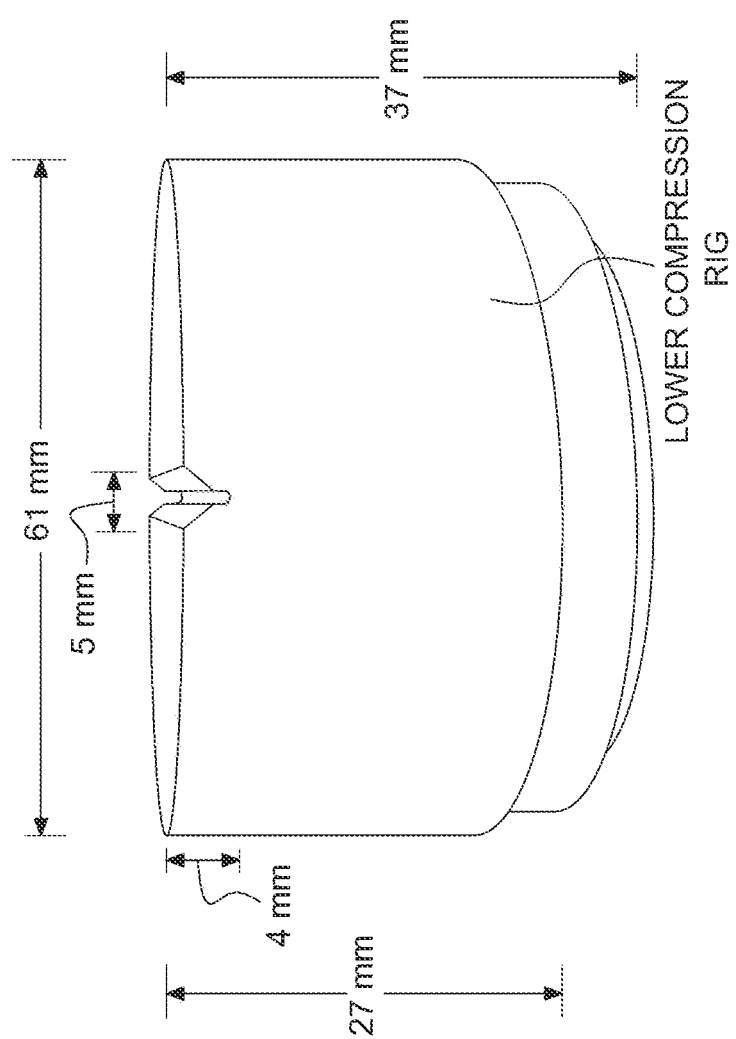
FIG. 9C is a diagram showing the lower compression rig.

Compression force, fatigue, and seal integrity testing were performed on a calibrated Stable Micro Systems TA.XTPlus texture analyzer equipped with a TEXTURE1-2 compression rig with a 9 mm slit and a lower compression rig with a 202 mm×4.8 mm nylon strap (FIGS. 9A, 9B, and 9C). A 5 kg (PL/CEL5) load cell, a 75 mm (SMS P/75) compression probe, and a heavy-duty platform (HDP/90) were used, in addition to Texture Exponent 32 software. The instrument parameters used for compression analysis are shown in Table 4.

TABLE 4

Instrument Settings for Compression Analysis

| Parameter | Setting |
|---|---|
| T.A. Setting Test Mode | Cycle Until Count (Distance) Compression |

TABLE 4-continued

Instrument Settings for Compression Analysis

| Parameter | Setting |
|---|---|
| Load Cell | 5 kg |
| Test Speed | 40.0 mm/sec |
| Pre-Test Speed | 2.0 mm/sec |
| Target Mode | Distance |
| Distance | 30.0 mm |
| Trigger Force | 0.1N |
| Number of Measurements Per Ring | 1000 |
| Number of Samples (Rings) | 10 |
| Force Limit | 10N |
| Force Range | 50N |
| Temperature | Ambient |

Figure 9D:
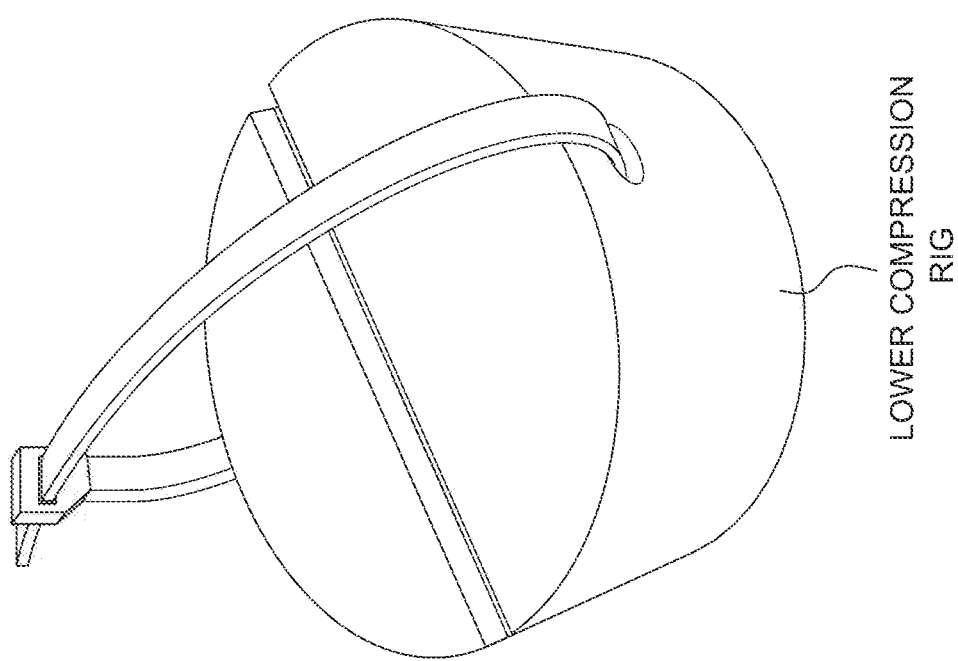
FIG. 9D is a diagram showing the lower compression rig including the nylon strap.

Ring bodies that did not contain cores were equilibrated to room temperature at least three hours prior to testing. Ten rings were measured parallel to the core channels, along the 0° line and ten additional rings were measured perpendicular to the core channels, along the 90° line (FIG. 9D). The instrument was started, and a 5 kg load cell was mounted on the instrument. The compression rig was mounted according to the instrument instruction manual. A calibration and/or daily check was performed according to the instrument instruction manual. The compression probe was lowered to just above the lower rig to make sure the slits in the probe appliance and the lower rig were aligned. Alternatively, the heavy-duty platform was adjusted to ensure alignment.

Figure 9E:
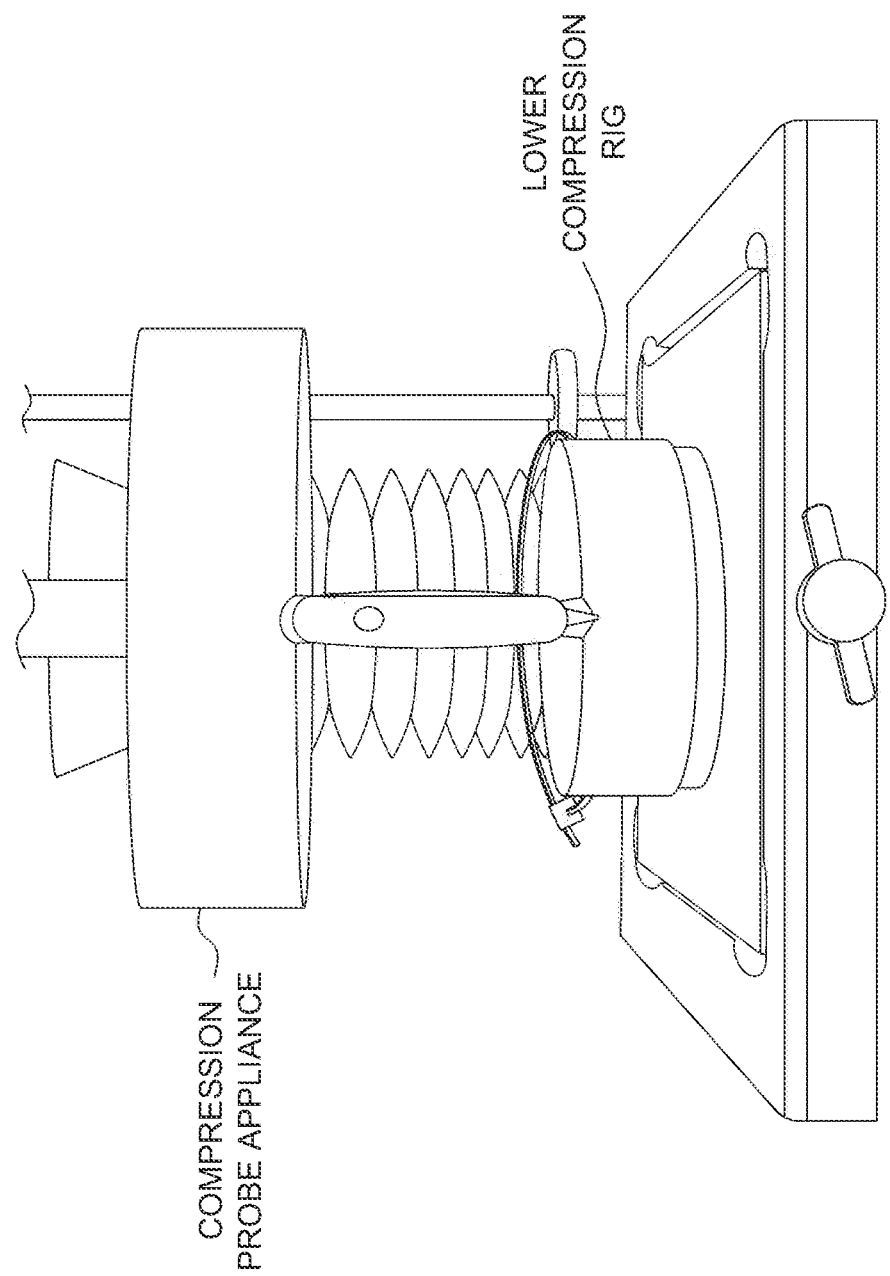
FIG. 9E shows a ring loaded for compression measurement parallel to the ring cores.

For measurement parallel to the cores, a single ring was mounted as shown in FIG. 9E and secured, with the channel opening pointing upwards and the ring fitted in the slits. The ring was secured by the strap, but it was possible to rotate it. One channel opening was visible on each side of the compression probe. It was important that the ring was mounted perpendicular to the rig. The compression plate was carefully lowered to just above the ring without compressing it. The measurement was performed, and the process was repeated on the remaining nine rings.

Figure 9F:
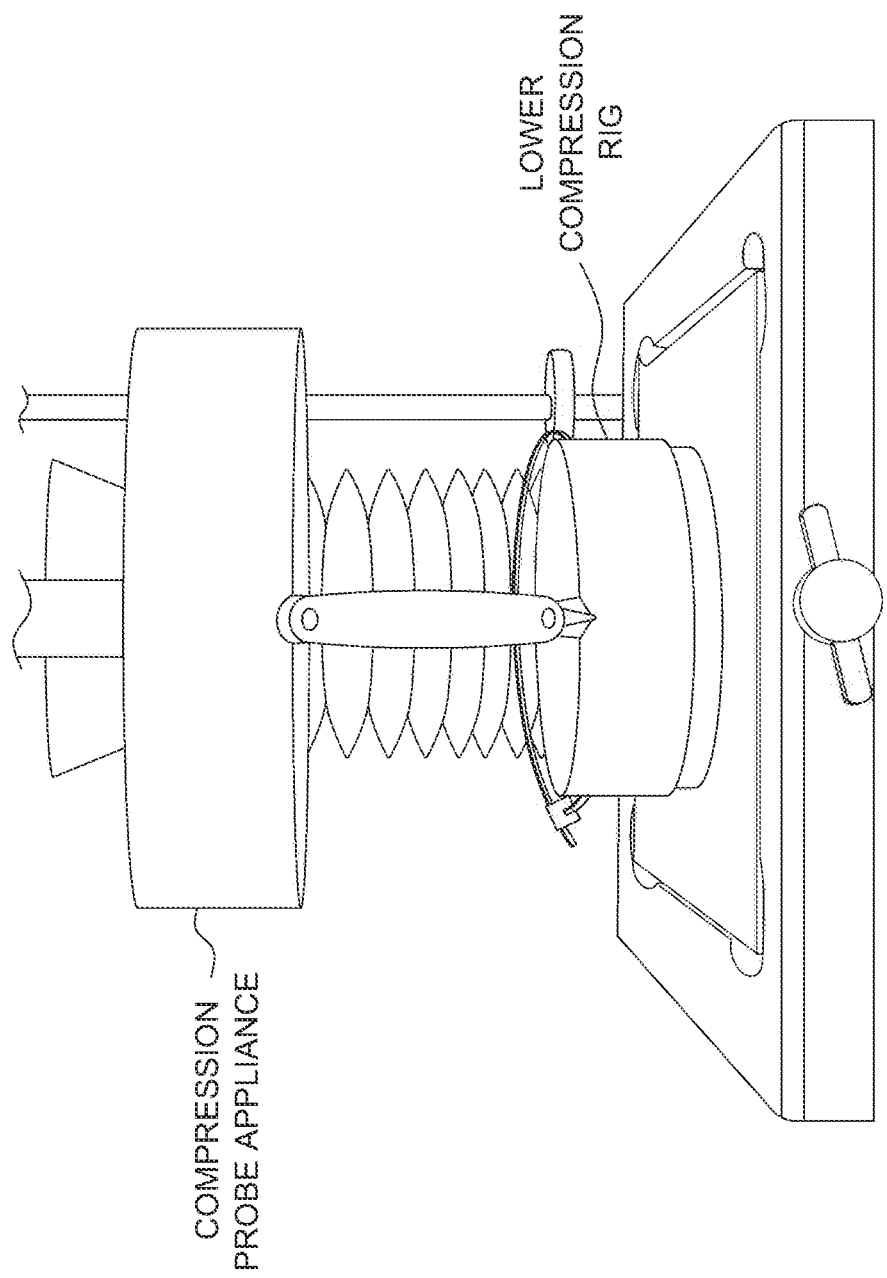
FIG. 9F shows a ring loaded for compression measurement perpendicular to the ring cores.
Figure 10D:
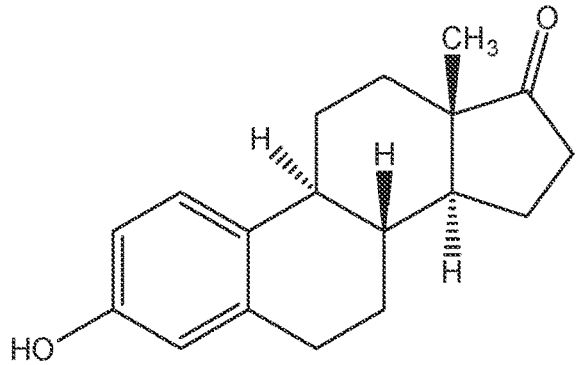
FIG. 10D shows the structures of the identified NES and EE degradation products.
Figure 10D:
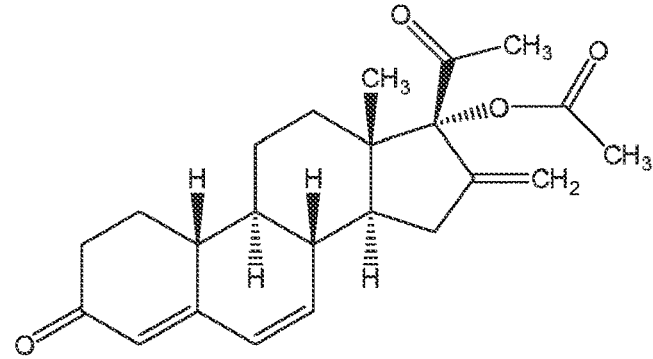
Figure 10D:
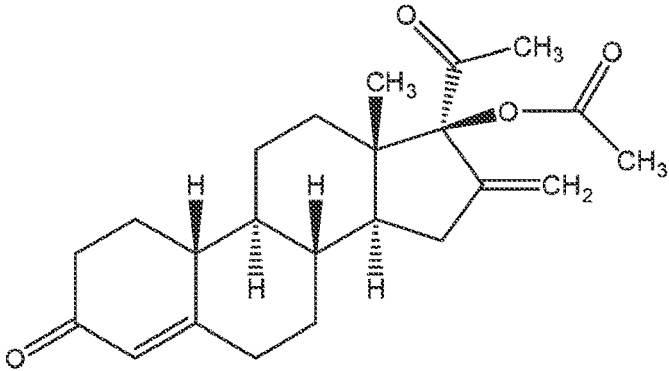

For measurement perpendicular to the cores, a single ring was mounted as shown in FIG. 9F, with the channel opening pointing outwards and the ring fitted in the slits. The ring was secured by the strap, but it was possible to rotate it. Both channel openings were visible in the set-up. It was important that the ring was mounted perpendicular to the rig. The compression probe was carefully lowered to just above the ring without compressing it. The measurement was performed, and the process was repeated on the remaining nine rings.

For each set of ten rings, the average force in Newton (N) for the $1^{st}$ compression and for the $1000^{th}$ compression was calculated.

Fatigue (percentage chain in compression force) due to cycle loading, $\Delta F_c$, was calculated for each ring according to the formula:

$$\Delta F_c = 100 \times F_{1000} \div F_1$$

wherein $F_1$ is the compression force for the $1^{st}$ compression and $F_{1000}$ is the compression force for the $1000^{th}$ compression.

No impact on seal integrity for the tested rings was noted.

Results of the fatigue testing studies are shown in Table 5.

TABLE 5

Fatigue Testing Results

| Ring No. | Force (N) After 1st Compression ($F_1$) Parallel to Cores | Force(N) After $1000^{th}$ Compression ($F_{1000}$) Parallel to Cores | $\Delta F_c$ (%) | Force (N) After 1st Compression ($F_1$) Perpendicular to Cores | Force(N) After $1000^{th}$ Compression ($F_{1000}$) Perpendicular to Cores | $\Delta F_c$ (%) |
|---|---|---|---|---|---|---|
| 1 | 4.723 | 4.468 | 94.6 | 3.907 | 3.839 | 98.3 |
| 2 | 4.746 | 4.523 | 95.3 | 3.875 | 3.799 | 98.0 |
| 3 | 4.770 | 4.508 | 94.5 | 3.845 | 3.768 | 98.0 |
| 4 | 4.747 | 4.464 | 94.0 | 3.953 | 3.862 | 97.7 |
| 5 | 4.534 | 4.319 | 95.3 | 3.951 | 3.900 | 98.7 |
| 6 | 4.691 | 4.479 | 95.5 | 3.888 | 3.837 | 98.7 |
| 7 | 5.046 | 4.768 | 94.5 | 3.955 | 3.870 | 97.9 |
| 8 | 4.723 | 4.457 | 94.4 | 3.777 | 3.693 | 97.8 |
| 9 | 4.661 | 4.467 | 95.8 | 3.801 | 3.730 | 98.1 |
| 10 | 4.799 | 4.577 | 95.4 | 3.993 | 3.926 | 98.3 |
| Mean | 4.744 | 4.503 | 94.9 | 3.895 | 3.822 | 98.1 |
| Min | 4.534 | 4.319 | 94.0 | 3.777 | 3.693 | 97.7 |
| Max | 5.046 | 4.768 | 95.8 | 3.993 | 3.926 | 98.7 |
| SD | 0.13 | 0.11 | 0.59 | 0.07 | 0.07 | 0.35 |

Example 7: Extraction Procedure to Determine Recoverable FE and NES after Storage for any Period of Time Solutions:
Diluent: methanol/water 58/42 v/v
Dried NES and EE before weighing (100-105° C. 3 h)
EE stock solution: Dissolved 25.0 mg of EE and diluted to 250.0 mL with methanol (duplicates, $EE_1$ and $EE_2$)
NES stock solution: Dissolved 50.0 mg of NES and diluted to 100.0 mL with methanol (duplicates, $NES_1$ and $NES_2$)
Standard solutions:
  S1: Diluted 5.0 mL of $NES_1$ and 4.0 mL of $EE_1$ to 50.0 mL with diluent
  S2: Diluted 6.0 mL of $NES_2$ and 5.0 mL of $EE_2$ to 50.0 mL with diluent
  S3: Diluted 8.0 mL of $NES_1$ and 7.0 mL of $EE_1$ to 50.0 mL with diluent
  S4: Diluted 10.0 mL of $NES_2$ and 9.0 mL of $EE_2$ to 50.0 mL with diluent
System suitability solution (SST solution): Diluted 5.0 mL acetone+7.0 mL $NES_1$+6.0 mL $EE_1$ to 50.0 mL with diluent.
Extraction Procedure:
  Rings were cut into 8 pieces and each piece was divided lengthwise then transferred to an Erlenmeyer flask.
  140 mL of acetone (weight of flask was noted before and after acetone addition) was added to the flask. The flask was then capped.
  The flask was shaken for 24 h at 180 rpm (weight was noted after extraction).
  Diluted 2.5 mL of the extraction medium to 25.0 mL with diluent (test solution) and a sample was subsequently pulled for HPLC analysis.
Liquid Chromatography
Column
  analytical column: Discovery C8, 5 µm, 150×4.6 mm (Supelco)
  pre-column: Supelguard, Discovery C8, 5 µm, 20×4.0 mm (Supelco)
  stationary phase: endcapped C8 (5 µm particle size) USP L7
  temperature: 30° C.
Mobile phase: methanol/water 58/42, isocratic elution
Flow rate: 1.2 mL/min
Detection (assay): NES UV 240 nm, EE UV 280 nm
Detection (identity): PDA (photodiode array detector) scanning 220-310 nm, NES 240 nm, EE 280 nm
Injection: 20 µL
Run time: 15 min
System suitability: SST solution
Area precision (n=5): RSD (%)≤2.0
Peak tailing (T): 0.8≤T≤1.5
Blank injections: No interfering peaks
Retention times: EE approximately 7 min and NES approximately 9 min
Results Assay: Report the average value of three different rings and express as mg EE/ring and mg NES/ring.
Results Content uniformity: Calculate the average value of ten different rings. Report with or without remarks according the guidelines outlined in the US Pharmacopeial Convention, incorporated herein by reference, and in particular USP <905>.
Results Identity: If the retention time in the test and standard solution match in the assay and UV spectra of EE/NES in test solution and PDA library match report without remarks, otherwise with remarks.

Example 8: Determination of SA and EE Degradation Products

References
  Ethinylestradiol (EE), working reference standard
  NESTORONE® (NES), working reference standard
  17β-estradiol (structure shown in FIG. 10B)
  Estrone estradiol (structure shown in FIG. 10D)
  Δ6-NESTORONE® estradiol (structure shown in FIG. 10D)
  NES ST-alcohol estradiol (structure shown in FIG. 10C)
Reagents
  Methanol, HPLC grade
  Acetone, p.a.
  Water, purified
  Acetonitrile, gradient grade
Solutions
  Dry NES and EE before weighing (100-105° C. 3 h)

NES stock solution: Dissolved 75.0 mg of NES and diluted to 50.0 mL with methanol (duplicates, SSA1 and SSA2)

EE stock solution: Dissolved 15.0 mg of EE and diluted to 50.0 mL with methanol (duplicates, SSB1 and SSB2)

Standard Solutions:
   S5: Diluted 5.0 mL of SSA1 and 5.0 mL of SSB1 to 50.0 mL with methanol
   S4: Diluted 7.0 mL of S5 to 10.0 mL with methanol
   S3: Diluted 2.5 mL of SSA2 and 2.5 mL of SSB2 to 50.0 mL with methanol
   S2: Diluted 5.0 mL of S5 to 50.0 mL with methanol
   S1: Diluted 5.0 mL of S3 to 50.0 mL with methanol NES area reject stock solution: Diluted 2.5 mL SSA1 to 50.0 mL with methanol (R1).

EE area reject stock solution: Diluted 2.5 mL SSB1 to 50.0 mL with methanol (R2).

NES/EE area reject solution: Diluted 1.0 mL R1+5.0 mL R2 to 100.0 mL with methanol. Rejection peak area at 254 nm: NES area. Rejection peak area at 280 nm: EE area.

System suitability solution:
   SST1: Dissolved 15.0 mg 17β-estradiol and diluted to 50.0 mL with methanol
   SST2: Dissolved 15.0 mg estrone and diluted to 50.0 mL with methanol
   SST3: Dissolved 15.0 mg Δ6-NESTORONE® and diluted to 10.0 mL with methanol
   SST4: Dissolved 15.0 mg NES ST-alcohol and diluted to 10.0 mL with methanol SST solution: Dilute 2.5 mL SSA2+5.0 mL SSB2+5.0 mL SST1+5.0 mL SST2+2.5 mL SST3+2.5 mL SST4 to 50.0 mL with methanol.

Extraction Procedure
   Cut the ring in 8 pieces and divided each piece lengthwise, transfer to Erlenmeyer flask.
   Added 70 mL of acetone (noted weight before and after), capped Erlenmeyer flask.
   Shook for 24 h at 180 rpm (noted weight after extraction).
   Transferred 10.0 mL of extraction medium to a test tube and evaporated to dryness.
   Dissolved in 1.0 mL of methanol. When a clear upper phase was obtained, transferred to LC vial (test solution)

Liquid Chromatography

Column
   analytical column: SUNFIRE™ C18, 5 μm, 250×4.6 mm (Waters)
   pre-column: SUNFIRE™ C18, 5 μm, 20×4.6 mm (Waters)
   stationary phase: reversed phase endcapped C18, 100 Å (5 μm), USP L1
   temperature: 35° C.

| Mobile Phase A: Acetonitrile, B: Water | | |
|---|---|---|
| Time (min) | Mobile Phase A (% v/v) | Mobile Phase B (% v/v) |
| 0 | 34 | 66 |
| 20 | 34 | 66 |
| 23 | 42 | 58 |
| 30 | 42 | 58 |
| 35 | 55 | 45 |
| 40 | 55 | 45 |
| 51 | 90 | 10 |
| 70 | 90 | 10 |
| 75 | 34 | 66 |
| 85 | 34 | 66 |

Flow rate: 1 mL/min
Detection (UV): NES 254 nm, EE 280 nm
Detection (PDA): scanning 220-310 nm
Injection: 10 μL
Sample temperature: 2-8° C.
Run time: 85 min
System suitability: SST solution
   Resolution
      ≥2.0 between 17β-estradiol and NES ST-alcohol at 280 nm
      ≥1.5 between EE and estrone at 280 nm
      ≥4.0 between Δ6-NESTORONE® and NES at 254 nm
   Peak tailing (T): 0.8≤T≤1.5
   Area precision (n=5): RSD (%)≤3.0 for NES peak at 254 nm, ≤3.0 for EE peak at 280 nm

| Related substance | Quantitation at [nm] | Relative Retention Time (RRT) reference | RRT 30° C. |
|---|---|---|---|
| 6α-OH-EE | 280 | 17β-estradiol | 0.28 |
| 6β-OH-EE | 280 | 17β-estradiol | 0.29 |
| 6-keto-EE | 254 | 17β-estradiol | 0.53 |
| 6α-OH-NES | 254 | 17β-estradiol | 0.60 |
| 6β-OH-NES | 254 | 17β-estradiol | 0.71 |
| 17β-estradiol | 280 | 17β-estradiol | 1.00 |
| NES ST-alcohol | 254 | 17β-estradiol | 1.04 |
| NES iso-ST-alcohol | 254 | 17β-estradiol | 1.06 |
| 6,7-didehydro-EE & 9,11-didehydro-EE | 254 | 17β-estradiol | 1.15 |
| Estrone | 280 | 17β-estradiol | 1.23 |
| Δ6-NES | 280 | NES | 0.96 |
| Iso-NES | 254 | NES | 1.13 |
| 3-enolacetate-NES | 254 | NES | 1.29 |
| 3-methoxy-NES | 254 | NES | 1.36 |

Example 9: Condom Compatibility Testing

Five different types of condoms (three latex, one polyisoprene, and one polyurethane) were tested to determine if exposure to the vaginal ring system described herein would result in detrimental effects to the condom. Condom strength was measured using four different parameters: Force required for breakage (break force), percent condom elongation at breakage (percent elongation), pressure required to cause the condom to burst (burst pressure), and the condom's volume at burst (burst volume). A baseline was established for the analysis by measuring the four parameters of the condoms in their "as-received" condition with no exposure to heat, the ring system, or any lubricants (labeled "Baseline" in Table 6, below).

To test the compatibility of the vaginal system components with the condoms, an aqueous extract was prepared by placing 20 vaginal ring systems in a sufficient amount of water to test 20 condoms and agitating the resulting mixture for 24 hours. After the 24-hour period, the vaginal ring bodies were removed and the remaining extract was saturated with segesterone acetate and ethinyl estradiol. The amounts of segesterone acetate and ethinyl estradiol needed to ensure saturation were calculated by multiplying the solubilities of segesterone acetate and ethinyl estradiol in water at neutral pH (18.5 µg/mL and 11.0 µg/mL, respectively) by the volume of extract and adding an additional 20% of each agent.

Each type of condom was then covered with the saturated extract and conditioned at 40° C. for 1 hour at which time the four parameters described above were measured (labeled "Sample" in Table 6). Two controls were also included: one where each condom was subjected to the same preparation and conditioning using water in place of the saturated extract (labeled "Control" in Table 6), and one where each condom was subjected to the same preparation and conditioning using mineral oil in place of the saturated extract (labeled "Mineral Oil" in Table 6).

As shown in Tables 6 and 7, the parameters of each condom in the "Sample" category measured within 10% of condoms in the "Control" group, illustrating that exposure to the components of the vaginal ring system did not cause detrimental effects to the condoms. In contrast, condoms exposed to the mineral oil lubricant became significantly weaker.

Table 6: Change in Condom Strength After Exposure to Vaginal Ring System Components

TABLE 7

| | Percent Changes | | | |
|---|---|---|---|---|
| Condom Type | Break Force % Change (sample vs. control) | Elongation % Changes (sample vs. control) | Burst Pressure % Change (sample vs. control) | Burst Volume % Change (sample vs. control) |
| Trojan ® Enz ® Latex (non-Lubricated) | −5.0 | 2.7 | 0.0 | −2.3 |
| LifeStyles ® Latex (non-(Lubricated) | 2.1 | 0.0 | −2.4 | −0.5 |
| Atlas ® Latex (non-Lubricated) | −5.7 | −1.7 | −0.3 | −3.9 |
| LifeStyles ® Skyn ® Polyisoprene (Lubricated) | −3.3 | −0.4 | −3.9 | −3.4 |
| Trojan Supra ® Polyurethane (Lubricated) | 2.0 | 0.9 | −2.2 | −1.5 |

Percent change in Table 7 was calculated using the formula % change=100*(sample mean value−control mean value)/Control mean value

Example 10: Pharmacodynamics

Cardiac Electrophysiology

The effect of SA on the QTc interval was evaluated in a Phase 1 randomized, placebo and positive controlled, double-blind, single-dose, three-period, crossover thorough QTc study in 44 healthy adult female subjects. At the single intravenous bolus dose which produces 4.5-fold the thera-

TABLE 6

Change in Condom Strength After Exposure to Vaginal Ring System Components

| Condom Type | Exposure | Break Force in Newtons (N) and Standard Deviation (SD) | | Percent Elongation at Break (%) and Standard Deviation (SD) | | Burst Pressure in Kilopascals (kPa) and Standard Deviation (SD) | | Burst Volume in Liters (L) and Standard Deviation (SD) | |
|---|---|---|---|---|---|---|---|---|---|
| | | (N) | SD | (%) | SD | (kPa) | SD | (L) | SD |
| Trojan ® Enz ® Latex (non-Lubricated) | Baseline | 103.7 | 6.8 | 880.0 | 17.3 | 2.0 | 0.2 | 32.7 | 3.2 |
| | Control | 94.4 | 13.4 | 852.0 | 30.0 | 1.9 | 0.1 | 36.6 | 3.0 |
| | Mineral Oil | 4.7 | 1.1 | 326.0 | 85.0 | 0.9 | 17.7 | 0.1 | 9.8 |
| | Sample | 89.7 | 8.9 | 875.0 | 25.6 | 1.9 | 0.1 | 35.8 | 2.3 |
| LifeStyles ® Latex (non-(Lubricated) | Baseline | 86.3 | 9.7 | 792.0 | 21.0 | 2.3 | 0.2 | 38.5 | 3.1 |
| | Control | 78.0 | 8.8 | 795.0 | 25.5 | 2.3 | 0.2 | 40.3 | 3.8 |
| | Mineral Oil | 12.0 | 5.0 | 542.0 | 138.1 | 1.1 | 0.2 | 27.6 | 6.7 |
| | Sample | 79.6 | 10.2 | 795.0 | 21.1 | 2.2 | 0.2 | 40.1 | 3.6 |
| Atlas ® Latex (non-Lubricated) | Baseline | 88.4 | 8.0 | 873.0 | 22.6 | 2.0 | 0.1 | 34.6 | 3.3 |
| | Control | 85.9 | 6.1 | 893.0 | 15.4 | 2.0 | 0.1 | 36.7 | 3.8 |
| | Mineral Oil | 12.3 | 5.0 | 556.0 | 174.4 | 0.8 | 0.1 | 17.4 | 8.3 |
| | Sample | 81.0 | 7.5 | 878.0 | 21.9 | 2.0 | 0.1 | 35.2 | 3.1 |
| LifeStyles ® Skyn ® Polyisoprene (Lubricated) | Baseline | 85.7 | 13.7 | 1033.0 | 31.5 | 1.8 | 0.1 | 46.8 | 2.8 |
| | Control | 80.9 | 10.5 | 1017.0 | 23.5 | 1.8 | 0.1 | 46.9 | 2.4 |
| | Mineral Oil | 24.6 | 9.6 | 781.0 | 131.5 | 0.7 | 0.0 | 13.9 | 2.1 |
| | Sample | 78.2 | 13.0 | 1013.0 | 29.5 | 1.7 | 0.2 | 45.3 | 3.8 |
| Trojan Supra ® Polyurethane (Lubricated) | Baseline | 46.1 | 10.8 | 539.0 | 17.1 | 9.8 | 0.9 | 7.6 | 0.6 |
| | Control | 44.7 | 7.8 | 532.0 | 13.9 | 9.3 | 0.9 | 8.7 | 0.9 |
| | Mineral Oil | 35.5 | 6.6 | 528.0 | 14.6 | 6.6 | 0.80 | 7.9 | 0.6 |
| | Sample | 45.6 | 12.1 | 537.0 | 20.2 | 9.1 | 0.6 | 8.6 | 0.6 | peutic serum concentrations of SA achieved with the vaginal system, SA did not prolong the QTc interval to any clinically relevant extent.

Example 11: Pharmacokinetics

Absorption

The pharmacokinetics (PK) of the vaginal system described herein were determined in 39 women who used the system for up to 13 product-use cycles. Following vaginal administration, SA and EE were absorbed into systemic circulation with median Tmax of about 2 hours in product-use cycle 1, product-use cycle 3, and product-use cycle 13. Concentrations of both components declined after Tmax and became more constant after 96 hours post-dose. Over subsequent product-use cycles, the peak serum concentrations of SA and EE declined. Serum concentration-time profiles of SA and EE for product-pse cycles 1, 3, and 13 of system use are provided in FIG. 1 and FIG. 2 with PK parameters summarized in Table 8 and Table 9.

TABLE 8

Mean (SD) PK Parameters for SA following Administration

| Cycle | $AUC_{0-21day}$ (ng * hr/mL) | $AUC_{0-1\ day}$ (ng * hr/mL) | $C_{max}$ (pg/mL) | $C_{avg}$ (pg/mL) |
|---|---|---|---|---|
| 1 | 96.2 (16.9) | 15 (3.2) | 1,147 (315) | 191 (34) |
| 3 | 65.9 (14.8) | 5 (1.6) | 363 (133) | 131 (29) |
| 13 | 47.2 (10.1) | 3.9 (1.4) | 294 (116) | 94 (20) |

TABLE 9

Mean (SD) PK Parameters for EE following Administration

| Cycle | $AUC_{0-21day}$ (ng * hr/mL) | $AUC_{0-1\ day}$ (ng * hr/mL) | $C_{max}$ (pg/mL) | $C_{avg}$ (pg/mL) |
|---|---|---|---|---|
| 1 | 22.2 (9.8) | 2.1 (0.7) | 129 (39) | 44 (19) |
| 3 | 14.7 (4.7) | 0.9 (0.4) | 60 (32) | 29 (9) |
| 13 | 9.6 (4.1) | 0.7 (0.3) | 39 (16) | 19 (8) |

The volume of distribution of SA is 19.6 L/kg. SA is approximately 95% bound to human serum proteins and has negligible binding affinity for sex hormone-binding globulin (SHBG). EE is highly protein bound but not specifically bound to serum albumin (98.5%) and induces an increase in the serum concentrations of SHBG.

Metabolism

In vitro data show that both SA and EE are metabolized by the cytochrome P450 (CYP) 3A4 isoenzyme. In human serum, two oxidative metabolites (5α-dihydro- and 17α-hydroxy-5αdihydro metabolites) constitute 50% of exposure relative to SA. Both metabolites are not considered as active metabolites with $EC_{50}$ to progesterone receptor 10-fold higher than that of SA. EE is primarily metabolized by aromatic hydroxylation, but a wide variety of hydroxylated and methylated metabolites are formed. These are present as free metabolites and as sulfate and glucuronide conjugates. The hydroxylated EE metabolites have weak estrogenic activity.

Excretion

The mean (SD) half-life of SA is 4.5 (3.4) hours. EE is known to be excreted in the urine and feces as glucuronide and sulfate conjugates, and it undergoes enterohepatic recirculation. The mean (SD) half-life of EE is 15.1 (7.5) hours.

The in vitro studies suggest that SA is unlikely to inhibit or induce CYP enzymes at the therapeutic dose.

Example 12: Clinical Trials

The clinical trials that evaluated the safety of the vaginal system described herein were obtained from three 13-cycle trials. One trial was conducted entirely in the U.S. (15 sites), and the other two were global studies that included 5 U.S. sites and 7 international sites (Australia, Brazil, Chile, Dominican Republic, Finland, Hungary, Sweden). All three trials were open label and enrolled healthy females, desiring contraception, 18 to 40 years of age. At about 50% enrollment, females with BMI>29 kg/m² were excluded due to the occurrence of two VTEs in this subgroup. In total, 2,308 females contributed 21,590 product-use cycles of exposure for safety evaluation and 999 completed 13 product-use cycles; there were 209 subjects with BMI>29 kg/m² who contributed 1,254 product-use cycles of exposure with 36 subjects completing 13 product-use cycles. The demographic profile for subjects was: mean age 26.7 years, mean BMI 24.1 (16.0-41.5) kg/m²; 67% were from the U.S. The racial distribution was 71% Caucasian, 14% African American, 4% Asian, and 11% Other; 30% of the population was Hispanic.

The efficacy of the system was evaluated in two 1-year multicenter trials enrolling 2,265 females, age 18-40 years, who were healthy and sexually active with regular menstrual periods. The trials were conducted in the U.S., Dominican Republic, Brazil, Chile, Finland, Hungary, Sweden, and Australia, with 67.1% of females from the U.S. The racial/ethnic distribution was Caucasian (71.2%), African-American (14.1%), Asian (3.5%), other/multiple races (11.2%); 28.7% of the study population was Hispanic. The mean age was 26.7 years and the mean (range) BMI was 24.1 (16.0, 41.5) kg/m². At approximately 50% enrollment, women with BMI>29.0 kg/m² were no longer enrolled in the two trials and all women with a BMI>29.0 kg/m² were discontinued from the trials.

Based on pooled data from the two trials, 2,111 females ≤35 years of age completed 17,427 evaluable 28-day product-use cycles (cycles in which no back-up contraception was used). The pooled pregnancy rate, evaluated by the Pearl Index (PI), was 2.98 (95% Confidence Interval [2.13, 4.06]) per 100 woman-years of system use.

Return to fertility was assessed in 290 of the subjects in the two trials who either desired pregnancy or switched to a non-hormonal method after the trials, and all 290 subjects reported a return to fertility during the 6-month follow-up period (defined as a return of menses or pregnancy).

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A vaginal system for preventing pregnancy, the system comprising:
    a) a methyl siloxane-based polymer ring body, wherein the methyl siloxane-based polymer comprised in the ring body has a hydride/vinyl ratio from approximately 1:1 to approximately 1.3:1 before curing, the ring body having an overall diameter of 56 mm and a cross-sectional diameter of approximately 8 mm, and comprising:
        i. a first cylindrical channel having a length of approximately 27 mm and a diameter of approximately 3 mm wherein the channel is adapted to receive a first cylindrical core;
        ii. a second cylindrical channel having a length of approximately 27 mm and a diameter of approximately 3 mm wherein the channel is adapted to receive a second cylindrical core; and
        iii. TiO2;
    b) a first cylindrical core disposed within the first cylindrical channel, wherein the first cylindrical core has a diameter of approximately 3 mm and comprises at least one silicone elastomer, dibutyltin dilaurate, and a viscosity agent;
    c) a second cylindrical core disposed within the second cylindrical channel, wherein the second cylindrical core has a diameter of approximately 3 mm and comprises at least one silicone elastomer and dibutyltin dilaurate; and
    d) approximately 103 mg of segesterone acetate and approximately 17.4 mg of ethinyl estradiol, wherein both the segesterone acetate and ethinyl estradiol are contained within the cores and wherein the segesterone acetate has a particle size D90 of not more than 10 microns;

wherein
    the methyl siloxane-based polymer ring body further comprises a platinum concentration of approximately 3 ppm to approximately 10 ppm and a plurality of ethinyl estradiol molecules covalently linked to the methyl siloxane-based polymer as shown in Formula I

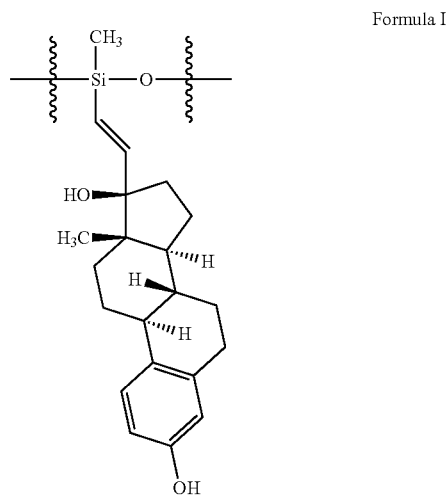

Formula I further wherein
approximately 80% to approximately 90% of the ethinyl estradiol is recoverable from the system after approximately 18 months of storage at 25° C. and 60% relative humidity; and
wherein the methyl siloxane-based polymer ring body has a shore A hardness of approximately 25 to approximately 30, a mean fatigue parallel to the cores of approximately 95%, and a mean fatigue perpendicular to the cores of approximately 98%;
further wherein the vaginal system achieves in a plasma sample of a female patient:
    i. a segesterone acetate $C_{max}$ of approximately 1,147 pg/mL+/−315 µg/mL over a twenty-one day first period during a first product-use cycle;
    ii. a segesterone acetate $C_{avg}$ of approximately 191 µg/mL+/−34 µg/mL over a twenty-one day first period during a first product-use cycle;
    iii. a segesterone acetate $AUC_{0-21}$ day of approximately 96.2 ng*hr/mL+/−16.9 ng*hr/mL over a twenty-one days first period during a first product-use cycle;
    iv. an ethinyl estradiol $C_{max}$ of approximately 129 µg/mL+/−39 µg/mL of ethinyl estradiol over a twenty-one day first period during the first product-use cycle;
    v. an ethinylestradiol $C_{avg}$ of approximately 44 pg/mL+/−19 µg/mL over a twenty-one day first period during the first product-use cycle; and
    vi. an ethinyl estradiol $AUC_{0-21}$ day of approximately 22.2 ng*hr/mL+/−9.8 ng*hr/mL over a twenty-one day first period during the first product-use cycle.

2. The vaginal system of claim 1, wherein the ethinyl estradiol is present in the cores in a first polymorphic form and a second polymorphic form.

3. The vaginal system claim 1, wherein the methyl siloxane-based polymer ring body has a specific gravity from approximately 1 to approximately 1.5.

4. The vaginal system of claim 3, wherein the methyl siloxane polymer-based ring body has a specific gravity of from approximately 1.07 to approximately 1.17.

5. The vaginal system of claim 1, wherein the total weight of the vaginal system is approximately 9 grams.

6. The vaginal system of claim 1, wherein after 36 months of storage the system comprises a total percentage of ethinyl estradiol and segesterone acetate degradation products of not more than 5 Liquid Chromatography Area Percent.

7. The vaginal system of claim 1, further comprising one or more suitable medical adhesives.

8. The vaginal system of claim 7, wherein the one or more medical adhesives comprise 15-25% trimethylsilanamine and less than 5% methylsilanetriol triacetate.

9. The vaginal system of claim 1, wherein the methyl siloxane-based polymer ring body is prepared from a first component and a second component, wherein each component comprises uncured vinyl-terminated silicone polymers.

10. The vaginal system of claim 9, wherein the first component comprises 65-75% mono(vinyl group) terminated dimethylsiloxanes and dimethylsilicones and the second component comprises 65-75% mono(vinyl group) terminated dimethylsiloxanes and dimethylsilicones, 10-15% diloxanes and silicones (dimethyl and methyl) and a platinum catalyst.

11. The vaginal system of claim 10, wherein the methyl siloxane-based polymer ring body is prepared by mixing an approximately 9:1 to approximately 11:1 ratio of the first component to the second component.

12. The vaginal system of claim 1, wherein the release rate of ethinyl estradiol from the system 48 hours after initial insertion is about 62 µg/mL.

13. The vaginal system of claim 1, wherein the release rate of ethinyl estradiol from the system 48 hours after initial insertion is about 50 µg/mL.

14. The vaginal system of claim 1, wherein the release rate of ethinyl estradiol from the system 48 hours after initial insertion is about 45 µg/mL.

15. The vaginal system of claim 1, wherein the ethinyl estradiol achieves steady state from about 168 and about 504 hours after initial insertion.

* * * * *